(12) United States Patent
Palanki et al.

(10) Patent No.: US 6,399,606 B1
(45) Date of Patent: Jun. 4, 2002

(54) NEUROPROTECTIVE AGENTS AND METHODS RELATED THERETO

(75) Inventors: Moorthy S. S. Palanki, Encinitas; Shripad S. Bhagwat, San Diego, both of CA (US); Hiroshi Sato, Omiya (JP); Paul E. Erdman, San Diego, CA (US); Mary Doubleday, Doylestown, PA (US)

(73) Assignee: Nippon Kayaku Co., Ltd., Tokyo (JP)

( * ) Notice: Subject to any disclaimer, the term of this patent is extended or adjusted under 35 U.S.C. 154(b) by 0 days.

(21) Appl. No.: 09/724,351

(22) Filed: Nov. 27, 2000

Related U.S. Application Data

(60) Provisional application No. 60/240,915, filed on Nov. 29, 1999.

(51) Int. Cl.$^7$ ................ A61K 31/5377; A61K 31/4545; A61K 31/4427; C07D 401/12; C07D 413/12; C07D 403/12; A61P 25/00

(52) U.S. Cl. .................... 514/237.2; 514/252.18; 514/275; 514/318; 514/332; 514/340; 514/341; 514/354; 514/355; 514/336; 514/338; 514/343; 514/314; 514/339; 514/342; 544/124; 544/129; 544/297; 544/360; 546/314; 546/315; 546/262; 546/285; 546/193; 546/172; 546/269.7; 546/284.7; 546/280.4; 546/277.4; 546/273.1; 546/276.4; 546/279.1; 546/272.7; 546/268.1

(58) Field of Search .................. 546/314, 315, 546/262, 285, 193, 172, 269.7, 284.7, 280.4, 277.4, 273.1, 276.4, 279.1, 272.7, 268.1; 544/124, 360, 297, 129; 514/354, 355, 332, 318, 237.2, 342, 336, 339, 338, 343, 314, 252.18, 341, 275, 340

(56) References Cited

U.S. PATENT DOCUMENTS 6,268,384 B1 * 7/2001 Novak ........................ 514/332

FOREIGN PATENT DOCUMENTS

| EP | 999204 A1 | 5/2000 |
| WO | WO 99/05091 | 2/1999 |

* cited by examiner

*Primary Examiner*—Evelyn Mei Huang
(74) *Attorney, Agent, or Firm*—Seed Intellectual Property Law Group PLLC

(57) ABSTRACT

Neuroprotective agents are disclosed having the following structure:

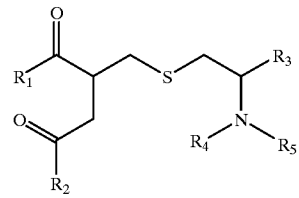

wherein $R_1$, $R_2$, $R_3$, $R_4$ and $R_5$ are as defined herein. Such compounds have utility in the treatment of conditions which benefit from administration of neuroprotective agents generally, including treatment of central and peripheral nervous condition as well as for promoting nerve cell differentiation. Methods of treating such conditions are also disclosed, as are pharmaceutical compositions containing one or more of the compounds of this invention.

28 Claims, 3 Drawing Sheets

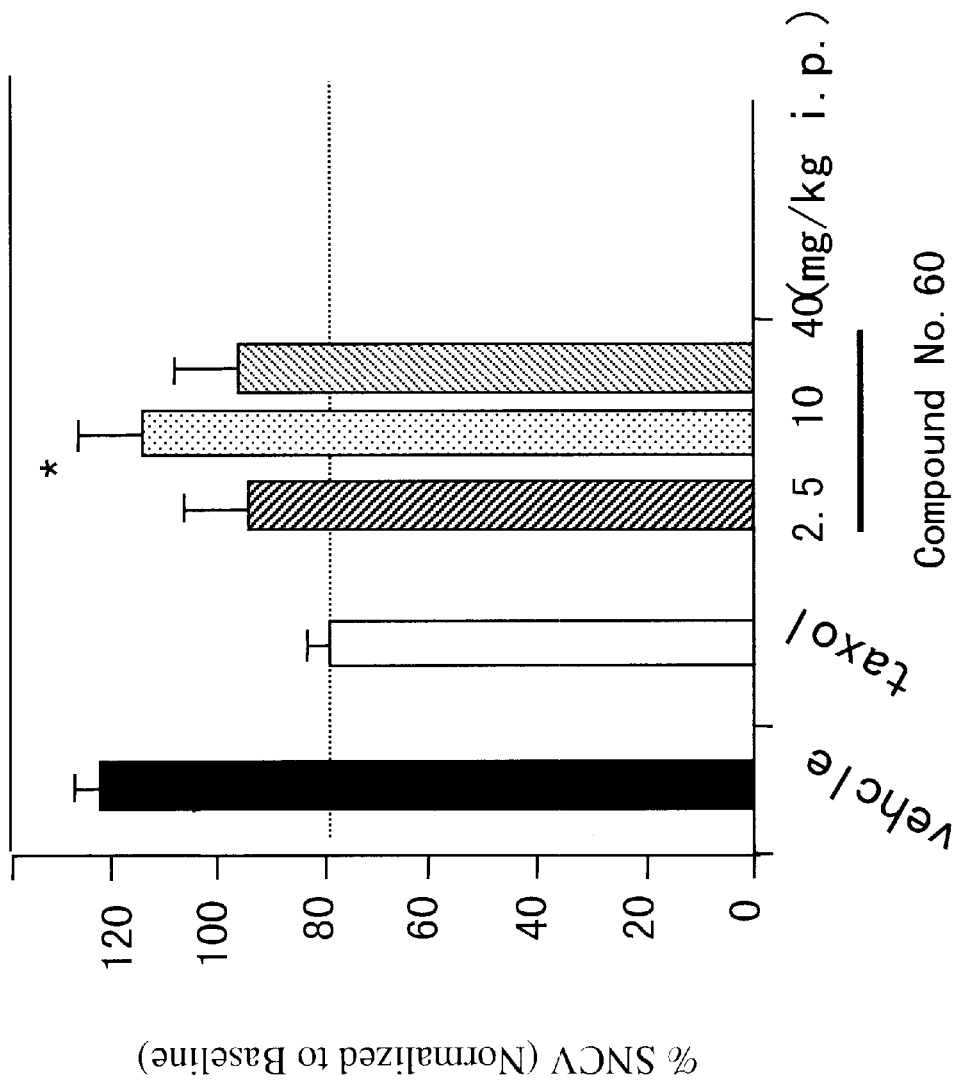
Fig.1 Effect in rat taxol neuropathy model

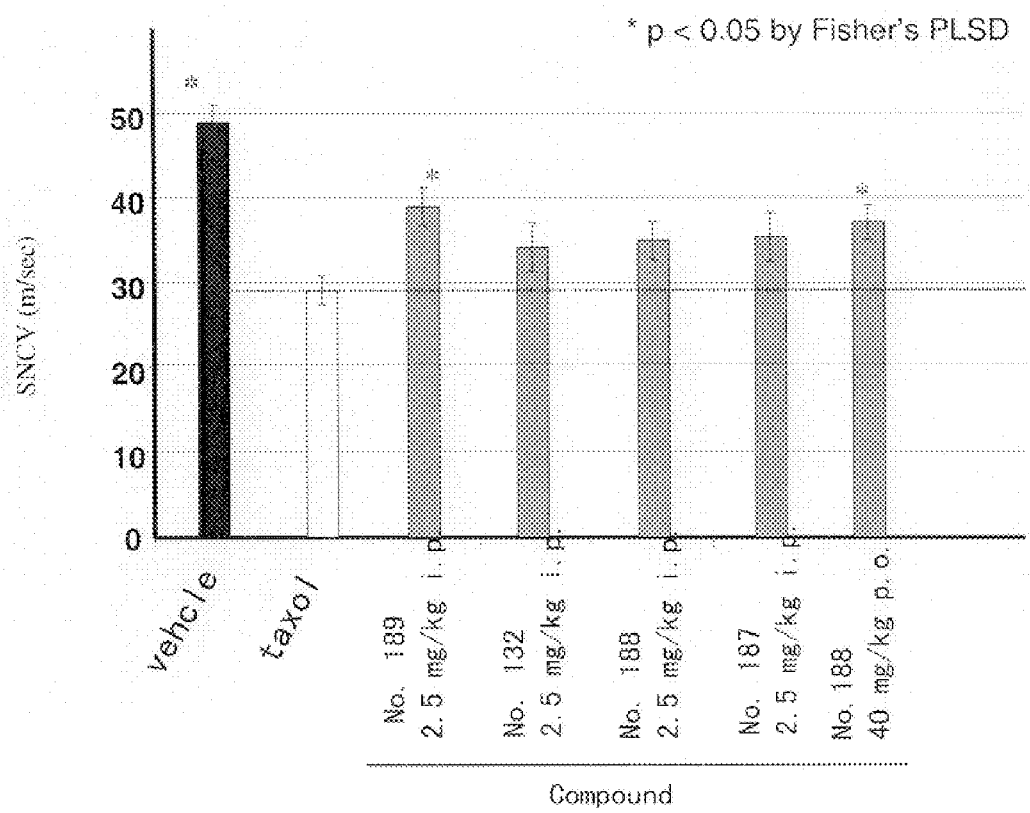
Fig. 2 Effect in rat taxol neuropathy model

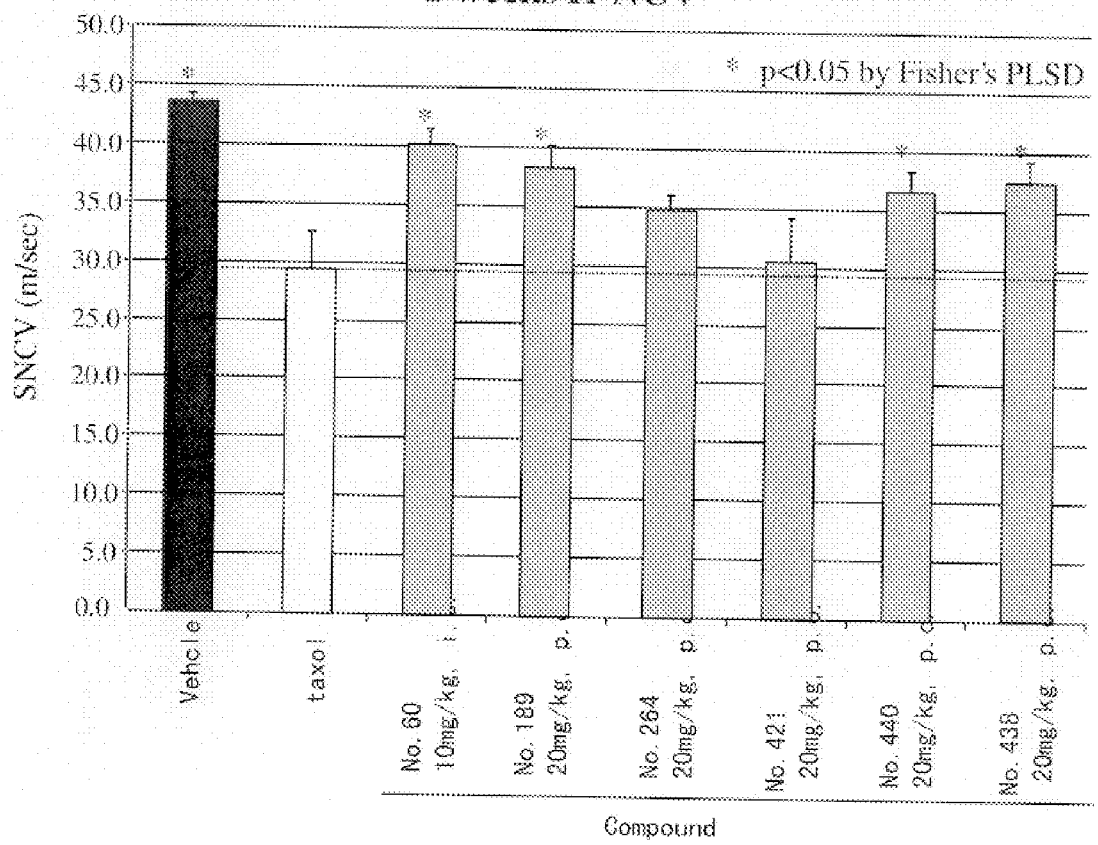

NEUROPROTECTIVE AGENTS AND METHODS RELATED THERETO

CROSS-REFERENCE TO RELATED APPLICATION

This applications claims the benefit of U.S. Provisional Application No. 60/240915 filed July 25, 2000; which provisional application was originally filed as U.S. Application No. 09/450,245 filed Nov. 29, 1999 and converted to the above-identified provisional application by Petition mailed Jul. 25, 2000.

TECHNICAL FIELD

This invention is generally directed to neuroprotective agents, pharmaceutical compositions containing the same, as well as to methods related to the use of such neuroprotective agents.

BACKGROUND OF THE INVENTION

Neurotrophic factors are a group of proteinaceous compounds that participate in differentiation induction of neurons to maintain the existence and survival of cells, of which nerve growth factors (NGFs) are a representative class. NGFs are involved in the differentiation, existence, maintenance and/or repair of neurons in both the central and peripheral nervous systems of animals and represent a series of proteins having molecular weights of approximately 50,000 daltons.

Damage to nerves caused by either aging or internal/external factors often develop paphological symptoms. In the central nervous system, such damage is found to cause, for example, Alzheimer's disease, dementia induced by cerebro-vascular disorders, disturbance of consciousness due to cerebral contusion, and tremor or muscle rigidity associated with Parkinson's disease. Similarly, damage to the peripheral nervous system is associated with a number of conditions, such as amyotropic lateral sclerosis, spinal muscle atrophy, motor function disturbances due to neuron damage, neuropathy induced by diabetes mellitus, uremia, vitamin $B_1$ or $B_{12}$ deficiency, chronic liver disease, sarcoidosis, amyloidosis, hypothyrea, cancer, angiopathy, Sjögren symptoms, immunopathy accompanied by infections, hereditary disease, physical compression, certain types of drugs (e.g., carcinostatic, tuberculostatic and/or anti-epileptic agents), or upon exposure to, for example, arsenic, thallium or carbon disulfide.

Since neurons may suffer damage from numerous events, indentification of a neurotropic factor which can regenerate and/or repair of damaged neurons is highly desirably. To this end, a recent attempt has involved the clinical application of NGF to conditions such as Alzheimer's disease, neural damage or spinal injury. For example, when NGF is present, PC 12 cells terminate cell proliferation and differentiate into neuron-like cells with neurites. This has allowed screening for active substances which have NGF-like neuron differentiation/promoting activity. Substances identified in this manner include antibiotic staurosporin and certain cystacycline compounds. Unfortunately, both of these substances have drawbacks with respect to toxicity and kinetics.

More recently, compounds with neuron differentiation promoting activity have been reported in published PCT WO 99/05091 (Nippon Kayaku Co. Ltd.). Such compounds of this published PCT encompass a wide range of structures, including compounds of the following formulas (1A) through (1F):

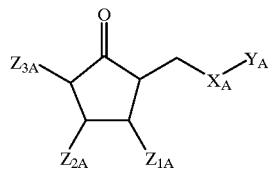

(1A)

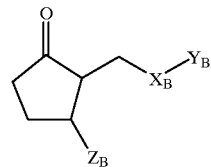

(1B)

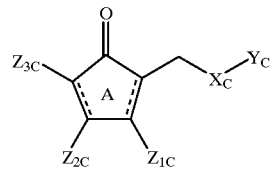

(1C)

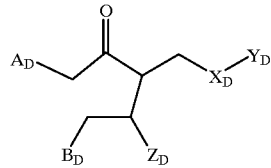

(1D)

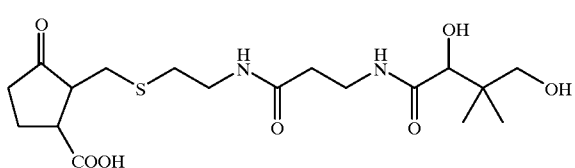

(1E)

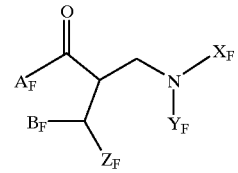

(1F)

While significant advances have been made in this field, there is still a need in the art for novel neuroprotective agents, particularly low molecular weight compounds, as well as related compositions and methods of use. The present invention fulfills these needs and provides further related advantages.

SUMMARY OF THE INVENTION

In brief, the present invention is directed to compounds having activity as neuroprotective agents (also referred to herein as simply "compounds"), as well as to compositions and methods related thereto. As used herein, the term "neuroprotective agent" means a compound that prevents neuron cell death.

The compounds of the present invention have the following structure (I):

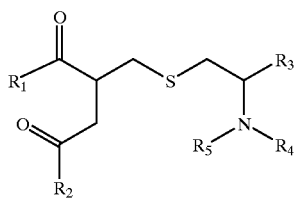

(I)

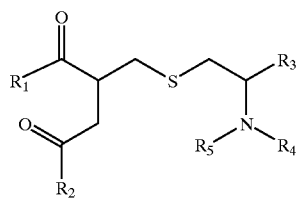

(I)

wherein $R_1$, $R_2$, $R_3$, $R_4$ and $R_5$ are as defined below, including stereoisomers and pharmaceutically acceptable salts thereof.

The present invention is also directed to methods for treating a variety of conditions by administering an effective amount of a neuroprotective agent of this invention to an animal or subject in need thereof (referred to herein as a "patient"), typically a warm-blooded animal (including a human). Prior to administration, the compounds of this invention are preferably formulated as a pharmaceutical composition which contains an effective dosage amount of one or more neuroprotective agents in combination with one (or more) pharmaceutically acceptable carrier(s).

Conditions that may be treated by the compounds of this invention, or a pharmaceutical composition containing the same, include any condition which may benefit from administration of neuroprotective agents generally, and are particularly useful for the prevention and/or treatment of various conditions including (but not limited to) increased intracraniel pressure and cerebral herniation, cerebral edema, hydrocephalus, meningitis, encephalitis, ischemic encephalopathy, cerebral infarction, intracranial hemorrhage, epidermal hematoma, subdural hematoma, parenchymal injuries, Alzheimer's deasease, Huntington's disease, Parkinsonism, amytrophic lateral sclerosis, multiple sclerosis, hepatic encephalopathy, leukodystrophy, acute idiopathic neuropathy, neurilemmoma, and/or neurofibroma.

These and other aspects of this invention will be apparent upon reference to the following detailed description. To that end, certain patent and other documents are cited herein to more specifically set forth various aspects of this invention. Each of these documents are hereby incorporated by reference in their entirety.

BRIEF DESCRIPTION OF THE DRAWINGS

FIG. 1 shows the effect of a representative compound according to the present invention in a rat taxol-induced neuropathy model.

FIG. 2 shows the effects of representative compounds according to the present invention on a rat taxol-induced neuropathy model.

FIG. 3 shows the effects of representative compounds according to the present invention on a rat taxol-induced neuropathy model.

DETAILED DESCRIPTION OF THE INVENTION

As mentioned above, the present invention is directed to compounds which have activity as neuroprotective agents, as well as to compositions and methods relating to the same. The compounds of this invention have the following structure (I):

and stereoisomers and pharmaceutically acceptable salts thereof, wherein:

$R_1$ is alkyl, substituted alkyl, aryl, substituted aryl, arylalkyl, substituted arylalkyl, heterocycle, substituted heterocycle, heterocyclealkyl or substituted heterocyclealkyl;

$R_2$ is —$OR_{2a}$ or —$NR_{2b}R_{2c}$;

$R_3$ is hydrogen, keto, —C(=O)$OR_{3a}$, or —C(=O)$NR_{3b}R_{3c}$;

$R_4$ is hydrogen, alkyl, substituted alkyl, aryl, substituted aryl, C(=O)$R_{4a}$, —C(=O)$OR_{4b}$, —C(=O)$NR_{4c}R_{4d}$, —OC(=O)$NR_{4c}R_{4d}$ or —$SO_2R_{4e}$.

or wherein $R_3$ and $R_4$ taken together form a heterocyclic ring or substituted heterocyclic ring; and $R_5$ is hydrogen, alkyl or substituted alkyl;

and wherein:

$R_{2a}$ is hydrogen, alkyl, substituted alkyl, aryl, substituted aryl, arylalkyl, substituted arylalkyl, heterocycle, substituted heterocycle, heterocyclealkyl, or substituted heterocyclealkyl;

$R_{2b}$ and $R_{2c}$ are the same or different and independently hydrogen, alkyl, substituted alkyl, aryl, substituted aryl, heteroaryl, substituted heteroaryl or a radical of the formula —$OR_{2d}$, —C(=O)$R_{2d}$ or —$SO_2R_{2d}$ wherein $R_{2d}$ is alkyl, substituted alkyl, aryl or substituted aryl, or $R_{2b}$ and $R_{2c}$ taken together with the nitrogen atom to which they are attached from a heterocyclic ring or substituted heterocyclic ring;

$R_{3a}$, $R_{3b}$ and $R_{3c}$ are the same or different and independently hydrogen, alkyl, substituted alkyl, aryl, substituted aryl, arylalkyl, substitued arylalkyl, heterocycle, substituted heterocycle, heterocyclealkyl, substituted heterocyclealkyl, or a radical of the formula —$Y_3$—$Z_3$—$R_{3d}$, where $Y_3$ is alkanediyl, substitute alkanediyl or a direct bond, $Z_3$ is —O—, —S—, —$SO_2$—, —N($R_{3e}$)—, —C(=O)—, —C(=O)O—, —OC(=O)—, —NHC(=O)—, —C(=O)N($R_{3e}$)— or a direct bond, and wherein $R_{3d}$ and $R_3$ are the same or different and independently hydrogen, amino, alkyl, substituted alkyl, aryl, substituted aryl, arylalkyl, substituted arylalkyl, heterocycle, substituted heterocycle, heterocyclealkyl or substituted heterocyclealkyl; or $R_{3b}$ and $R_{3c}$ taken together with the nitrogen atom to which they are attached from a heterocyclic ring or substituted heterocyclic ring; and $R_{4a}$, $R_{4b}$, $R_{4c}$, $R_{4d}$ and $R_{4e}$ are the same or different and independently hydrogen, alkyl, substituted alkyl, aryl, substituted aryl, arylalkyl, substituted arylalkyl, or a radical of the formula -$Y_4$-$Z_4$-$R_{4f}$, where $Y_4$ is alkanediyl, substitute alkanediyl or a direct bond, $Z_4$ is —O—, —$SO_2$—, —N($R_{4g}$)—, —C(=O)—, —C(=O)O—, —OC(=O)—, —NHC(=O)—, —C(=O)N($R_{4g}$)— or a direct bond, and wherein $R_{4f}$ and $R_{4g}$ are the same or different and independently hydrogen, amino, alkyl, substituted alkyl, aryl, substituted aryl, arylalkyl, substituted arylalkyl, heterocycle, substituted heterocycle, heterocyclealkyl or substituted heterocyclealkyl, or $R_{4f}$ and $R_{4g}$ taken together with the nitrogen atom to which they are attached form a heterocycle or substituted heterocycle, or $R_4$ and $R_{4d}$ taken together with the nitrogen atom to which they are attached from a heterocyclic ring or substituted heterocyclic ring.

As used herein, the terms used above having following meaning.

"Alkyl" means a straight chain or branched, saturated or unsaturated alkyl, cyclic or non-cyclic hydrocarbon having from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclo pentane or cyclohexane) fused to one or more aromatic (such as phenyl) or non-aromatic (such as cyclohexane) carbocyclic rings.

"Alkanediyl" means a divalent alkyl group having two hydrogen atoms taken from the same carbon atom or different carbon atoms of the alkyl, such as —$CH_2$—, —CH($CH_3$)—, —CH($CH_3$)$CH_2$—, —$CH_2CH_2CH_2$—, —$CH_2$CH($CH_3$)$CH_2$—, —(cyclohexyl)—, and the like.

"Halogen" means fluorine, chlorine, bromine or iodine.

"Keto" means a carbonyl group (i.e., =O).

"Aryl" means an aromatic carbocyclic moiety such as phenyl or naphthyl.

"Arylalkyl" means an alkyl having at least one alkyl hydrogen atoms replaced with an aryl moiety, such as benzyl, —($CH_2$)$_2$phenyl, —($CH_2$)$_3$phenyl, —CH(phenyl)$_2$, and the like. "Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like. "Heterocycle" means a heterocyclic ring containing from 5 to 10 ring atoms "Heterocycle" means a 5- to 7-membered monocyclic, or 7- to 10- membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. "Heterocyclealkyl" means an alkyl having at least one alkyl hydrogen atom replaced with a heterocycle, such as —$CH_2$morpholinyl, and the like.

The term "substituted" as used herein means any of the above groups (i.e., alkyl, alkanediyl, aryl, arylalkyl, heteroaryl, heteroarylalkyl, heterocycle and heterocyclealkyl) wherein at least one hydrogen atom is replaced with a substituent. In the case of a keto substituent ("C(=O)") two hydrogen atoms are replaced. Substituents include halogen, hydroxy, alkyl, substituted alkyl (such as haloalkyl, mono— or di-substituted aminoalkyl, alkyloxyalkyl, and the like), aryl, substituted aryl, arylalkyl, substituted arylalkyl, heterocycle, substituted heterocycle, heterocyclealkyl, substituted heterocyclealkyl, —$NR_aR_b$, $NR_aC(=O)R_b$, —$NR_aC(=O)NR_aR_b$, $NR_aC(=O)OR_b$ —$NR_aSO_2R_b$, —$OR_a$, —$C(=O)R_a$ —$C(=O)OR_a$—C(=O)$NR_aR_b$, —OC(=O)$R_a$, —OC(=O)$OR_a$, —OC(=O)$NR_aR_b$, —$NR_aSO_2R_b$, or a radical of the formula -Y-Z-$R_a$ where Y is alkanediyl, substitute alkanediyl, or a direct bond, Z is —O—, —S—, —$SO_2$—, —N($R_b$)—, —C(=O)—, —C(=O)O—, —OC(=O)—, —N($R_b$)C(=O)—, —C(=O)N($R_b$)— or a direct bond, wherein $R_a$ and $R_b$ are the same or different and independently hydrogen, amino, alkyl, substituted alkyl (including halogenated alkyl), aryl, substituted aryl, arylalkyl, substituted arylalkyl, heterocycle, substituted heterocycle, heterocyclealkyl or substituted heterocyclealkyl, or wherein $R_a$ and $R_b$ taken together with the nitrogen atom to which they are attached form a heterocycle or substituted heterocycle.

In one embodiment of this invention, $R_1$ is pyridinyl. In a more specific embodiment of this aspect, $R_1$ is pyridin-3-yl, and compounds of this invention have the following structure:

(II)

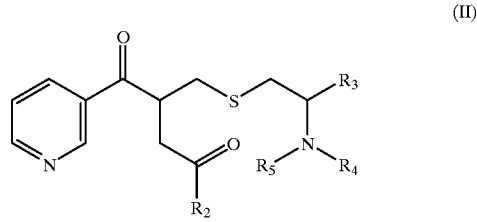

In a further embodiment of structure (II), $R_2$ is —$NR_{2b}R_{2c}$, and compounds of this invention have the following structure (III):

(III)

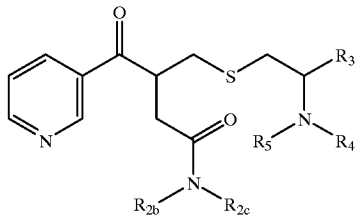

In still a further embodiment of structure (III), $R_3$ and $R_5$ are hydrogen, and compounds of this invention have the following structure (IV):

(IV)

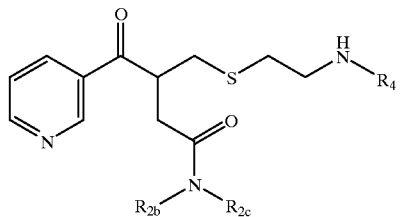

In yet a further embodiment of structure (V), $R_{2b}$ and $R_{2c}$ taken together with the nitrogen atom to which they are attached form piperidyl, and the compounds of this invention have the following structure (V):

(V)

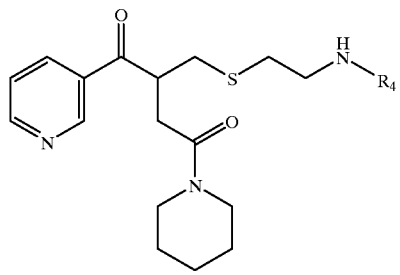

In a more specific embodiment of structure (V), $R_4$ is, —C(=O)$R_{4a}$, —C(=O)O$R_{4b}$ or —C(=O)N$R_{4c}R_{4d}$, and compounds of this invention have the following structures (VI), (VII) or (VIII), respectively:

(VI)

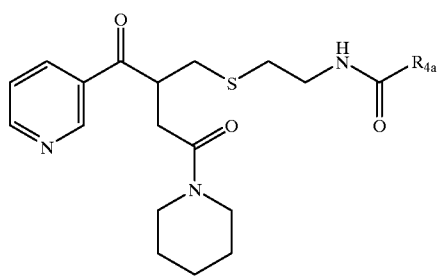

(VII)

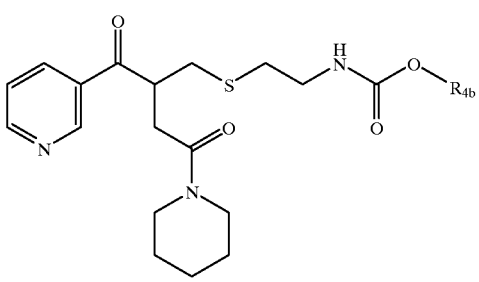

(VIII)

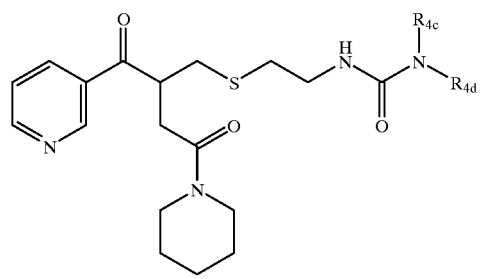

In a further embodiment of structure (I), compounds of this invention have the following structure (IX):

(IX)

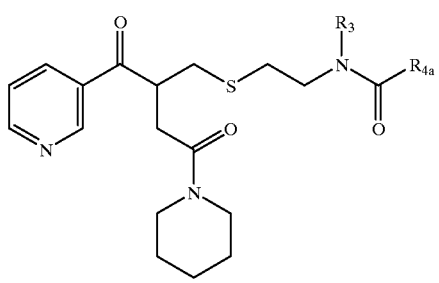

wherein $R_3$ is, in one embodiment, alkyl or substituted alkyl.

In one representative embodiment, $R_1$ is heterocycle and, more specifically, an aromatic heterocycle (i.e., heteroaryl) such as pyridin-2-yl or pyridin-3-yl. In another embodiment, $R_1$ is aryl such as phenyl, or alkyl (including cycloalkyl). In still a further embodiment, $R_1$ is heteroaryl such as thiazolyl.

In another representative embodiment, $R_2$ is —O$R_{2a}$ wherein $R_{2a}$ is hydrogen or an alkyl group such as methyl, ethyl, n-propyl, n-butyl, t-butyl or —CH$_2$(cyclopropyl), or a substituted alkyl such as —(CH$_2$)$_2$NH$_2$, —CH$_2$(OC(=O)t-butyl). In another embodiment, $R_{2a}$ is aryl such as phenyl or substituted aryl such as 4-chlorophenyl, or arylalkyl, such as benzyl (i.e., —CH$_2$phenyl) or —(CH$_2$)$_2$phenyl. In a further embodiment, $R_{2a}$ is heterocyclealkyl, such as —(CH$_2$)$_2$morpholinyl, —(CH$_2$)$_2$indolyl, —(CH$_2$)$_{2,3}$piperidinyl, —(CH$_2$)$_3$pyridinyl or —(CH$_2$)$_2$thiophenyl.

In a further representative embodiment, $R_2$ is —N$R_{2b}R_{2c}$, wherein $R_{2b}$ is hydrogen and $R_{2c}$ is alkyl, substituted alkyl (e.g., (CH$_2$)$_3$OCH$_3$), arylalkyl (e.g. benzyl) or heteroarylalkyl (e.g. —CH$_2$pyridinyl or —CH$_2$thiophenyl). In another embodiment, $R_{2c}$ is —O$R_{2d}$ or —SO$_2R_{2d}$ wherein $R_{2d}$ is alkyl such as methyl, aryl such as phenyl or arylalkyl such as benzyl. In a further embodiment, $R_{2b}$ and $R_{2c}$ are both alkyl such as methyl or ethyl. In still a further embodiment, $R_{2b}$ and $R_{2c}$ taken together form a heterocycle ring such as pyrrolidinyl, piperidinyl and morpholinyl.

In still a further representative embodiment, $R_3$ is hydrogen or keto (i.e., =O). In another embodiment, $R_3$ is carbonyl (i.e., —COOH) or an alkyl ester of the formula —C(=O)OR$_{3a}$, such as methyl ester (i.e., —C(=O)OMe) or ethyl ester (i.e., —C(=O)OEt). In still a further embodiment, $R_3$ is an amide of the formula —C(=O)NR$_{3b}$R$_{3c}$, such as dialkylamide (e.g., —C(=O)N(CH$_3$)$_2$), cycloalkylamide (e.g., —C(=O)NH(cyclohexyl)), arylalkylamide (e.g., —C(=O)NH(CH$_2$)$_3$phenyl), heterocycle alkylamide (e.g., —C(=O)N(CH$_2$)$_3$imidazolyl, —C(=O)N(CH$_2$)$_2$pyridinyl, —C(=O)NH(CH$_2$)$_3$morpholinyl), substituted alkylamide (e.g., —C(=O)N(CH$_3$)(CH$_2$)$_{2-3}$N(Me)$_2$ or —C(=O)N(CH$_3$)(CH$_2$)$_2$N(Et)$_2$, or wherein $R_{3b}$ and $R_{3c}$ taken together form a heterocyclic ring such as the following structures (i) through (v):

(i)
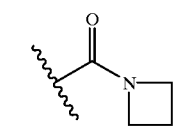

(ii)
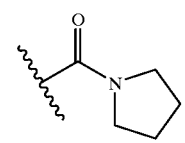

(iii)
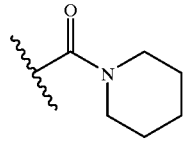

(iv)
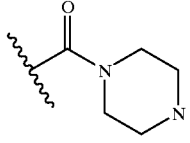

(v)
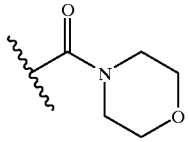

or wherein $R_{3b}$ and $R_{3c}$ taken together form a substituted heterocyclic ring such as the following structures (vi) through (x):

(vi)
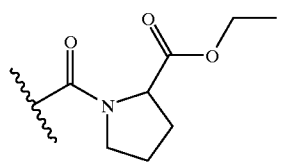

(vii)
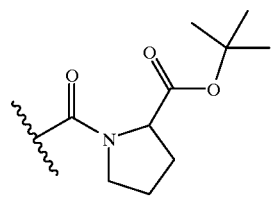

(viii)
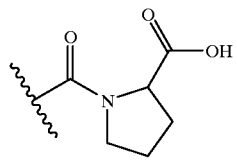

(ix)
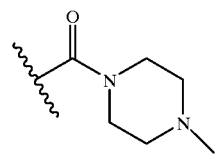

(x)
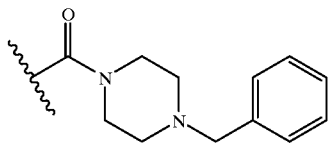

Representative $R_4$ moieties of this invention include (but are not limited to) those listed in Table 1 of Example 45. For example, one representative embodiment, $R_4$ is hydrogen, alkyl such as methyl or ethyl, aryl such as phenyl or naphthyl, or arylalkyl such as benzyl. In another embodiment, $R_4$ is —C(=O)R$_{4a}$. In this embodiment, representative $R_{4a}$ groups include alkyl and substituted alkyl, as well as aryl, substituted aryl, arylalkyl and substituted arylalkyl. Further representative $R_{4a}$ groups include heterocycle, substituted heterocycle, heterocyclealkyl and substituted heterocyclealkyl. In another embodiment, $R_4$ is —C(—O)OR$_{4b}$. In this embodiment, representative $R_{4b}$ groups include alkyl, substituted alkyl, aryl and substituted aryl. In still another embodiment, $R_4$ is —C(=O)NR$_{4c}$R$_{4d}$ or —OC(=O)NR$_{4c}$R$_{4d}$. In this embodiment, representative $R_4$, and $R_{4d}$ groups include alkyl, substituted alkyl, aryl, and substituted aryl. In yet a further embodiment, $R_4$ is —SO$_2$R$_{4e}$. In this embodiment, representative $R_{4c}$ groups include alkyl, substituted alkyl, aryl, substituted aryl, arylalkyl, and substituted arylalkyl, as well as heterocycle and substituted heterocycle.

In a further representative embodiment, $R_3$ and $R_4$ taken together form a substituted or unsubstituted heterocyclic ring of the following structure (xi):

(xi)
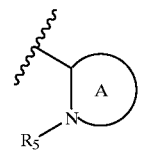

wherein ring A represents a heterocyclic ring as defined above. Representative heterocyclic rings in this regard include pyrrolyl, imidazolyl, pyrazolyl, pyrrolidinyl, pyridinyl, pyrimidinyl, and the like, as well as keto-substituted heterocycles such as hydantinyl, ketopiperazinyl, diketopiperazinyl, and the like. In one representative embodiment, $R_3$ and $R_4$ are taken together to form a substituted heterocyclic ring having the following structures (xii), (xiii) or (xiv):

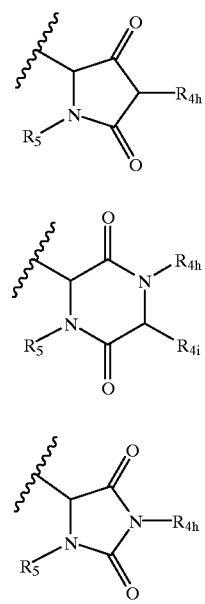

(xii)

(xiii)

(xiv)

wherein $R_{4b}$ and $R_{4i}$ represents the same or difference substituents as defined above, such as hydrogen or alkyl.

In another representative embodiment, $R_5$ is hydrogen. In another emobiment, $R_5$ is alkyl such as methyl, ethyl, n-propyl, n-butyl and cyclohexyl.

Pharmaceutically acceptable salts of compounds of structure (I) are also within the scope of this invention. To this end, the compound may generally be utilized as the free base. Alternatively, the compounds may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, 1,2-ethanedisulfonic, acetic, oxalic, propionic, tartaric, salicylic, citric, gluconic, lactic, mandelic, cinnamic, aspartic, stearic, palmitic, glycolic, glutamic, benzenesulfonic, p-tolyenesulfonic, hippuric, sebacic, 2-hydroxy-1-naphthoic and perchloric acids. Suitable inorganic acids include hydrochloric, hydrobromic, sulfuric, phosphoric, and nitric acids. Thus, the term "pharmaceutically acceptable salt" of a compound of structure (I) is intended to encompass any and all acceptable salt forms.

With regard to stereoisomers, the compounds of structure (I) may have chiral centers and may occur as recemates, reacemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of this invention may generally be made by organic synthesis techniques known to those skilled in the art, as well as by the following general techniques and by the procedures set forth in the Examples. To that end, the compounds of this invention may be made according to the following Reaction Schemes.

Reaction Scheme 1

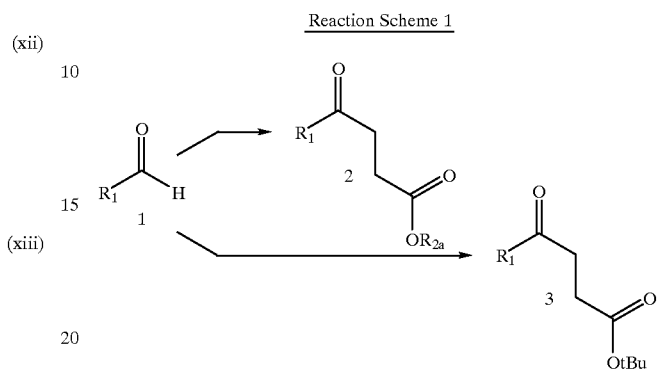

In Reaction Scheme 1, compound 2 may be prepared by treating aldehyde 1 with an acrylate ester in the presence of sodium cyanide in dimethylformamide solvent. Similarly, compound 3 can be prepared from aldehyde 1 using the above conditions.

Reaction Scheme 2

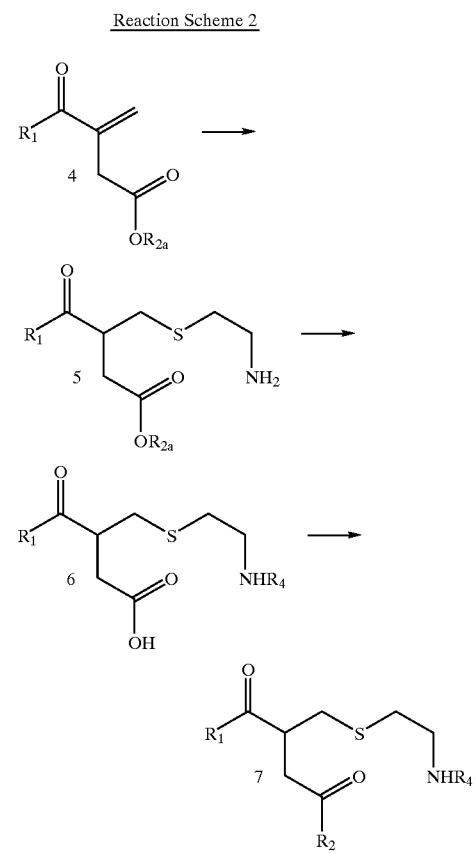

In Reaction Scheme 2, compound may be prepared from compound 2 by treating it with piperidine and aqueous formaldehyde in tetrahydrofuran. The piperidyl adduct intermediate can be treated with hydrochloric acid to give compound 4. Treatment of compound 4 with 2-aminoethanethiol in tetrahydrofuran will result in compound 5. The amine group in compound 5 can be converted to amides (by treating with acid chloride), carbamates (by treating with chloroformates) and ureas (by treating with isocyanates) in dichloromethane or tetrahydrofuran. Once the amine group was converted to $NHR_4$, the ester group $OR_{2a}$ can by hydrolyzed either under basic (using sodium hydroxide) or acidic (hydrochloric acid) to give compound 6. The acid group in compound 6 can be functionalized to an amide by standard coupling conditions using a carbodiimide (such as ethyl diisopropyl carbodiimide) in a suitable solvent (such as tetrahydrofuran or dichloromethane).

Reaction Scheme 3

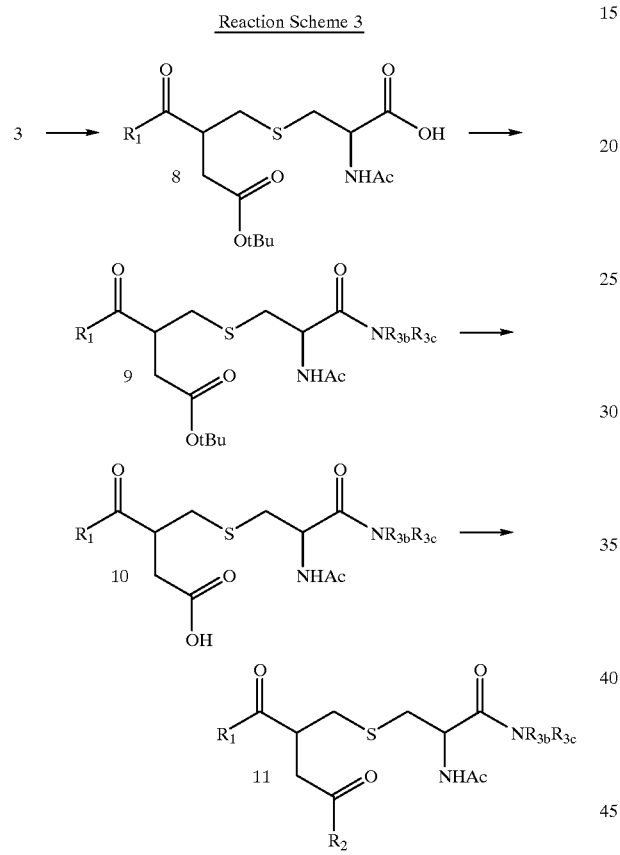

Reaction Scheme 4

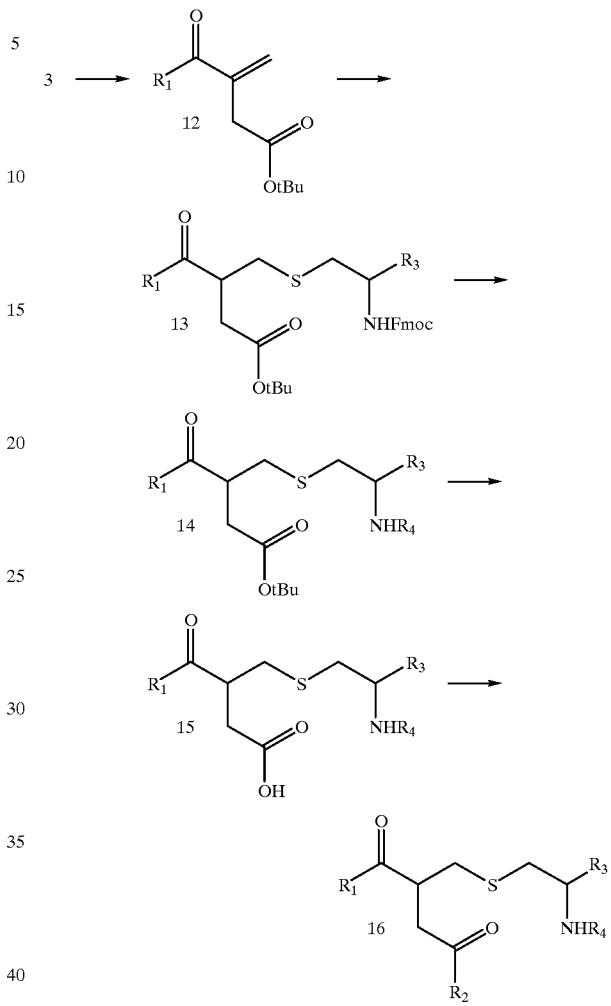

In Reaction Scheme 3, compound 8 can be prepared from compound 3 by treatment with piperidine and aqueous formaldehyde in tetrahydrofuran. The intermediate piperidyl adduct can be treated with N-acetyl cysteine in tetrahydrofuran or ethanol to give compound 8. The acid group in compound 8 can be further functionalized to an amide by treating with an amine and a suitable carbodiimide (such as ethyl diisopropyl carbodiimide) in dichloromethane or tetrahydrofuran. The t-butyl ester in compound 9 can be hydrolyzed to an acid, as in compound 10, using an acid (such as hydrochloric acid). The acid group in compound 10 can be converted to an ester ($R_2=OR_{2a}$ in compound 11) by treating with an alkyl halide, triethylamine in dimethylformamide or to an amide ($R_2=NR_{2b}R_{2c}$ in compound 11) by using an amine and standard carbodiimide coupling procedure.

In Reaction Scheme 4, compound 12 can be prepared from compound 3 by treating it with piperidine and aqueous formaldehyde in tetrahydrofuran. The piperidyl adduct intermediate can be treated with a limited amount of hydrochloric acid to give compound 12. Treatment of compound 12 with an appropriately substituted thiol in tetrahydrofuran resulted in compound 13. The Fmoc group on compound 13 can be cleaved with piperidine in dimethylformamide to give the free amine. This free amine can be functionalized to an amide ($R_4=C(=O)R_{4a}$ in compound 14) using an acid chloride, or to a carbamate ($R_4=C(=O)OR_{4b}$ in compound 14) using a chloroformate or to a urea ($R_4=C(=O)NR_{4c}R_{4d}$ in compound 14) using an isocyanate. The t-butyl ester in compound 14 can be cleaved to a free acid using hydrochloric acid in water-tetrahydrofuran solvent system to give compound 15. The acid group in compound 15 can be functionalized to an amide by standard coupling conditions using a carbodiimide (such as ethyl diisopropyl carbodiimide) in a suitable solvent (such as tetrahydrofuran or dichloromethane), or to an ester by treating with an alkyl halide, triethylamine in dimethylformamide.

Reaction Scheme 5

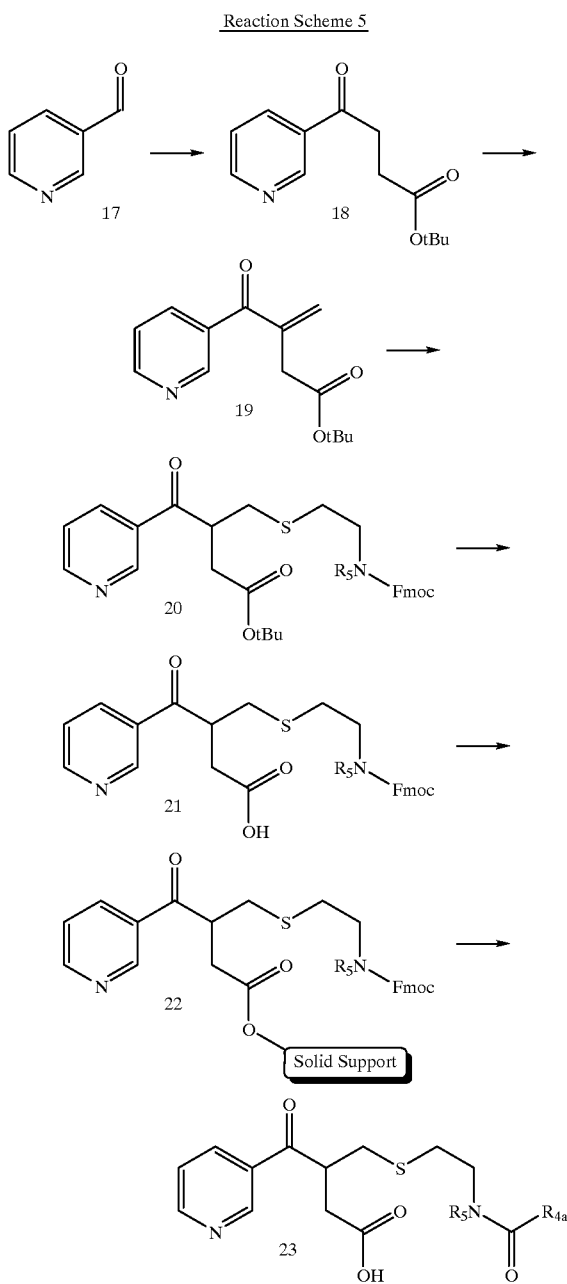

In Reaction Scheme 5, treatment of compound 17, 3-pyridinecarboxaldehyde, with sodium cyanide and t-butyl acrylate in dimethylformamide results in compound 18. Compound 18 may be converted to compound 19 using piperidine and aqueous formaldehyde in tetrahydrofuran to give a piperidyl adduct. The intermediate piperidyl adduct can be treated with limited amount of hydrochloric acid to give compound 19. Compound 19 can be converted to compound 20 using N-Fmoc-protected cysteamine in tetrahydrofuran. The t-butyl group in compound 20 can be cleaved to give free acid 21 using trifluoroacetic acid in dichloromethane. The acid 21 can be attached to a solid phase resin (such as 2-chlorotrityl resin) in the presence of diisopropylethylamine to give compound 22. The FMOC group in compound 22 can be cleaved using piperidine in dimethylformamide to give free amine, which can be treated with either an acid chloride to give an amide, or a chloro- formate to give a carbamate, or to an isocyanate to give a urea. Compound 23 can be cleaved off the resin using trifluoroacetic acid in dichloromethane.

In another embodiment of the invention, pharmaceutical compositions containing one or more compounds of this invention are disclosed. For purpose of administration, a compound of structure (I) is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Preferably, the pharmaceutical compositions of the present invention include a compound of structure (I) in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in *Remington's Pharmaceutical Sciences*, Gennaro, Ed., Mack Publishing Co., Easton, P.a. 1990.

In another embodiment, the present invention provides a method for treating a variety of conditions by administering an effective amount of a compound of structure (I) to a patient in need thereof. As used herein, treatment includes preventative administration, as well as "rescue" treatment when, for example, a patient has already developed neuropathy. Conditions that may be treated by the compounds of this invention, or a pharmaceutical composition containing the same, include any condition which is responsive to treatment by a neuroprotective agent generally and, more specifically, for treatment of central or peripheral nervous disorders, or for promoting nerve cell differentiation. Representative conditions in this regard include (but not limited to) increased intracraniel pressure and cerebral herniation, cerebral edema, hydrocephalus, meningintis, encephalitis, ischemic encephalopathy, cerebral infarction, intracranial hemorrhage, epidermal hematoma, subdural hematoma, parenchymal injuries, Alzheimer's deasease, Huntington's disease, Parkinsonism, amytrophic lateral sclerosis, multiple sclerosis, hepatic encephalopathy, leukodystrophy, acute idiopathic neuropathy, diabetic neuropathy, chemotherapy-induced neuropathy, HIV-induced neuropathy, neurilemmoma, and/or neurofibroma.

The methods of this invention include systemic administration of a compound of this invention, preferably in the form of a pharmaceutical composition. As used herein, systemic administration encompasses both oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain buffers, antioxidants, bacteriostats, and other additives commonly employed in such solutions.

The following examples are offered by way of illustration, not limitation.

EXAMPLES

Example 1

Methyl 4-Oxo-4-(3-Pyridyl)butanoate

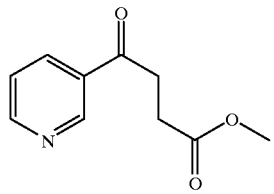

A solution of 3-pyridinecarboxaldehyde (10.7 g) in dimethyl formamide (DMF, 20 mL) was added over 10 min. to a stirred solution of sodium cyanide (2.45 g) in DMF (80 mL) at room temperature under dry nitrogen. The solution was stirred for 30 min. and methyl acrylate (18.6 g) in DMF (80 mL) was added dropwise over 50 min. The reaction mixture was stirred for 3 h. Acetic acid (6.6 mL) and water (30 mL) were added and stirring was continued for 5 minutes. The mixture was concentrated, dissolved in water (360 mL), and pH was adjusted to 7.5 with sodium bicarbonate. The aqueous layer was extracted with chloroform (3×300 mL). The chloroform layers were combined, washed with saturated sodium chloride solution (brine), dried (MgSO$_4$), filtered, concentrated and purified by flash chromatography (SiO$_2$, 30% ethyl acetate in hexanes) to yield 4.3 g (22%) of the title compound; ESMS (M+1)$^+$194.

Example 2

Ethyl 4-Oxo-4-(3-Pyridyl)butanoate

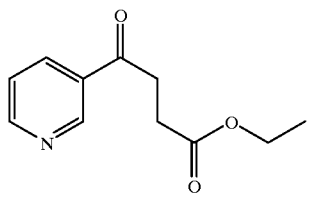

The title compound was prepared from 3-pyridinecarboxaldehyde (20 g) and ethyl acrylate (22.4 g) as described in Example 1 to yield 5.1 g, ESMS (M+1)+208.

Example 3

Ethyl 3-(3-Pyridylcarbonyl)but-3-enoate

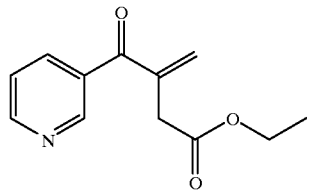

A solution of ethyl 4-oxo-4-(3-pyridyl)butanoate (4 g), 37% aqueous formaldehyde (2.46 g) and piperidine (2.46 g) was stirred at room temperature for 18 h. The reaction mixture was diluted with 200 mL of ethyl acetate and washed with water (2×100 mL). The reaction mixture was concentrated and dissolved in ethanol (10 mL) and treated with 4N HCl/dioxane (4 mL) at 80° C. for 12 h. The reaction mixture was diluted with ethyl acetate (200 mL), washed with water (2×100 mL), saturated sodium bicarbonate solution (2×100 mL), concentrated and purified on flash chromatography (20% Ethyl acetate to 80% ethyl acetate in hexane) to give 2.28 g of the title compound, ESMS (M+1)+ 220.

Example 4

Butyl 4-Oxo-4-(3-Pyridyl)butanoate

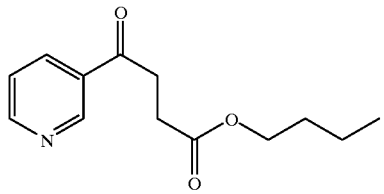

A solution of 3-pyridinecarboxaldehyde (26.8 g) in dimethyl formamide (DMF, 100 mL) was added over 10 min. to a stirred solution of sodium cyanide (7.0 g) in DMF (200 mL) at room temperature under dry nitrogen. The solution was stirred for 30 min. and n-butyl acrylate (32 g) in DMF (200 mL) was added dropwise over 60 min. The reaction mixture was stirred for 3 h. Acetic acid (20 mL) and water (80 mL) were added and stirring was continued for 10 minutes. The solution was concentrated under reduced pressure, dissolved in ethyl acetate (600 mL), washed with water (3×200 mL), brine (200 mL) and dried (Na$_2$SO$_4$). The solution was filtered, concentrated and distilled at 140° C. at 0.5 mm/Hg to give 18.2 g of the title compound as an oil; ESMS (M+1)$^+$236.

Example 5

3-{[(2R)-2-(Acetylamino)—2-(methoxycarbonyl)ethylthio]-methyl}-4-oxo-4-(3-pyridyl)butanoic Acid

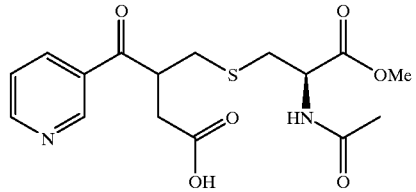

A solution of 4-oxo-3-(piperidylmethyl)-4-(3-pyridyl)butanoic acid (5.0 g), methyl N-acetyl-L-cysteine ester (4.7 g) in ethanol (44 mL) was heated at reflux for 2 h. The solution was concentrated under reduced pressure and purified on flash chromatography (SiO$_2$, CHCl$_3$: MeOH: CH$_3$COOH=20:1:0.5) to afford the title compound in 85% yield; ESMS (M+1)$^+$369.

Example 6

Methyl 3-(3-Pyridylcarbonyl)but-3-enoate

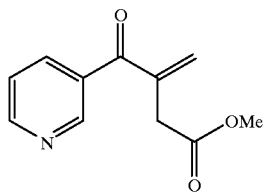

A solution of methyl 4-oxo-3-(piperidylmethyl)-4-(3-pyridyl)butanoate (4 g) in ethanol (10 mL) and 4N HCl/dioxane (4.0 mL) was heated at 80° C. for 12 hrs. The reaction mixture was concentrated and purified on flash chromatography (SIO2, CHCl$_3$: MeOH: CH$_3$COOH=10:1:0.5) to give 2.28 g of the title compound.

Example 7

3-{[2-(Acetylamino)ethylthio]methyl-4-oxo-4-(3-pyridyl)-butanoic Acid

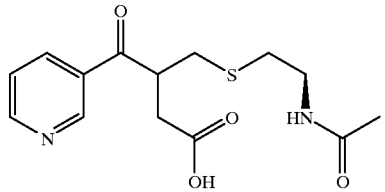

A solution of 4-oxo-4-(3-pyridyl)butanoic acid (7.0 g) in ethanol (25 mL) was heated with piperidine (3.65 g) and 37% formaldehyde in water (3.5 g) at 80° C. for 3 hrs. A solution of n-acetylcysteamine (4.65 g) in ethanol (30 mL) was added to the reaction mixture and heated at 80° C. with stirring for 3 h. The solution was concentrated and purified by flash chromatography (SiO$_2$, CHCl$_3$:MeOH:CH$_3$COOH= 20:1:0.5) to give 7.3 g of the title compound.

Example 8

4-{2-[4-Oxo-4-piperidyl-2-(3-pyridylcarbonyl)-butylthio]ethyl}-acetamide

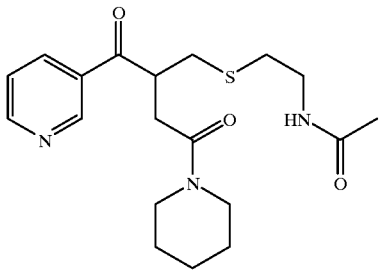

Ethylchloroformate (1.54 g) was added to a stirred solution of 3-{[2-(acetylamino)ethylthio]methyl-4-oxo-4(3-pyridyl)butanoic acid (4.0 g), triethyl amine (1 eq) in tetrahydrofuran (100 mL) at 0° C. Piperidine (1.21 g) was added to the reaction mixture and stirred at room temperature for 2 hrs. The reaction mixture was concentrated, and purified on HPLC (C-18 prep column, 10% to 90% acetonitrile in water both containing 0.1% TFA) to give 2.6 g (53%) of the title compound; ESMS, (M+1), 379.

Example 9

Butyl 3-{[2-(Acetylamino)ethylthio]methyl}-4-oxo-4-(3-pyridylbutanoate

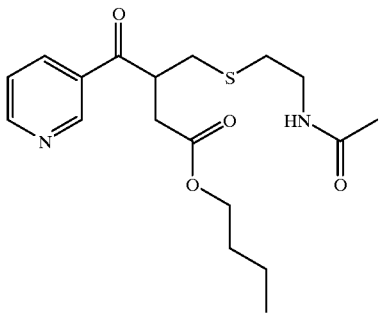

A solution of butyl 4-oxo-4-(3-pyridyl)butanoate (6.0 g), 37% formaldehyde in water (2.06 g) and piperidine (2.17 g) in ethanol (25 mL) was heated at 80° C. for 2 hrs. N-Acetylcysteamine (3.03 g) was added to the reaction mixture. The reaction mixture was heated at 80° C. with stirring for 3 hrs. The solution was concentrated and purified on HPLC (C-18 prep column, 10% to 90% acetonitrile in water both containing 0.1% TFA) to give 5.60 g of the title compound; ESMS (M+1)$^+$367.

Example 10

3-([2-(Acetylamino)ethylthio]methyl)-N,N-dimethyl-4-oxo-4-(3-pyridyl)butanamide

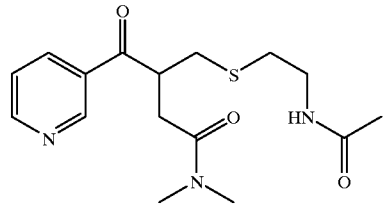

Ethyl chloroformate (3.85g) was added to a solution of 3-{[2-(acetylamino)-ethylthio]methyl-4-oxo-4-(3-pyridyl)-butanoic acid (10 g) and triethylamine (4.88 g) in tetrahydrofuran (THF, 150 mL) at 0° C. The reaction mixture was stirred for 5 min. A 2M solution of dimethylamine in THF (17.7 mL) was added to the reaction mixture and stirred at room temperature for 2 hrs. The reaction mixture was concentrated and purified on HPLC (C-18 prep column, 10% to 90% acetonitrile in water both containing 0.1% TFA) to give 5.1 g of the title compound; ESMS (M+1)$^+$338.

Example 11

2-[(2-Aminoethylthio)methyl]-4-piperidyl-1-(3-pyridyl)butane-1,4-dione

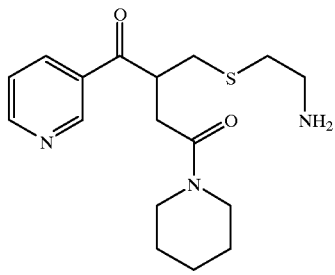

Ethyl chloroformate (8.07 g) was added over 10 min to a solution of 4-oxo-4-(3-pyridyl)butanoic acid (11.1 g) and triethylamine (7.5 g) in dichloromethane (300 mL) at 0° C. with constant stirring. Piperidine (5.27 g) was added to the reaction mixture and stirred at room temperature for 1h. The reaction mixture was washed with water and the organic layer was concentrated to an oil. The oil was dissolved in ethanol (80 mL), 37% aqueous formaldehyde (6.85 g) and piperidine (6.85 g). The reaction mixture was heated at 80° C. for 3 h. (tert-Butoxy)-N-(2-sulfanylethyl)carboxamide (10.97 g) was added to the reaction mixture and stirred at 80° C. for 2 h. The reaction mixture was concentrated and purified by flash chromatography (50% ethyl acetate in hexanes to 100% ethyl acetate) to give (tert-butoxy)-N-{2-[4-oxo-4-piperidyl-2-( 3-pyridylcarbonyl)butylthio] ethyl}carboxamide. This compound was dissolved in dioxane (80 mL) and treated with 4N HCl/dioxane (60 mL) for 30 min. at r.t. The reaction mixture was concentrated to give 63% yield of the title compound as hydrochloride salt; ESMS (M+1)$^+$336.

Example 12

2-Amino-N-{2-[4-oxo-4-piperidyl-2-(3-pyridylcarbonyl)-butylthio]-ethyl}acetamide

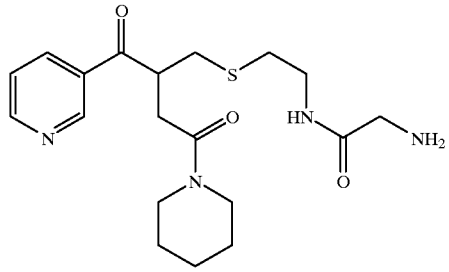

Ethyl chloroformate (2.93 g) was added to a solution of 2-[(tert-butoxy)-carbonylamino]acetic acid (4.73 g) and triethylamine (4.09 g) in dichloromethane (150 mL) at 0° C. The solution was stirred for 20 min. and 2-[(2-aminoethylthio)methyl]-4-piperidyl-1-(3-pyridyl)butane-1, 4-dione (10 g), triethylamine (4.1 g) and dichloromethane (150 mL) were added to the reaction mixture and stirred at room temperature for 1 h. The reaction mixture was washed with water, concentrated under reduced pressure and purified on flash chromatography (50% ethyl acetate in hexanes to 100% ethyl acetate) to give 35% of 2-[(tert-butoxy) carbonylamino]-N-{2-[4-oxo-4-piperidyl-2-(3-pyridylcarbonyl)butylthio]ethyl}acetamide. This intermediate (4.22 g) was treated with 4N HCl/dioxane (15 mL) in dioxane (25 mL) for 30 min. The solution was purified on preparative HPLC (C-18 prep column, 10% to 90% acetonitrile in water) to give 2.8 g of the title compound, ESMS, (M+1)$^+$393.

Example 13

Methyl 3-{[(N-Methylcarbamoyl)methylthio]methyl}-4-oxo-4-(3-pyridyl)butanoate

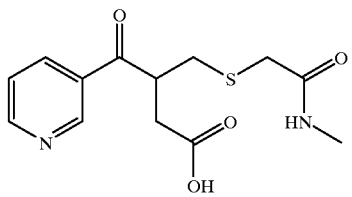

A solution of methyl 3-(3-pyridylcarbonyl)but-3-enoate in dichloromethane (0.5 mL, 0.1 mM), triethylamine in dichloromethane (0.5 mL, 0.1 mM) and N-methyl-2-sulfanylacetamide (0.6 mL, 0.12 mmol) was stirred for 24 h. PS isocyanate resin (60 mg) was added to the reaction mixture and stirred for 24 h. The solution was filtered and concentrated to give the title compound in quantitative yield, ESMS, (M+1)$^+$311.

Example 14

Methyl 3-{[2-(Acetylamino)ethylthio]methyl}-4-oxo-4-(3-pyridyl)butanoate

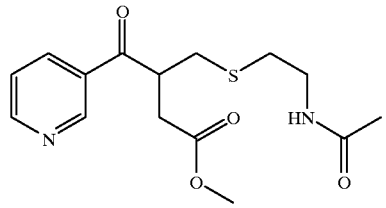

The title compound was prepared from methyl 3-(3-pyridylcarbonyl)but-3-enoate and N-(2-sulfanylethyl)acetamide as described in Example 13 in quantitative yield, ESMS, (M+1)$^+$325.

Example 15

Methyl 3-({2-[3-(Acetylamino)propanoylamino]ethylthio}-methyl)-4-oxo-4-(3-pyridyl)butanoate

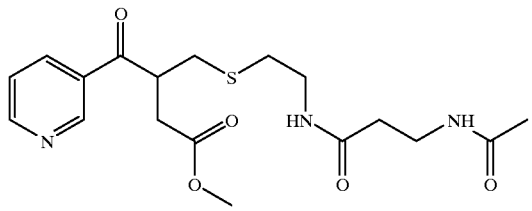

A solution of methyl 3-[(2-aminoethylthio)methyl]-4-oxo-4-(3-pyridyl)butanoate (747 mg), 3-(acetylamino)propanoic acid (302 mg), dicyclohexylcarbodiimide (433 mg), 1-hydroxybenzotriazole (567 mg) and N-methylmorpholine (402 mg) in dichloromethane (10 mL) were stirred at room temperature overnight. The solution was concentrated and purified by flash chromatography (SiO2, chloroform:methanol=9:1) to give the title compound in 75% yield; ESMS (M+1)$^+$353.

Example 16

3-[((2R)-2-{[(4—Chlorophenyl)amino]carbonylamino}-2-(methoxycarbonyl)ethylthio)methyl]-4-oxo-4-(3-pyridyl)butanoic Acid

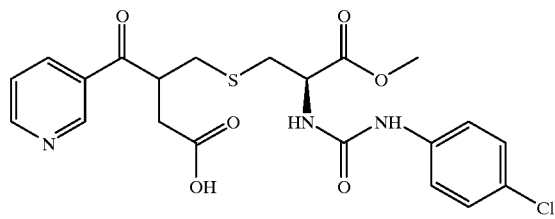

Wang resin (100–200 mesh, 0.66 mmol/g, 70 mg) was treated with triphenylphosphine (34.5 mg), diethyl azodicarboxylate (20.8 μL) and 3-({(2R)-2-[(fluoren-9-ylmethoxy)carbonylamino]-2-(methoxycarbonyl)ethylthio}methyl)-4-oxo-4-( 3-pyridyl)butanoic acid (72.3 mg) in THF (0.5 mL) at room temperature for 3 days. The resin was filtered, washed with dimethyl formamide, isopropanol, dichloromethane and ether and dried. The resin was treated with 20% piperidine-dichloromethane (1 mL) solution for 1 h. The resin was filtered, and washed with dimethyl formamide, isopropanol, dichloromethane and ether and dried. The resin was treated with 10 eq of 4-chlorophenyl isocyanate in dichloromethane (6 mL) for two days. The resin was washed with washed with dimethyl formamide, isopropanol, dichloromethane and ether and dried. The resin was treated with 20% trifluoroacetic acid in dichloromethane (5 mL). The solution was filtered, concentrated and purified on HPLC (C-18 prep column, 10% to 90% acetonitrile in water both containing 0.1% TFA) to give 12% of the title compound; ESMS, (M+1)$^+$480.

Example 17

3-[((2R)-2-{[(2-Fluorophenyl)amino]carbonylamino}-2-(methoxycarbonyl)ethylthio)methyl]-4-oxo-4-(3-pyridyl)butanoic Acid

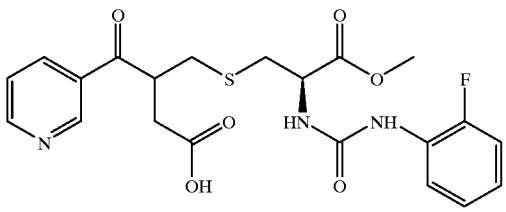

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and 2-fluorophenyl isocyanate as described in Example 16 in a 13% yield; ESMS, (M+1)$^+$464.

Example 18

3-[((2R)-2-{[(4-Fluorophenyl)amino]carbonylamino}-2-(methoxycarbonyl)ethylthio)methyl]-4-oxo-4-(3-pyridyl)butanoic Acid

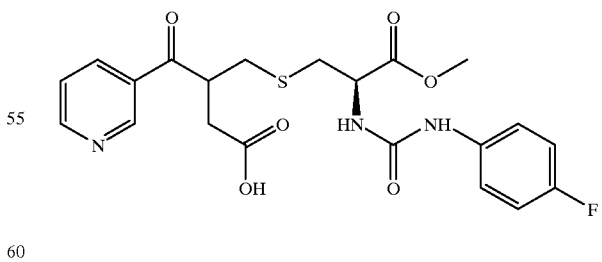

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and 4-fluorophenyl isocyanate as described in Example 16 in a 5% yield; ESMS, (M+1)$^+$464.

Example 19

3-[((2R)-2-{[(3,5-Dimethylphenyl)amino]carbonylamino}-2-(methoxycarbonyl)ethylthio)methyl]-4-oxo-4-(3-pyridyl)butanoic Acid

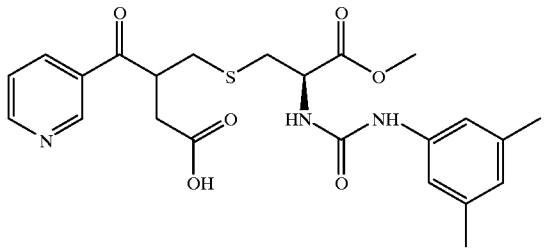

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and 3,5-dimethylphenyl isocyanate as described in Example 16 in a 2.4% yield; ESMS, (M+1)+ 474.

Example 20

3-[((2R)-2-{[(2-Methoxyphenyl)amino]carbonylamino}-2-(methoxycarbonyl)ethylthio)methyl]-4-oxo-4-(3-pyridyl)butanoic Acid

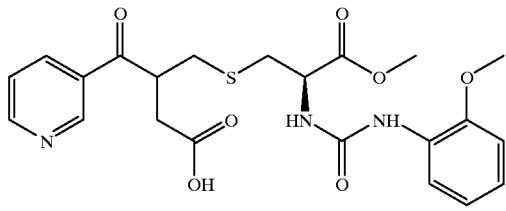

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and 2-methoxyphenyl isocyanate as described in Example 16 in a 14% yield; ESMS, (M+1)+476.

Example 21

3-[((2R)-2-{[(3,4,5-Trimethoxyphenyl)amino]carbonylamino}-2-(methoxycarbonyl)ethylthio)methyl]-4-oxo-4-(3-pyridyl)butanoic Acid

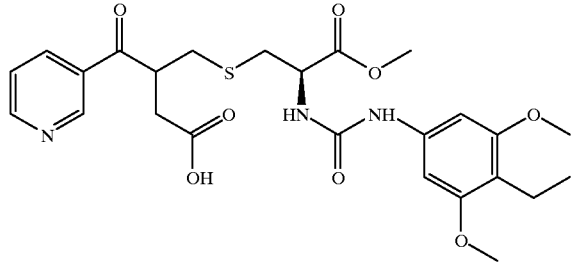

The title compound was prepared from 3-({(2R)-2-[(fluoren-9-ylmethoxy)carbonylamino]-2-(methoxycarbonyl)ethylthio}methyl)-4-oxo-4-( 3-pyridyl) butanoic acid and 3,4,5-trimethoxyphenyl isocyanate as described in Example 16 in a 7.2% yield; ESMS, (M+1)+ 536.

Example 22

3-({(2R)-2-(Methoxycarbonyl)-2-[(naphthylamino)carbonylamino]ethylthio)}methyl)-4-oxo-4-(3-pyridyl)butanoic Acid

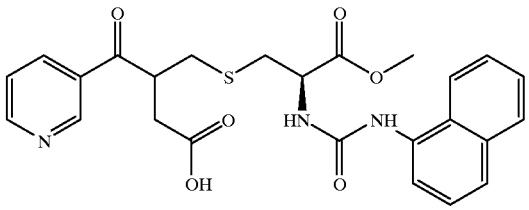

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and 1-naphthyl isocyanate as described in Example 16 in a 12% yield; ESMS, (M+1)+496.

Example 23

3-({(2R)-2-(Methoxycarbonyl)-2-[(phenylmethoxy)carbonylamino]ethylthio}methyl)-4-oxo-4-(3-pyridyl)butanoic Acid

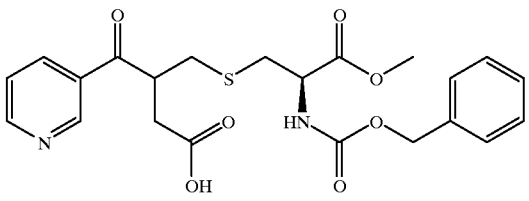

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and benzyl chloroformate as described in Example 16 at 12% yield; ESMS, (M+1)+460.

Example 24

3-({(2R)-2-(Methoxycarbonyl)-2-[(prop-2-enylamino)carbonylamino]ethylthio}methyl)-4-oxo-4-(3-pyridyl)butanoic Acid

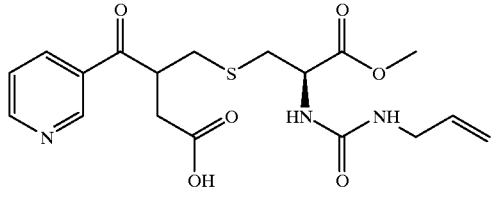

The title compound was prepared from 3-({(2R)-2-[(fluoren-9-ylmethoxy)carbonylamino-2-(methoxycarbonyl)ethylthio}methyl)-4-oxo-4-(3-pyridyl)butanoic acid and allyl isocyanate as described in Example 23 to provide the desired compound in a 10.4% yield; ESMS, (M+1)+410.

Example 25

3({(2R)-2-[(Cyclohexylamino)carbonylamino]-2-(methoxycarbonyl)ethylthio}methyl)-4-oxo-4-(3-pyridyl)butanoic Acid

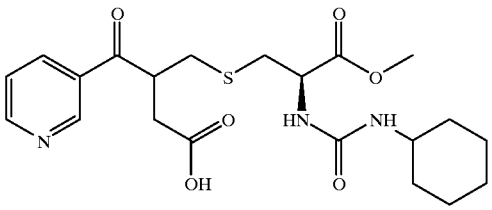

The title compound was prepared from 3-({(2R)-2-[(fluoren-9-ylmethoxy)carbonylamino]-2-(methoxycarbonyl)ethylthio}methyl)-4-oxo-4-(3-pyridyl)butanoic acid and cyclohexyl isocyanate as described in Example 16 in a 6% yield; ESMS, (M+1)$^+$452.

Example 26

Propyl 3-{[2-(Acetylamino)ethylthio]methyl}-4-oxo-4-(3-pyridyl)butanoate

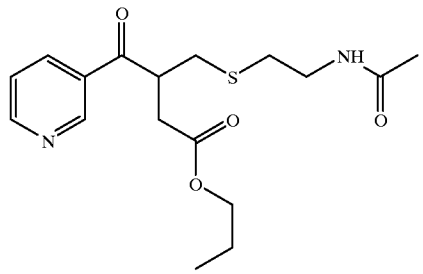

A solution of 3-{[2-(acetylamino)ethylthio]methyl}-4-oxo-4-(3-pyridyl)butanoic acid (0.1 g), 1[3-(dimethylamino)propyl]-3-ethylcarbodiimide hydrochloride (68.1 mg) and 4-dimethylaminopyridine (0.1 eq) in dimethyl formamide (2 mL) was stirred for 24 h. The solution was purified on preparative HPLC (C-18 prep column, 10% to 90% acetonitrile in water both containing 0.1% TFA) to give 0.085 g (75%) of the title compound; ESMS (M+1)$^+$353.

Example 27

Indanyl 3-{[2-(Acetylamino)ethylthio]methyl}-4-oxo-4-(3-pyridyl)butanoate

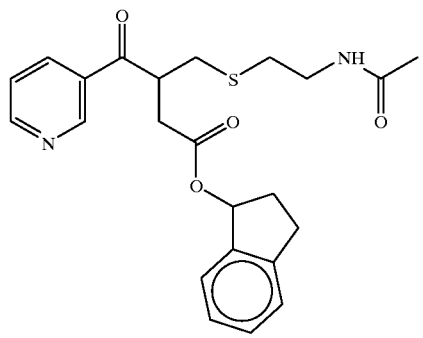

The title compound was prepared from 3-{[2-(acetylamino)ethylthio]methyl}-4-oxo-4-(3-pyridyl)butanoic acid and indanol as described in the above Example 26 in 55% yield; ESMS (M+1$^+$) 427.

Example 28

3-(3-Pyridyl)propyl 3-{[2-(acetylamino)ethylthio]methyl}-4-oxo-4-(3-pyridyl)butanoate

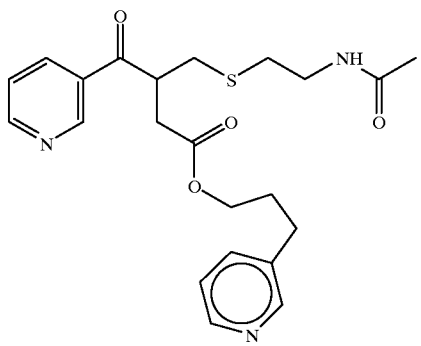

The title compound was prepared from 3-{[2-(acetylamino)ethylthio]methyl}-4-oxo-4-(3-pyridyl)butanoic acid and 3-(3-pyridyl)propan-1-ol as described in the above Example 26 in 65% yield; ESMS (M+1$^+$) 430.

Example 29

2-Piperidylethyl 3-{[2-(acetylamino)ethylthio]methyl}-4-oxo-4-(3-pyridyl)butanoate

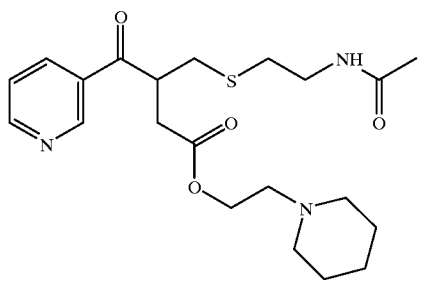

The title compound was prepared from 3-{[2-(acetylamino)ethylthio]Methyl}-4-oxo-4-(3-pyridyl)butanoic acid and 3-(3-pyridyl)propan-1-ol as described in the above Example 26 in 35% yield; ESMS (M+1$^+$) 422.

Example 30

Ethyl 3-{[(2R)-2-(Acethylamino)-2-(ethoxycarbonyl)ethylthio]methyl}-4-oxo-(3-pyridyl)butanoate

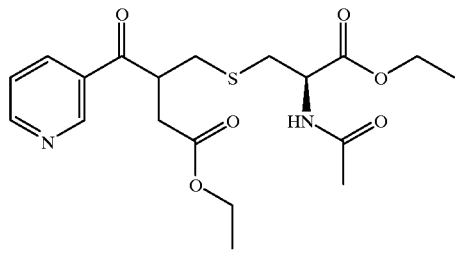

A solution of ethyl 4-oxo-4-(3-pyridyl)butanoate (0.30 g), piperidine (0.15 g) and 37% aqueous formaldehyde (0.14 g) in ethanol (2 mL) was stirred at 90° C. for 2 h. A solution of ethyl (2R)-2(acetylamino)-3-sulfanylpropanoate (0.28 g) in ethanol (5 mL) was added to the reaction mixture and heated at 80° C. for 3 h. The reaction mixture was concentrated and purified on preparative HPLC (C-18 prep column, 10% to 90% acetonitrile in water both containing 0.1% TFA) to give 0.19 g of the title compound; ESMS (M+1)$^+$411.

Example 31

Methyl 3-({(2R)-2-(Methoxycarbonyl)-2-[(methylethoxy)carbonylamino]-ethylthio}methyl-4-oxo-4-(3-pyridyl)butanoate

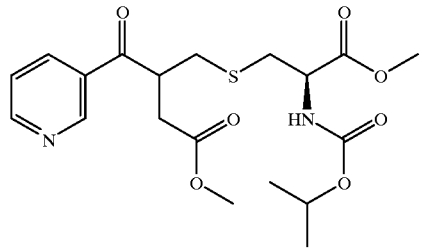

A solution of 3-({(2R)-2-(methoxycarbonyl)-2-{(methylethoxy) carbonylamino]-ethylthio}methyl)-4-oxo-4-(3-pyridyl)butanoic acid (15 mg), triethylamine (35 μL) and trimethylsilyl diazomethane (10 eq) in dichloromethane (1 mL) and dimethyl formamide (1 mL) was stirred at room temperature overnight. The reaction mixture was concentrated and purified on preparative HPLC (C-18 prep column, 10% to 90% acetonitrile in water both containing 0.1% TFA) to give 6.7 mg of the title compound; ESMS (M+1)$^+$427.

Example 32

Methyl 3-({(2R)-2-(Methoxycarbonyl)-2-[(prop-2-enyloxycarbonylamino]-ethylthio}methyl)-4-oxo-4-(3-pyridyl)butanoate

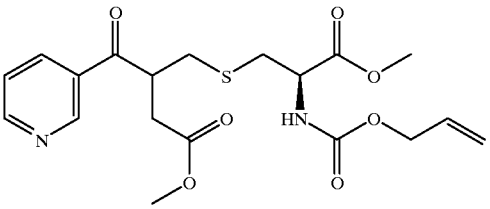

The title compound was prepared from 1{[2-(butylamino)ethylthio]methyl}-4-oxo-4-(3-pyridyl)butanoic acid and trimethylsilyl diazomethane as described in the above Example 31 in 55% yield; ESMS (M+1$^+$) 425.

Example 33

3-{[2-(N-Cyclohexylacetylamino)ethylthio]methyl}-N,N-dimethyl-4-oxo-4-(3-pyridyl)butanamide

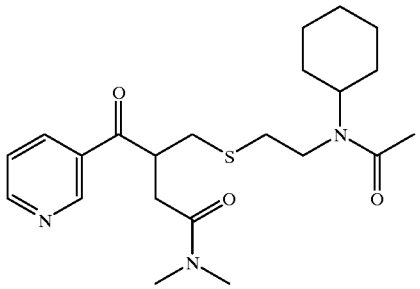

Triethylamine (14.7 tL) was added to a solution of 3-{[2-(N-cyclohexylacetylamino)ethylthio]methyl}-4-oxo-4-(3-pyridyl)butanoic acid (44.6 mg) in dichloromethane (1.1 mL) and stirred for 30 min. The solution was cooled to 0° C. and ethyl chloroformate (10.5 μL) was added and stirred for 10 minutes. Dimethylamine in tetrahydrofuran (2M, 53 μL) was added and stirred at room temperature overnight. The solution was concentrated and purified on preparative HPLC (C-18 prep column, 10% to 90% acetonitrile in water both containing 0.1% TFA) to give 6.8 mg of the title compound; ESMS (M+1)$^+$420.

Example 34

Ethyl 3-{[2-(N-Cyclohexylmorpholin-4-ylcarbonylamino)ethylthio]methyl}-4-oxo-4-(3-pyridyl)butanoate

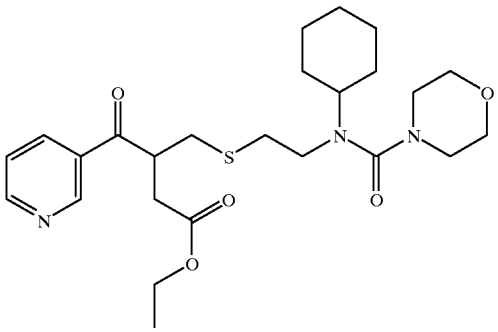

A solution of ethyl 3-{[2-(cyclohexylamino)ethylthio]methyl}-4-oxo-4-(3-pyridyl)butanoate (47.2 mg) and triethylamine (17.4 AL) in dichloromethane (1.3 mL) was treated with morpholine-4-carbony chloride (14.9 µL) at room temperature for 1 h. The solution was concentrated and purified on preparative HPLC (C-18 prep column, 10% to 90% acetonitrile in water both containing 0.1 % TFA) to give 11 mg of the tile compound; ESMS (M+1)⁺493.

Example 35

Ethyl 3-({2-[3,-Difluorophenyl)-N-Butylcarbonylamino]ethylthio}methyl)-4-oxo-4-(3-pyridyl)butanoate

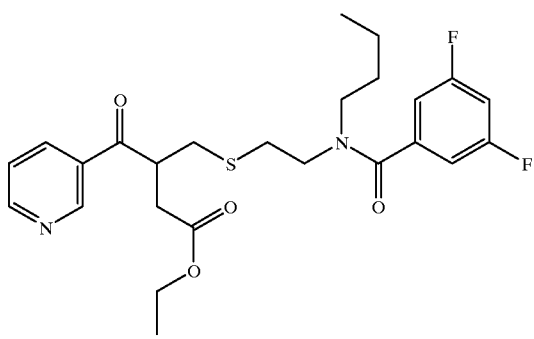

A solution of ethyl 3 {[2-(butylamino)ethylthio]methyl}-4-oxo-4-(3-pyridyl)butanoate (100 mg), 3,5-difluorobenzoyl chloride (50 mg) and triethylamine (28 mg) in dichloromethane (3 mL) was stirred at room temperature overnight. The solution was concentrated and purified on preparative HPLC (C-18 prep column, 10% to 90% acetonitrile in water both containing 0. 1% TFA) to give 57 mg of the title compound; ESMS (M+1)⁺493.

Example 36

Ethyl 3-{[2-N-Butylacetamino)ethylthio]methyl}-4-oxo-4-(3-pyridyl)butanoate

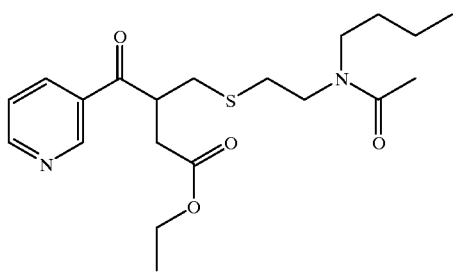

The title compound was prepared from ethyl 3 {[2-(butylamino) ethylthio]methyl}-4-oxo-4-(3-pyridyl)butanoate and acetyl chloride as described in the above Example 35 in 49% yield; ESMS (M+1⁺) 394.

Example 37

Ethyl 3-({2-[N-Butyl(4-cyanophenyl)carbonylamino]ethylthio}methyl)-4-oxo-4-(3-pyridyl)butanoate

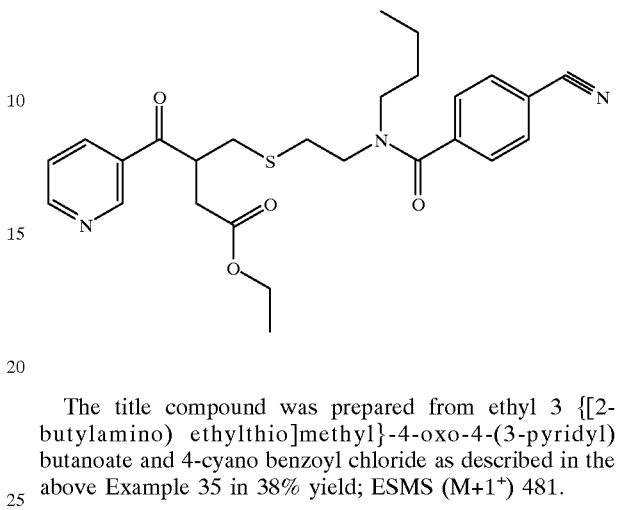

The title compound was prepared from ethyl 3 {[2-butylamino) ethylthio]methyl}-4-oxo-4-(3-pyridyl)butanoate and 4-cyano benzoyl chloride as described in the above Example 35 in 38% yield; ESMS (M+1⁺) 481.

Example 38

Ethyl 3-{[2-(N-Butyl-3-cyclopentylpropanoylamino)ethylthio]methyl}-4-oxo-4-(3-pyridyl)butanoate

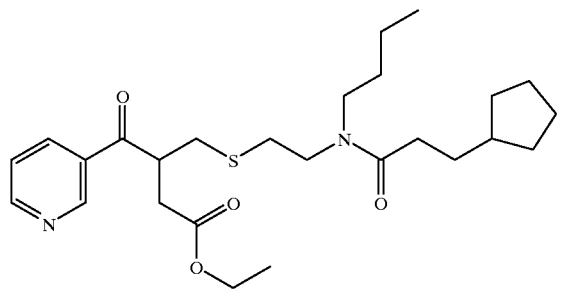

The title compound was prepared from ethyl 31}[2-(butylamino)ethylthio] methyl)-4-oxo-4-(3-pyridyl)butanoate and cyclopentylpropionyl chloride as described in the above Example 35 in 35% yield; ESMS (M+1⁺) 477.

Example 39

Ethyl 3-({2-[N-Butyl(cyclohexylamino)carbonylamino]ethylthio}methyl)-4-oxo-4-(3-pyridyl)butanoate

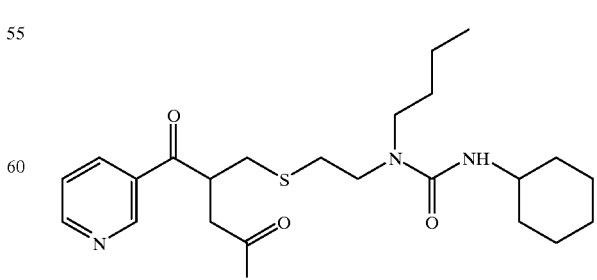

The title compound was prepared from ethyl 3 {[2-(butylamino)ethylthio] methyl}-4-oxo-4-(3-pyridyl)butanoate and cyclohexylisocyanate as described in the above Example 35 in 48% yield; ESMS (M+1⁺) 478.

Example 40

Ethyl 3-[(2-{N-Butyl(4-methylphenyl)amino]carbonylamino}ethylthio)methyl)-4-oxo-4-(3-pyridyl)butanoate

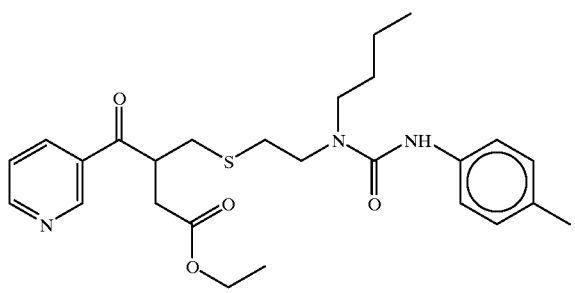

The title compound was prepared from ethyl 3{[2-(butylamino)ethylthio]methyl}-4-oxo-4-(3-pyridyl)butanoate and 4-methylphenyl isocyanate as described in the above Example 35 in 48% yield; ESMS (M+1⁺) 486.

Example 41

Methyl 3-{[(2R)-2-({[2-(Acetylamino)-4-methyl(1,3-thiazol-5-YL)]sulfonyl}amino-2-(methoxycarbonyl)ethylthio]methyl}-4-oxo-4-(3-pyridyl)butanoate

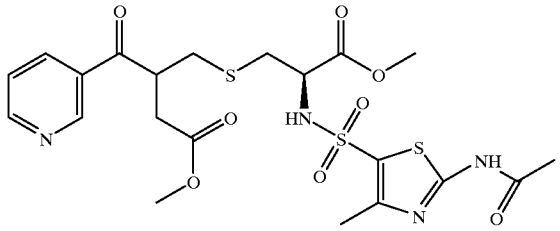

A solution of methyl 3-{[(2R)-2-amino-2-(methoxycarbonyl)ethylthio]methyl}-4-oxo-4-(3-pyridyl)butanoate hydrochloride (20.7 mg), N-[5-(chlorosulfonyl)-4-methyl-1,3-thiazol-2-yl]acetamide (1.5 eq) and triethylamine (1.5 eq) in dichloromethane (1 mL) was stirred at room temperature overnight. The solution was concentrated and purified on preparative HPLC (C-18 prep column, 10% to 90% acetonitrile in water both containing 0.1% TFA) to give 19.1 mg of the title compound; ESMS (M+1)⁺560.

Example 42

3-{[(2-(N-Cyclohexylacetylamino)ethylthio]methyl}N,N-diethyl-4-oxo-4-4(3-pyridyl)butanamide

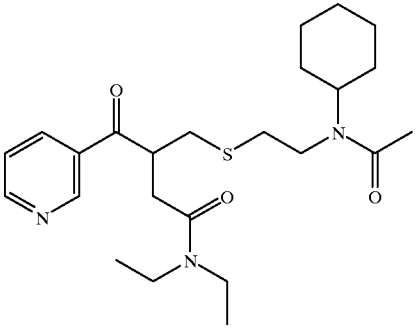

A solution of 3-{[(2-(N-cyclohexylacetylamino)ethylthio]methyl}-4-oxo-4-(3-pyridyl)butanoic acid (49 mg), triethylamine (13 mg), ethyl chloroformate (14 mg) in dichloromethane (1 mL) were stirred at room temperature under anhydrous conditions for 15 min. Diethylamine (9 mg) was added and the reaction mixture was stirred overnight. The solution was concentrated and purified on preparative HPLC (C-18 prep column, 10% to 90% acetonitrile in water both containing 0.1% TFA) to give 49 mg of the title compound; ESMS (M+1)⁺448.

Example 43

(4-Fluorophenyl)-N-{2-[4-oxo-4-piperidyl-2-(3-pyridylcarbonyl)butylthio]ethyl}carboxamide A solution of ethyl 3-({2-[(4-fluorophenyl)carbonylamino]ethylthio}methyl)-4-oxo-4-(3-pyridyl)butanoate (100 mg) and lithium hydroxide (1 eq) was stirred a temperature in ethanol-water (1:1, 2 mL) till the starting material disappeared. The solution was acidified and purified on preparative HPLC (C-18 prep column, 10% to 90% acetonitrile in water both containing 0.1% TFA) to give 91 mg of 3-({2-[(4-fluorophenyl)carbonylamino]ethylthio}methyl)-4-oxo-4-(3-pyridyl)butanoic acid. The acid (91 mg) was treated with ethyl chloroformate (1.1 eq) and triethylamine (1.1 eq) in tetrahydrofuran (2.5 mL) at room temperature for 10 minutes. Piperidine (1.1 eq) was added to the reaction mixture and stirred at room temperature overnight. The solution was concentrated and purified on preparative HPLC (C-18 prep column, 10% to 90% acetonitrile in water both containing 0.1% TFA) to give 66 mg the title compound; ESMS (M+1)⁺458.

Example 44

[(4-Fluorophenyl)-amino]-N-{2-[4-oxo-4-piperidyl-2-(3-pyridylcarbonyl)butylthio]ethyl}carboxamide

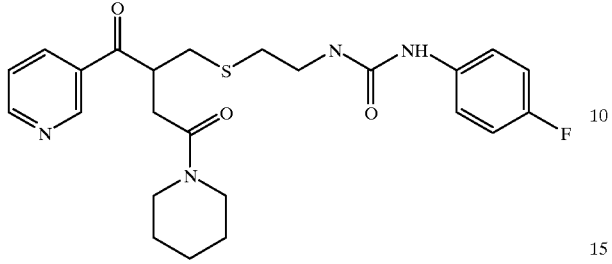

The title compound was prepared from ethyl 3-[({2-{[(4-fluorophenyl)amino]carbonylamino}ethylthio)methyl]-4-oxo-4-(3-pyridyl)butanoate and piperidine as described in the above Example 43 in 29% yield; ESMS (M+1$^+$) 472.

Example 45

4-{2-[4-oxo-4-piperidyl-2-(3-pyridylcarbonyl)-butylthio]ethyl}-acetamide in pure cristal from

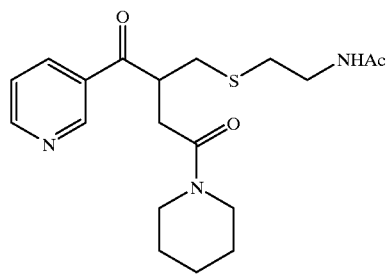

in pure crystal form

Piperidine (41.0 ml), 1-hydroxybenzotriazole hydrate (55.7 g, 0.41 mol) and 1-[3-(dimethylamino)propyl]-3-ethylcarbodiimide hydrochloride (79.0 g, 0.41 mol) were added to a mixture of 3-{[2-(acetylamino)ethylthio]}methyl-4-oxo-4-(3-pyridyl)butanoic acid (116.3 g, 0.37 mol) in tetrahydrofuran (1500 ml) at room temperature. After being stirred for 2 h, the reaction mixture was filtered by Celite and the filtrate was evaporated. The residue was poured into H$_2$O (900 ml) and extracted with AcOEt (700 ml) three times. After the organic layer was washed with sat. NaHCO$_3$ (900 ml), the solvent was dried over MgSO$_4$ and evaporated to give the title compound (118.7 g, 85%) as a yellow oil. The crude yellow oil (79.6 g, 0.21 mol) was dissolved with AcOEt (350 ml) and the mixture was stirred vigorously at room temperature. After being stirred for 12 h, separated crystals were collected. The crystals were recrystallized from AcOEt (350 ml) to give the title compound (67.1 g, 84%) as an off white solid of mp 86–90° C. Anal. Calcd for C$_{19}$H$_{27}$N$_3$O$_3$S: C, 60.45; H, 7.21; N, 11.13. Found: C, 60.36; H, 7.02; N, 11.08. $^1$H-NMR(CD$_3$OD) ppm: 1.42–1.52 (2H, m), 1.56–1.70 (4H, m), 1.90 (3H, s), 2.60 (2H, t, J=7 Hz), 2.73 (1H, dd, J=7 and 13 Hz), 2.81–2.91 (2H, m), 3.08 (1H, dd, J=10 and 16 Hz), 3.26–3.32 (2H, m), 3.41 (2H, t, J=5 Hz), 3.46–3.53 (2H, m), 4.16 (1H, m), 7.58 (1H, ddd, J=1, 5 and 8 Hz), 8.44 (1H, dt, J=2 and 8 Hz), 8.73 (1H, dd, J=2 and 5 Hz), 9.15 (1H, dd, J=1 and 2 Hz).

Example 46

4-{2-[4-Oxo-4-piperidyl-2-(3-pyridylcarbonyl)-butylthio]ethyl}-acetamide 2 Maleate

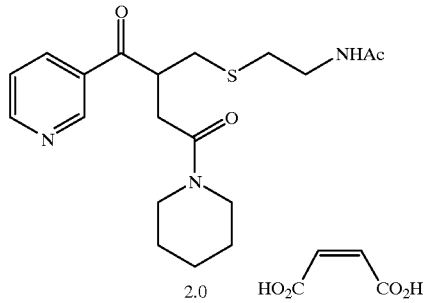

A solution of maleic acid (88.7 g, 0.765 mol) in acetone (700 ml) was added to a solution of 4-{2-[4-oxo-4-piperidyl-2-(3-pyridylcarbonyl)-butylthio]ethyl}-acetamide (96.2 g, 0.255 mol) in acetone (600 ml) at room temperature. After the mixture was stood for overnight, the crystals were collected to give the title compound (142.5 g, 92%) as a white solid of mp 115–117° C. Anal. Calcd for C$_{23}$H$_{31}$N$_3$O$_7$S: C, 53.19; H, 5.79; N, 6.89. Found: C, 53.17; H, 5.63; N, 6.89. $^1$H-NMR(CD$_3$OD) ppm: 1.42–1.51 (2H, m), 1.56–1.70 (4H, m), 1.90 (3H, s), 2.60 (2H, t, J=7 Hz), 2.75 (1H, dd, J=7 and 13 Hz), 2.81–2.94 (2H, m), 3.10 (1H, dd, J=10 and 16 Hz), 3.25–3.32 (2H, m), 3.41 (2H, t, J=6 Hz), 3.47–3.53 (2H, m), 4.17 (1H, m), 6.31 (4H, s), 7.73 (1H, ddd, J=1, 5 and 8 Hz), 8.58 (1H, dt, J=2 and 8 Hz), 8.78 (1H, dd, J=2 and 5 Hz), 9.21 (1H, dd, J=1 and 2 Hz).

Example 47

4-{2-[4-Oxo-4-piperidyl-2-(3-pyridylcarbonyl)-butylthio]ethyl}-acetamide 1.5 Maleate

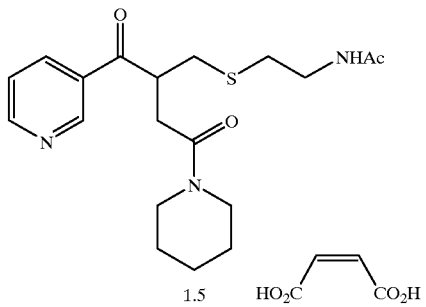

A solution of maleic acid (116 mg, 1 mmol) in acetone (2 ml) was added to a solution of 4-{2-[4-oxo-4-piperidyl-2-(3-pyridylcarbonyl)-butylthio]ethyl}-acetamide (377 mg, 1 mmol) in acetone (2 ml) at room temperature. After the mixture was stood for overnight, the crystals were collected to give the title compound (208 mg, 61%) as a white solid of mp 113–115° C. Anal. Calcd for C$_{50}$H$_{66}$N$_6$O$_{18}$S$_2$: C, 54.44; H, 6.03; N, 7.62. Found: C, 54.18; H, 5.97; N, 7.54. $^1$H-NMR(CD$_3$OD) ppm: 1.42–1.5.1 (2H, m), 1.56–1.70 (4H, m), 1.90 (3H, s), 2.60 (2H, t, J=7 Hz), 2.74 (1H, dd, J=7 and 13 Hz), 2.81–2.94 (2H, m), 3.10 (1H, dd, J=10 and 16 Hz), 3.25–3.34 (2H, m), 3.41 (2H, t, J=6 Hz), 3.47–3.54 (2H, m), 4.17 (1H, m), 6.31 (3H, s), 7.69 (1H, ddd, J=1, 5 and 8 Hz), 8.58 (1H, dt, J=2 and 8 Hz), 8.78 (1H, dd, J=2 and 5 Hz), 9.21 (1H, dd, J=1 and 2 Hz).

Example 48

4-{2-[4-Oxo-4-piperidyl-2-(3-pyridylcarbonyl)-butylthio]ethyl}-acetamide 2-Hydroxy-1-naphthoate

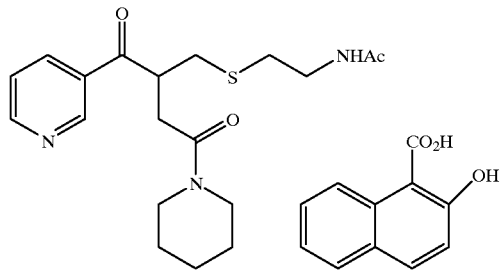

2-Hydroxy-1-naphthoic acid (376 mg, 2 mmol) was added to a solution of 4-{2-[4-oxo-4-piperidyl-2-(3-pyridylcarbonyl)-butylthio]ethyl}-acetamide (754 mg, 2 mmol) in EtOH (2 ml) at room temperature. After the mixture was stood for overnight, the crystals were collected and recrystallized from (acetone-hexane) to give the title compound (896 mg, 79%) as a white solid of mp 105–107° C. Anal. Calcd for $C_{30}H_{35}N_3O_6S$: C, 63.70; H, 6.24; N, 7.43. Found: C, 63.40; H, 6.06; N, 7.33. $^1$H-NMR(CD$_3$OD) ppm: 1.42–1.52 (2H, m), 1.56–1.70 (4H, m), 1.90 (3H, s), 2.60 (2H, t, J=7 Hz), 2.72 (1H, dd, J=7 and 13 Hz), 2.80–2.91 (2H, m), 3.09 (1H, dd, J=10 and 16 Hz), 3.27–3.33 (2H, m), 3.41 (2H, t, m), J=5 Hz), 3.46–3.53 (2H, m), 4.16 (1H, m), 7.12 (1H, d, J=9 Hz), 7.32 (1H, m), 7.53 (1H, m), 7.59 (1H, ddd, J=1, 5 and 8 Hz), 7.78 (1H, d, J=8 Hz), 7.94 (1H, d, J=9 Hz), 8.12 (1H, br s), 8.45 (1H, dt, J=2 and 8 Hz), 8.73 (1H, dd, J=2 and 5 Hz), 8.88 (1H, d, J=9 Hz), 9.15 (1H, d, J=2Hz).

Example 49

4-{2-[4-Oxo-4-piperidyl-2-(3-pyridylcarbonyl)-butylthio]ethyl}-acetamide Oxalate

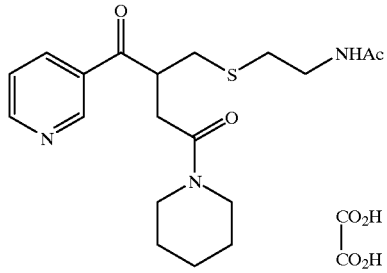

A solution of oxalic acid (87 mg, 0.97 mmol) in acetone (1 ml) was added to a solution of 4-{2-[4-oxo-4-piperidyl-2-(3-pyridylcarbonyl)-butylthio]ethyl}-acetamide (366 mg, 0.97 mmol) in acetone (2 ml) at room temperature. After the mixture was stood for overnight, the crystals were collected to give the title compound (345 mg, 74%) as a white solid of mp 129–130° C. Anal. Calcd for $C_{21}H_{29}N_3O_7S$: C, 53.95; H, 6.25; N, 8.99. Found: C, 53.97; H, 6.34; N, 8.88. $^1$H-NMR(CD$_3$OD) ppm: 1.42–1.52 (2H, m), 1.56–1.70 (4H, m), 1.90 (3H, s), 2.60 (2H, t, J=7 Hz), 2.73 (1H, dd, J=7 and 13 Hz), 2.81–2.93 (2H, m), 3.08 (1H, dd, J=10 and 16 Hz), 3.26–3.33 (2H, m), 3.42 (2H, t, J=5 Hz), 3.46–3.53 (2H m), 4.16 (1H, m), 7.67 (1H, ddd, J=1, 5 and 8 Hz), 8.54 (1H, dt, J=2 and 8 Hz 8.78 (1H dd, J=2 and 5 Hz), 9.20 (1H, dd, J=1 and 2 Hz).

Example 50
Representative Compounds

By the procedures set forth herein, the compounds identified in Tables 1 and 2 were made, wherein $R_1$, $R_2$, $R_3$, $R_4$ and $R_5$ are as identified below.

TABLE 1

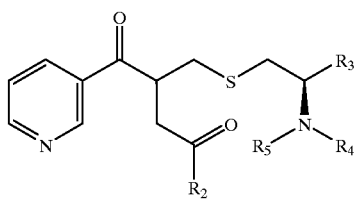

| No. | $R_2$ | $R_3$ | $R_4$ | $R_5$ | MW (M$^+$) |
|---|---|---|---|---|---|
| 1 | $X_2$–O–CH$_3$ | H | $X_4$–CH$_2$CH$_2$–CH$_3$ | H | 338 |
| 2 | $X_2$–O–CH$_3$ | H | $X_4$–CH$_3$ | CH$_3$, $X_5$ | 310 |
| 3 | $X_2$–O–CH$_3$ | $X_3$–C(O)OH | $X_4$–C(O)–CH$_3$ | H | 396 |
| 4 | $X_2$–O–CH$_3$ | H | $X_4$–C(O)–O–C(CH$_3$)$_2$–CH$_3$ (H$_3$C) | H | 382 |

TABLE 1-continued
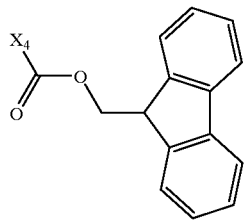
| No. | R₂ | R₃ | R₄ | R₅ | MW (M⁺) |
|---|---|---|---|---|---|
| 5 | $X_2$-O-CH₃ | $X_3$-C(=O)- | $X_4$-CH₃ | H | 310 |
| 6 | $X_2$-O-CH₃ | $X_3$-C(=O)- | $X_4$-naphthyl | H | 423 |
| 7 | $X_2$-O-CH₃ | $X_3$-C(=O)- | $X_4$-phenyl | H | 372 |
| 8 | $X_2$-O-CH₃ | H | $X_4$-benzyl | H₃C-$X_5$ | 401 |
| 9 | $X_2$-OH | H | $X_4$-CH₃ | CH₃-$X_5$ | 296 |
| 10 | $X_2$-OH | $X_3$-C(=O)-OH | $X_4$-C(=O)-CH₃ | H | 382 |
| 11 | $X_2$-OH | H | H | H | 268 |
| 12 | $X_2$-OH | $X_3$-C(=O)- | $X_4$-CH₃ | H | 296 |
| 13 | $X_2$-OH | $X_3$-C(=O)- | $X_4$-phenyl | H | 358 |
| 14 | $X_2$-OH | $X_3$-C(=O)-O-CH₃ | $X_4$-C(=O)-O-CH₂-fluorenyl | H | 549 |

TABLE 1-continued
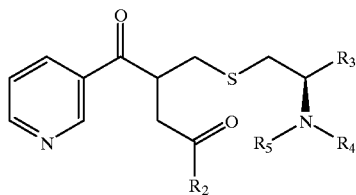
| No. | R₂ | R₃ | R₄ | R₅ | MW (M⁺) |
|---|---|---|---|---|---|
| 15 | X₂–NH–CH₂–C₆H₅ | X₃–C(O)–O–CH₃ | X₄–C(O)–CH₃ | H | 458 |
| 16 | X₂–OH | X₃–C(O)–O–CH₃ | X₄–C(O)–C(CH₃)₃ | H | 410 |
| 17 | X₂–OH | X₃–C(O)–O–CH₃ | X₄–C(O)–CH₂CH₂–cyclopentyl | H | 451 |
| 18 | X₂–OH | X₃–C(O)–O–CH₃ | X₄–C(O)–(2-methylphenyl) | H | 445 |
| 19 | X₂–OH | X₃–C(O)–O–CH₃ | X₄–C(O)–(2-(benzoyloxymethyl)phenyl) | H | 565 |
| 20 | X₂–OH | X₃–C(O)–O–CH₃ | X₄–C(O)–CH₂–S–C₆H₅ | H | 477 |
| 21 | X₂–OH | X₃–C(O)–O–CH₃ | X₄–C(O)–(3,5-bis(trifluoromethyl)phenyl) | H | 566 |

TABLE 1-continued

| No. | R$_2$ | R$_3$ | R$_4$ | R$_5$ | MW (M$^+$) |
|---|---|---|---|---|---|
| 22 | X$_2$—OH | X$_3$—C(O)—O—CH$_3$ | X$_4$—C(O)—CH(C$_2$H$_5$)—CH$_2$CH$_2$CH$_3$ | H | 453 |
| 23 | X$_2$—OH | X$_3$—C(O)—O—CH$_3$ | X$_4$—C(O)—phenyl | H | 430 |
| 24 | X$_2$—OH | X$_3$—C(O)—O—CH$_3$ | X$_4$—C(O)—CH=C(CH$_3$)$_2$ | H | 408 |
| 25 | X$_2$—OH | X$_3$—C(O)—O—CH$_3$ | X$_4$—C(O)—(4-OCF$_3$-phenyl) | H | 514 |
| 26 | X$_2$—OH | X$_3$—C(O)—O—CH$_3$ | X$_4$—C(O)—cyclobutyl | H | 408 |
| 27 | X$_2$—OH | X$_3$—C(O)—O—CH$_3$ | X$_4$—C(O)—(2-furyl) | H | 420 |

TABLE 1-continued
| No. | R₂ | R₃ | R₄ | R₅ | MW (M⁺) |
|---|---|---|---|---|---|
| 28 | 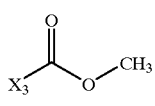 | 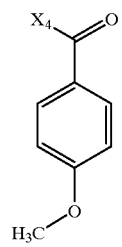 |  | H | 461 |
| 29 | 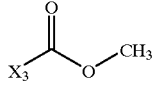 | 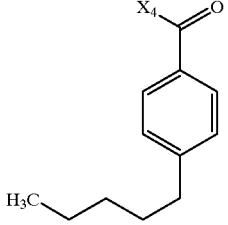 |  | H | 501 |
| 30 | 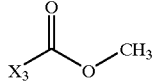 | 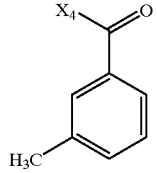 |  | H | 445 |
| 31 | 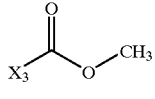 | 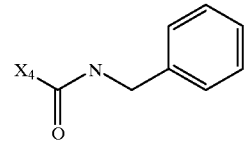 |  | H | 460 |
| 32 | 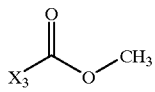 |  | H | H | 326 |
| 33 | 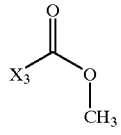 | 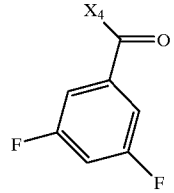 | | H | 466 |

TABLE 1-continued

| No. | R$_2$ | R$_3$ | R$_4$ | R$_5$ | MW (M$^+$) |
|---|---|---|---|---|---|
| 34 | X$_2$–OH | X$_3$–C(=O)–O–CH$_3$ | X$_4$–C(=O)–CH$_2$–cyclopentyl | H | 437 |
| 35 | X$_2$–OH | X$_3$–C(=O)–O–CH$_3$ | X$_4$–C(=O)–(3-methoxyphenyl) | H | 461 |
| 36 | X$_2$–OH | X$_3$–C(=O)–O–CH$_3$ | X$_4$–C(=O)–(2-thienyl) | H | 437 |
| 37 | X$_2$–OH | X$_3$–C(=O)–O–CH$_3$ | X$_4$–C(=O)–CH$_2$–O–CH$_3$ | H | 398 |
| 38 | X$_2$–OH | X$_3$–C(=O)–O–CH$_3$ | X$_4$–C(=O)–(1-adamantyl) | H | 489 |
| 39 | X$_2$–OH | X$_3$–C(=O)–O–CH$_3$ | X$_4$–C(=O)–C(CH$_3$)$_3$ (neopentanoyl) | H | 425 |

TABLE 1-continued

| No. | R₂ | R₃ | R₄ | R₅ | MW (M⁺) |
|---|---|---|---|---|---|
| 40 | X₂–OH | X₃–C(O)OCH₃ | X₄–C(O)-(3-chlorophenyl) | H | 465 |
| 41 | X₂–OH | X₃–C(O)OCH₃ | X₄–C(O)-(4-fluorophenyl) | H | 448 |
| 42 | X₂–OH | X₃–C(O)OCH₃ | X₄–C(O)CH₂O-phenyl | H | 461 |
| 43 | X₂–OH | X₃–C(O)OCH₃ | X₄–C(O)-cyclohexyl | H | 437 |
| 44 | X₂–OH | X₃–C(O)OCH₃ | X₄–C(O)CH₂-(4-methoxyphenyl) | H | 475 |
| 45 | X₂–OH | X₃–C(O)OCH₃ | X₄–C(O)CH(CH₂CH₃)₂ | H | 425 |

TABLE 1-continued
| No. | R2 | R3 | R4 | R5 | MW (M+) |
|---|---|---|---|---|---|
| 46 | 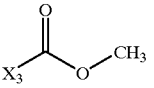 |  |  | H | 445 |
| 47 | 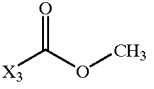 |  |  | H | 509 |
| 48 | 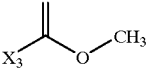 | 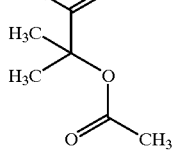 |  | H | 454 |
| 49 | 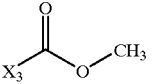 | 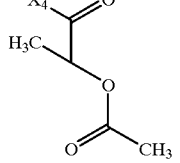 |  | H | 440 |
| 50 | 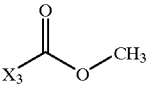 | 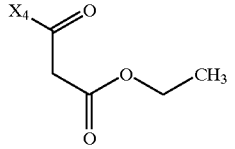 |  | H | 440 |
| 51 | 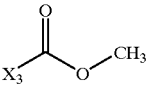 | 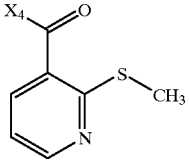 |  | H | 478 |

TABLE 1-continued
| No. | R₂ | R₃ | R₄ | R₅ | MW (M⁺) |
|---|---|---|---|---|---|
| 52 | X₂–OH | X₃–C(O)–O–CH₃ | X₄–C(O)–N-morpholine | H | 439 |
| 53 | X₂–OH | X₃–C(O)–O–CH₃ | X₄–C(O)–CH₂–(2-thienyl) | H | 451 |
| 54 | X₂–OH | X₃–C(O)–O–CH₃ | X₄–C(O)–CH₂–CH₂–CH=CH₂ | H | 408 |
| 55 | X₂–OH | X₃–C(O)–O–CH₃ | X₄–C(O)–CH₂–CH₂–S–CH₃ | H | 429 |
| 56 | X₂–O–CH₃ | H | H | H | 282 |
| 57 | X₂–O–CH₃ | H | X₄–C(O)–CH₂–CH₂–NH–C(O)–CH₃ | H | 395 |
| 58 | X₂–OH | H | X₄–C(O)–CH₂–CH₂–NH–C(O)–CH₃ | H | 381 |
| 59 | X₂–OH | H | X₄–C(O)–CH₃ | H | 310 |
| 60 | X₂–O–CH₃ | X₃–C(O)–O–CH₃ | X₄–C(O)–CH₃ | H | 382 |

TABLE 1-continued

| No. | R$_2$ | R$_3$ | R$_4$ | R$_5$ | MW (M$^+$) |
|---|---|---|---|---|---|
| 61 | X$_2$–O–CH$_3$ | H | X$_4$–C(=O)–CH$_3$ | H | 324 |
| 62 | X$_2$–OH | X$_3$–C(=O)–O–CH$_3$ | X$_4$–C(=O)–CH$_3$ | H | 368 |
| 63 | X$_2$–OH | X$_3$–C(=O)–O–CH$_3$ | X$_4$–C(=O)–(benzo[1,3]dioxol-5-yl) | H | 474 |
| 64 | HO–X$_2$ | X$_3$–C(=O)–O–CH$_3$ | X$_4$–C(=O)–cyclopropyl | H | 394 |
| 65 | HO–X$_2$ | X$_3$–C(=O)–O–CH$_3$ | X$_4$–C(=O)–(4-chlorophenyl) | H | 465 |
| 66 | HO–X$_2$ | X$_3$–C(=O)–O–CH$_3$ | X$_4$–C(=O)–(CH$_2$)$_4$–C(=O)–O–CH$_3$ | H | 469 |
| 67 | HO–X$_2$ | X$_3$–C(=O)–O–CH$_3$ | X$_4$–C(=O)–(4-butoxyphenyl) | H | 503 |

TABLE 1-continued
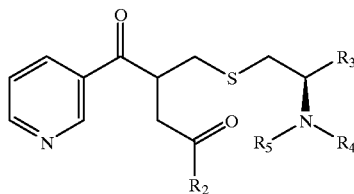
| No. | R₂ | R₃ | R₄ | R₅ | MW (M⁺) |
|---|---|---|---|---|---|
| 68 | HO-X₂ | X₃-C(O)-O-CH₃ | X₄-C(O)-CH₂-O-CH₂-C₆H₅ | H | 475 |
| 69 | HO-X₂ | X₃-C(O)-O-CH₃ | X₄-C(O)-C(O)-O-CH₂CH₃ | H | 426 |
| 70 | HO-X₂ | X₃-C(O)-O-CH₃ | X₄-C(O)-CH(C₆H₅)₂ | H | 521 |
| 71 | HO-X₂ | X₃-C(O)-O-CH₃ | X₄-C(O)-C(cyclopentyl)(4-Cl-C₆H₄) | H | 533 |
| 72 | HO-X₂ | X₃-C(O)-O-CH₃ | X₄-C(O)-quinoxalin-2-yl | H | 483 |
| 73 | HO-X₂ | X₃-C(O)-O-CH₃ | X₄-C(O)-benzothiophen-2-yl | H | 487 |

TABLE 1-continued

| No. | R$_2$ | R$_3$ | R$_4$ | R$_5$ | MW (M$^+$) |
|---|---|---|---|---|---|
| 74 | HO-X$_2$ | X$_3$-C(=O)-O-CH$_3$ | X$_4$-C(=O)-(3-trifluoromethylphenyl) | H | 498 |
| 75 | HO-X$_2$ | X$_3$-C(=O)-O-CH$_3$ | X$_4$-C(=O)-(4-fluorosulfonylphenyl) | H | 513 |
| 76 | HO-X$_2$ | X$_3$-C(=O)-O-CH$_3$ | X$_4$-C(=O)-(3,4,5-trimethoxyphenyl) | H | 521 |
| 77 | HO-X$_2$ | X$_3$-C(=O)-O-CH$_3$ | X$_4$-C(=O)-CH=CH-phenyl | H | 457 |
| 78 | HO-X$_2$ | X$_3$-C(=O)-O-CH$_3$ | X$_4$-C(=O)-(3,4-dimethoxyphenyl) | H | 491 |

TABLE 1-continued

| No. | R₂ | R₃ | R₄ | R₅ | MW (M⁺) |
|---|---|---|---|---|---|
| 79 | HO-X₂ | X₃-C(O)-O-CH₃ | X₄-C(O)-CH₂-O-[3-methyl-5-(1-hydroxyethyl)cyclohexyl] | H | 523 |
| 80 | HO-X₂ | X₃-C(O)-O-CH₃ | X₄-C(O)-(3-cyanophenyl) | H | 455 |
| 81 | HO-X₂ | X₃-C(O)-O-CH₃ | X₄-C(O)-(4-trifluoromethylphenyl) | H | 498 |
| 82 | HO-X₂ | X₃-C(O)-O-CH₃ | X₄-C(O)-(4-phenylazophenyl) | H | 535 |

TABLE 1-continued

| No. | R₂ | R₃ | R₄ | R₅ | MW (M⁺) |
|---|---|---|---|---|---|
| 83 | HO-X₂ | X₃-C(O)-O-CH₃ | X₄-C(O)- (3-chloro-4-methylsulfonyl-thiophen-2-yl) | H | 549 |
| 84 | HO-X₂ | X₃-C(O)-O-CH₃ | X₄-C(O)- (3,4-dichlorophenyl) | H | 499 |
| 85 | HO-X₂ | X₃-C(O)-O-CH₃ | X₄-C(O)-(CH₂)₉-CH₃ | H | 495 |
| 86 | HO-X₂ | X₃-C(O)-O-CH₃ | X₄-C(O)-CH=CH-(3-trifluoromethylphenyl) | H | 525 |
| 87 | HO-X₂ | X₃-C(O)-O-CH₃ | X₄-C(O)- (2,6-dichloropyridin-4-yl) | H | 500 |
| 88 | HO-X₂ | X₃-C(O)-O-CH₃ | X₄-C(O)- (2-acetoxyphenyl) | H | 489 |

TABLE 1-continued
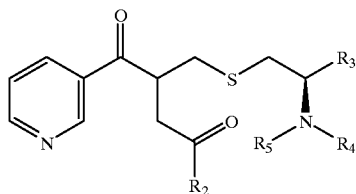
| No. | R₂ | R₃ | R₄ | R₅ | MW (M⁺) |
|---|---|---|---|---|---|
| 89 | X₂–C(OH) | X₃–C(O)–O–CH₃ | X₄–C(O)–(CH₂)₁₄–CH₃ | H | 649 |
| 90 | X₂–C(OH) | X₃–C(O)–O–CH₃ | X₄–C(O)–NH–phenyl | H | 445 |
| 91 | X₂–C(OH) | X₃–C(O)–O–CH₃ | X₄–C(O)–NH–(2-Cl-phenyl) | H | 480 |
| 92 | X₂–C(OH) | X₃–C(O)–O–CH₃ | X₄–C(O)–NH–(3,5-diCl-phenyl) | H | 514 |
| 93 | X₂–C(OH) | X₃–C(O)–O–CH₃ | X₄–C(O)–NH–(3,5-diCl-phenyl) | H | 514 |
| 94 | X₂–C(OH) | X₃–C(O)–O–CH₃ | X₄–C(O)–NH–(3,5-diCl-phenyl) | H | 480 |
| 95 | X₂–C(OH) | X₃–C(O)–O–CH₃ | X₄–C(O)–NH–(2-F-phenyl) | H | 463 |
| 96 | X₂–C(OH) | X₃–C(O)–O–CH₃ | X₄–C(O)–NH–(3-F-phenyl) | H | 463 |
| 97 | X₂–C(OH) | X₃–C(O)–O–CH₃ | X₄–C(O)–NH–(4-F-phenyl) | H | 463 |

TABLE 1-continued

| No. | R$_2$ | R$_3$ | R$_4$ | R$_5$ | MW (M$^+$) |
|---|---|---|---|---|---|
| 98 | HO–X$_2$ | X$_3$–C(O)–OCH$_3$ | X$_4$–C(O)–NH–(2,5-difluorophenyl) | H | 481 |
| 99 | HO–X$_2$ | X$_3$–C(O)–OCH$_3$ | X$_4$–C(O)–NH–(2-trifluoromethylphenyl) | H | 513 |
| 100 | HO–X$_2$ | X$_3$–C(O)–OCH$_3$ | X$_4$–C(O)–NH–(3-trifluoromethylphenyl) | H | 513 |
| 101 | HO–X$_2$ | X$_3$–C(O)–OCH$_3$ | X$_4$–C(O)–NH–(3,5-bis(trifluoromethyl)phenyl) | H | 581 |
| 102 | HO–X$_2$ | X$_3$–C(O)–OCH$_3$ | X$_4$–C(O)–NH–(4-chloro-3-trifluoromethylphenyl) | H | 548 |
| 103 | HO–X$_2$ | X$_3$–C(O)–OCH$_3$ | X$_4$–C(O)–NH–(4-acetylphenyl) | H | 488 |
| 104 | HO–X$_2$ | X$_3$–C(O)–OCH$_3$ | X$_4$–C(O)–NH–(3-acetylphenyl) | H | 488 |

TABLE 1-continued

| No. | R₂ | R₃ | R₄ | R₅ | MW (M⁺) |
|-----|----|----|----|----|---------|
| 105 | HO–X₂ | X₃–C(O)–O–CH₃ | X₄–NH–C(O)–(2-methyl-3-chlorophenyl) | H | 494 |
| 106 | HO–X₂ | X₃–C(O)–O–CH₃ | X₄–NH–C(O)–(2-methyl-4-chlorophenyl) | H | 494 |
| 107 | HO–X₂ | X₃–C(O)–O–CH₃ | X₄–NH–C(O)–(4-ethoxycarbonylphenyl) | H | 518 |
| 108 | HO–X₂ | X₃–C(O)–O–CH₃ | X₄–NH–C(O)–(3-ethoxycarbonylphenyl) | H | 518 |
| 109 | HO–X₂ | X₃–C(O)–O–CH₃ | X₄–NH–C(O)–(3-cyanophenyl) | H | 471 |
| 110 | HO–X₂ | X₃–C(O)–O–CH₃ | X₄–NH–C(O)–(2-methylphenyl) | H | 460 |
| 111 | HO–X₂ | X₃–C(O)–O–CH₃ | X₄–NH–C(O)–(3-methylphenyl) | H | 460 |
| 112 | HO–X₂ | X₃–C(O)–O–CH₃ | X₄–NH–C(O)–(4-methylphenyl) | H | 460 |

TABLE 1-continued

| No. | R₂ | R₃ | R₄ | R₅ | MW (M⁺) |
|---|---|---|---|---|---|
| 113 | HO-X₂ | X₃-C(O)-O-CH₃ | X₄-C(O)-NH-(3,5-dimethylphenyl) | H | 474 |
| 114 | HO-X₂ | X₃-C(O)-O-CH₃ | X₄-C(O)-NH-(4-methoxyphenyl) | H | 476 |
| 115 | HO-X₂ | X₃-C(O)-O-CH₃ | X₄-C(O)-NH-(2-methoxyphenyl) | H | 476 |
| 116 | HO-X₂ | X₃-C(O)-O-CH₃ | X₄-C(O)-NH-(3,4,5-trimethoxyphenyl) | H | 536 |
| 117 | HO-X₂ | X₃-C(O)-O-CH₃ | X₄-C(O)-NH-(4-trifluoromethoxyphenyl) | H | 529 |
| 118 | HO-X₂ | X₃-C(O)-O-CH₃ | X₄-C(O)-NH-(4-methylthiophenyl) | H | 492 |
| 119 | HO-X₂ | X₃-C(O)-O-CH₃ | X₄-C(O)-NH-(1-naphthyl) | H | 496 |
| 120 | HO-X₂ | X₃-C(O)-O-CH₃ | X₄-C(O)-NH-CH₂-(4-methylphenyl) | H | 474 |

TABLE 1-continued

| No. | R₂ | R₃ | R₄ | R₅ | MW (M⁺) |
|---|---|---|---|---|---|
| 121 | HO-X₂ | X₃-C(=O)-O-CH₃ | X₄-C(=O)-NH-CH₂-(2-Cl-C₆H₄) | H | 494 |
| 122 | HO-X₂ | X₃-C(=O)-O-CH₃ | X₄-C(=O)-NH-CH₂-(4-F-C₆H₄) | H | 478 |
| 123 | HO-X₂ | X₃-C(=O)-O-CH₃ | X₄-C(=O)-NH-CH₂-(3,4-Cl₂-C₆H₃) | H | 528 |
| 124 | HO-X₂ | X₃-C(=O)-O-CH₃ | X₄-C(=O)-N(H)-SO₂-(4-CH₃-C₆H₄) | H | 524 |
| 125 | HO-X₂ | X₃-C(=O)-O-CH₃ | X₄-C(=O)-NH-(2-CF₃-4-Cl-C₆H₃) | H | 548 |
| 126 | HO-X₂ | X₃-C(=O)-O-CH₃ | X₄-C(=O)-NH-(4-CH₂CH₃-C₆H₄) | H | 474 |
| 127 | HO-X₂ | X₃-C(=O)-O-CH₃ | X₄-C(=O)-NH-(4-OCH₂CH₃-C₆H₄) | H | 490 |
| 128 | HO-X₂ | X₃-C(=O)-O-CH₃ | X₄-C(=O)-NH-(3-Cl-C₆H₄) | H | 480 |

TABLE 1-continued

| No. | R₂ | R₃ | R₄ | R₅ | MW (M⁺) |
|-----|----|----|----|----|---------|
| 129 | X₂–OH | X₃–C(O)–O–CH₃ | X₄–C(O)–O–CH₂–C₆H₅ | H | 461 |
| 130 | X₂–O–CH₂CH₃ | H | X₄–C(O)–CH₃ | H | 338 |
| 131 | X₂–O–CH₂–C₆H₅ | H | X₄–C(O)–CH₃ | H | 400 |
| 132 | X₂–OH | X₃–C(O)–O–CH₃ | X₄–C(O)–NH–CH₂CH₂CH₃ | H | 411 |
| 133 | X₂–OH | X₃–C(O)–O–CH₃ | X₄–C(O)–N(pentyl chain with H₃C) | H | 454 |
| 134 | X₂–OH | X₃–C(O)–O–CH₃ | X₄–C(O)–NH–(CH₂)₄–CH₃ | H | 440 |
| 135 | X₂–OH | X₃–C(O)–O–CH₃ | X₄–C(O)–NH–CH(CH₃)₂ | H | 411 |
| 136 | X₂–OH | X₃–C(O)–O–CH₃ | X₄–C(O)–NH–CH₂–CH=CH₂ | H | 409 |
| 137 | X₂–OH | X₃–C(O)–O–CH₃ | X₄–C(O)–N(H)–C(O)–CCl₃ | H | 515 |
| 138 | X₂–OH | X₃–C(O)–O–CH₃ | X₄–C(O)–NH–CH₂CH₂–C(O)–O–CH₂CH₃ | H | 470 |

TABLE 1-continued

| No. | R₂ | R₃ | R₄ | R₅ | MW (M⁺) |
|---|---|---|---|---|---|
| 139 | X₂—OH | X₃—C(O)OCH₃ | X₄—C(O)N(H)C(O)Ph | H | 474 |
| 140 | X₂—OH | X₃—C(O)OCH₃ | X₄—C(O)NH-cyclohexyl | H | 452 |
| 141 | X₂—OH | X₃—C(O)OCH₃ | X₄—C(O)NH-(4-CF₃-C₆H₄) | H | 513 |
| 142 | X₂—OH | X₃—C(O)OCH₃ | X₄—C(O)NH-(3-OCH₃-C₆H₄) | H | 476 |
| 143 | X₂—OH | X₃—C(O)OCH₃ | X₄—C(O)O-C₆H₅ | H | 446 |
| 144 | X₂—OH | X₃—C(O)OCH₃ | X₄—C(O)O-(4-Cl-C₆H₄) | H | 481 |
| 145 | X₂—OH | X₃—C(O)OCH₃ | X₄—C(O)O-(4-F-C₆H₄) | H | 464 |
| 146 | X₂—OH | X₃—C(O)OCH₃ | X₄—C(O)O-(4-Br-C₆H₄) | H | 525 |
| 147 | X₂—OH | X₃—C(O)OCH₃ | X₄—C(O)O-(4-NO₂-C₆H₄) | H | 491 |

TABLE 1-continued
| No. | R₂ | R₃ | R₄ | R₅ | MW (M⁺) |
|---|---|---|---|---|---|
| 148 | 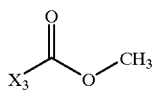 | 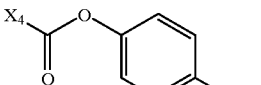 |  | H | 461 |
| 149 | 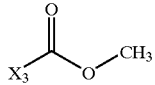 | 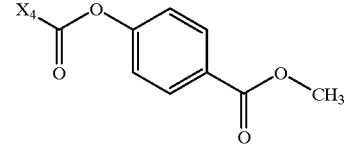 |  | H | 505 |
| 150 | 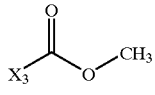 | 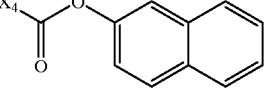 |  | H | 497 |
| 151 | 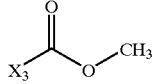 | 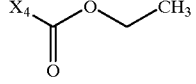 |  | H | 398 |
| 152 | 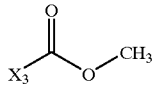 | 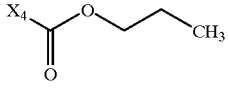 |  | H | 412 |
| 153 | 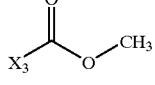 | 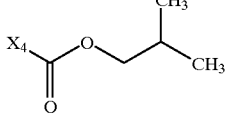 |  | H | 426 |
| 154 | 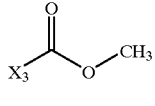 | 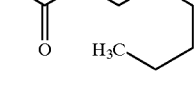 |  | H | 455 |
| 155 | 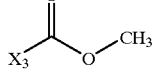 | 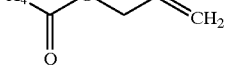 |  | H | 410 |
| 156 | 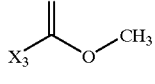 | 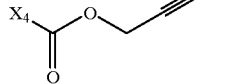 |  | H | 408 |
| 157 | 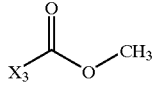 | 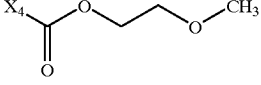 | | H | 428 |

TABLE 1-continued
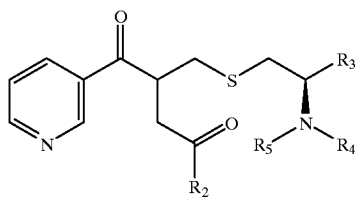
| No. | R₂ | R₃ | R₄ | R₅ | MW (M⁺) |
|---|---|---|---|---|---|
| 158 | X₂–OH | X₃–C(O)–O–CH₃ | X₄–O–C(O)–O–CH₂CH(C₂H₅)CH₂CH₂CH₂CH₃ | H | 483 |
| 159 | X₂–OH | X₃–C(O)–O–CH₃ | X₄–O–C(O)–O–CH₂CCl₃ | H | 502 |
| 160 | X₂–OH | X₃–C(O)–O–CH₃ | X₄–O–C(O)–O–CH₂C(CH₃)₃ | H | 441 |
| 161 | X₂–OH | X₃–C(O)–O–CH₃ | X₄–O–C(O)–O–(4-methoxyphenyl) | H | 477 |
| 162 | X₂–OH | X₃–C(O)–O–CH₃ | X₄–N(H)–C(O)–SO₂–(2-methylphenyl) | H | 524 |
| 163 | X₂–O–CH₂CH₂–(indol-3-yl) | X₃–C(O)–O–CH₃ | X₄–C(O)–CH₃ | H | 512 |
| 164 | X₂–O–CH₂CH₂–(indol-3-yl) | X₃–C(O)–O–CH₃ | X₄–C(O)–CH₃ | H | 396 |

TABLE 1-continued

| No. | R₂ | R₃ | R₄ | R₅ | MW (M⁺) |
|---|---|---|---|---|---|
| 165 | X₂–O–CH₂CH₃ | X₃–C(O)–O–CH₃ | X₄–C(O)–CH₃ | H | 482 |
| 166 | X₂–O–CH₂CH₂–(piperidinyl) | X₃–C(O)–O–CH₃ | X₄–C(O)–CH₃ | H | 480 |
| 167 | X₂–O–CH₃ | X₃–C(O)–O–CH₃ | X₄–C(O)–NH–[3,5-bis(CF₃)phenyl] | H | 596 |
| 168 | X₂–O–CH₂CH₃ | X₃–C(O)–O–CH₃ | X₄–C(O)–[3,5-bis(CF₃)phenyl] | H | 595 |
| 169 | X₂–O–CH₃ | X₃–C(O)–O–CH₃ | X₄–C(O)–[3,5-bis(CF₃)phenyl] | H | 581 |
| 170 | X₂–O–CH₃ | H | X₄–C(O)–CF₃ | H | 378 |

TABLE 1-continued

| No. | R₂ | R₃ | R₄ | R₅ | MW (M⁺) |
|---|---|---|---|---|---|
| 171 | $X_2$-S(O)₂-N-phenyl | H | $X_4$-C(O)-CH₃ | H | 450 |
| 172 | $X_2$-O-CH₂CH₂-NH₂ | $X_3$-C(O)-O-CH₃ | $X_4$-C(O)-CH₃ | H | 411 |
| 173 | $X_2$-O-CH₂CH₂-NH-C(O)-biotinyl | $X_3$-C(O)-O-CH₃ | $X_4$-C(O)-CH₃ | H | 638 |
| 174 | $X_2$-O-CH₃ | $X_3$-C(O)-O-CH₃ | $X_4$-C(O)-NH-CH₂CH₂CH₃ | H | 426 |
| 175 | $X_2$-O-CH₃ | $X_3$-C(O)-O-CH₃ | $X_4$-C(O)-NH-(CH₂)₄CH₃ | H | 454 |
| 176 | $X_2$-O-CH₃ | $X_3$-C(O)-O-CH₃ | $X_4$-C(O)-NH-(CH₂)₅CH₃ | H | 468 |
| 177 | $X_2$-O-CH₃ | $X_3$-C(O)-O-CH₃ | $X_4$-C(O)-NH-CH(CH₃)₂ | H | 426 |
| 178 | $X_2$-O-CH₃ | $X_3$-C(O)-O-CH₃ | $X_4$-C(O)-NH-cyclohexyl | H | 466 |
| 179 | $X_2$-O-CH₃ | $X_3$-C(O)-O-CH₃ | $X_4$-C(O)-O-CH₂-phenyl | H | 475 |

TABLE 1-continued

| No. | R₂ | R₃ | R₄ | R₅ | MW (M⁺) |
|---|---|---|---|---|---|
| 180 | X₂—O—CH₃ | X₃—C(O)—O—CH₃ | X₄—C(O)—N(H)—C(O)—Ph | H | 488 |
| 181 | X₂—O—CH₃ | X₃—C(O)—O—CH₃ | X₄—C(O)—N(H)—(3-methoxyphenyl) | H | 490 |
| 182 | X₂—O—CH₃ | X₃—C(O)—O—CH₃ | X₄—C(O)—O—(4-chlorophenyl) | H | 495 |
| 183 | X₂—O—CH₃ | X₃—C(O)—O—CH₃ | X₄—C(O)—O—(4-bromophenyl) | H | 539 |
| 184 | X₂—O—CH₃ | X₃—C(O)—O—CH₃ | X₄—C(O)—O—CH₂CH₂CH₃ | H | 426 |
| 185 | X₂—N(H)—S(O)₂—CH₃ | X₃—C(O)—O—CH₃ | X₄—C(O)—CH₃ | H | 446 |
| 186 | X₂—O—CH₂—Ph | H | X₄—C(O)—CH₃ | H | 400 |
| 187 | X₂—O—CH₂CH₂CH₂CH₃ | H | X₄—C(O)—CH₃ | H | 366 |

TABLE 1-continued
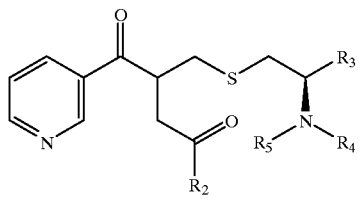
| No. | R$_2$ | R$_3$ | R$_4$ | R$_5$ | MW (M$^+$) |
|---|---|---|---|---|---|
| 188 | X$_2$–N(CH$_3$)(CH$_3$) | H | X$_4$–C(=O)CH$_3$ | H | 337 |
| 189 | X$_2$–piperidinyl | H | X$_4$–C(=O)CH$_3$ | H | 378 |
| 190 | X$_2$–O–CH$_2$–cyclopropyl | H | X$_4$–C(=O)CH$_3$ | H | 364 |
| 191 | X$_2$–O–indanyl | H | X$_4$–C(=O)CH$_3$ | H | 427 |
| 192 | X$_2$–O–(CH$_2$)$_3$–(3-pyridyl) | H | X$_4$–C(=O)CH$_3$ | H | 430 |
| 193 | X$_2$–NH–CH$_2$–C(=O)–O–CH$_2$CH$_3$ | H | X$_4$–C(=O)CH$_3$ | H | 395 |
| 194 | X$_2$–pyrrolidinyl | H | X$_4$–C(=O)CH$_3$ | H | 363 |

TABLE 1-continued

| No. | R₂ | R₃ | R₄ | R₅ | MW (M⁺) |
|-----|----|----|----|----|---------|
| 195 | X₂–O–CH₂CH₃ | H | X₄–CH₂CH₂CH₂CH₃ | H | 352 |
| 196 | X₂–O–(indanyl) | X₃–C(O)–OCH₃ | X₄–C(O)–CH₃ | H | 485 |
| 197 | X₂–O–CH₂CH₂CH₂–(3-pyridyl) | X₃–C(O)–OCH₃ | X₄–C(O)–CH₃ | H | 488 |
| 198 | X₂–O–CH₂CH₂CH₃ | H | X₄–C(O)–CH₃ | H | 352 |
| 199 | X₂–O–CH₂CH₂–(piperidin-1-yl) | H | X₄–C(O)–CH₃ | H | 422 |
| 200 | X₂–N(H)–CH₂–(3-pyridyl) | H | X₄–C(O)–CH₃ | H | 401 |

TABLE 1-continued
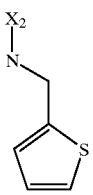
| No. | R₂ | R₃ | R₄ | R₅ | MW (M⁺) |
|---|---|---|---|---|---|
| 201 | 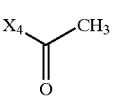 | H | 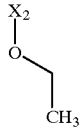 | H | 406 |
| 202 | 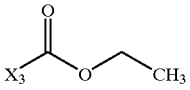 | 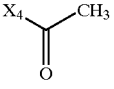 | 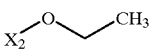 | H | 410 |
| 203 | 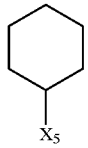 | H | H | 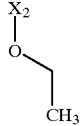 | 379 |
| 204 | 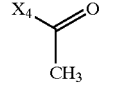 | H | 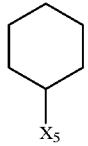 | 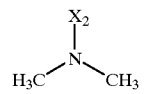 | 421 |
| 205 | 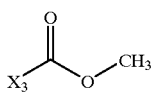 | 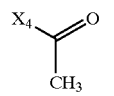 | 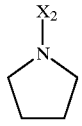 | H | 395 |
| 206 | 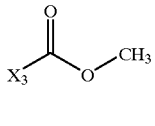 | 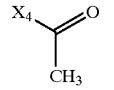 | 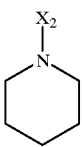 | H | 422 |
| 207 | 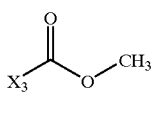 | 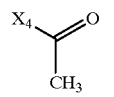 |  | H | 436 |

TABLE 1-continued
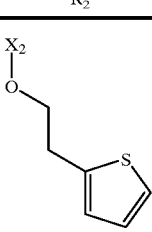
| No. | R₂ | R₃ | R₄ | R₅ | MW (M⁺) |
|---|---|---|---|---|---|
| 208 | 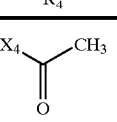 | H | 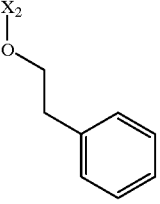 | H | 421 |
| 209 | 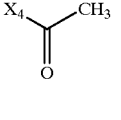 | H | 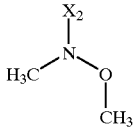 | H | 415 |
| 210 | 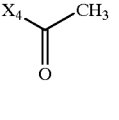 | H |  | H | 353 |
| 211 | 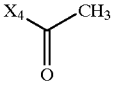 | H | 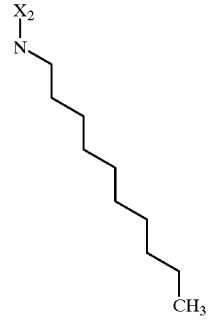 | H | 323 |
| 212 | 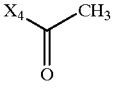 | H |  | H | 450 |
| 213 | 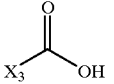 | 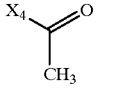 | 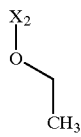 | H | 354 |
| 214 | 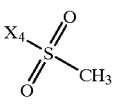 | H | 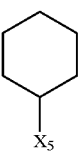 | (cyclohexyl) | 457 |

TABLE 1-continued

| No. | R₂ | R₃ | R₄ | R₅ | MW (M⁺) |
|---|---|---|---|---|---|
| 215 | X₂—O—CH₂—CH₃ | H | X₄—C(O)—C(O)—O—CH₃ | cyclohexyl (X₅) | 465 |
| 216 | X₂—O—CH₂—CH₃ | H | X₄—C(O)—(3,5-difluorophenyl) | cyclohexyl (X₅) | 519 |
| 217 | X₂—O—CH₂—CH₃ | H | X₄—CH₂—C(O)—O—CH₂—CH₃ | cyclohexyl (X₅) | 465 |
| 218 | X₂—morpholino (N-linked) | H | X₄—C(O)—CH₃ | H | 379 |
| 219 | X₂—NH—cyclohexyl | H | X₄—C(O)—CH₃ | H | 392 |
| 220 | X₂—O—CH₂—CH₃ | H | X₄—C(O)—NH—(CH₂)₄—CH₃ | cyclohexyl (X₅) | 506 |
| 221 | X₂—O—CH₂—CH₃ | H | X₄—C(O)—NH—(2-methoxyphenyl) | cyclohexyl (X₅) | 528 |

TABLE 1-continued

| No. | R₂ | R₃ | R₄ | R₅ | MW (M⁺) |
|---|---|---|---|---|---|
| 222 | X₂–O–CH₂CH₃ | H | X₄–C(O)–O–(4-Cl-C₆H₄) | cyclohexyl-X₅ | 533 |
| 223 | X₂–O–CH₃ | X₃–C(O)–O–CH₃ | X₄–C(O)–N(H)–CH₂CH₂–C(O)–O–CH₂CH₃ | H | 484 |
| 224 | X₂–O–CH₃ | X₃–C(O)–O–CH₃ | X₄–C(O)–O–CH(CH₃)₂ | H | 426 |
| 225 | X₂–O–CH₃ | X₃–C(O)–O–CH₃ | X₄–C(O)–O–CH₂–CH=CH₂ | H | 424 |
| 226 | X₂–O–CH₃ | X₃–C(O)–O–CH₃ | X₄–C(O)–O–CH₂–C≡CH | H | 422 |
| 227 | X₂–O–CH₃ | X₃–C(O)–O–CH₃ | X₄–C(O)–N(H)–C₆H₅ | H | 460 |
| 228 | X₂–O–CH₃ | X₃–C(O)–O–CH₃ | X₄–C(O)–N(H)–(2-Cl-C₆H₄) | H | 494 |
| 229 | X₂–O–CH₃ | X₃–C(O)–O–CH₃ | X₄–C(O)–N(H)–(3,5-Cl₂-C₆H₃) | H | 528 |
| 230 | X₂–O–CH₃ | X₃–C(O)–O–CH₃ | X₄–C(O)–N(H)–(4-Cl-C₆H₄) | H | 494 |

TABLE 1-continued

![Structure: pyridin-3-yl-C(=O)-CH(CH2-C(=O)-R2)-CH2-S-CH2-CH(R3)-N(R4)(R5)]

| No. | R2 | R3 | R4 | R5 | MW (M+) |
|---|---|---|---|---|---|
| 231 | X2—O—CH3 (H3C—O—X2) | X3—C(=O)—O—CH3 | X4—C(=O)—NH—(2-F-C6H4) | H | 478 |
| 232 | X2—O—CH3 | X3—C(=O)—O—CH3 | X4—C(=O)—NH—(3-F-C6H4) | H | 478 |
| 233 | X2—O—CH3 | X3—C(=O)—O—CH3 | X4—C(=O)—NH—(4-F-C6H4) | H | 478 |
| 234 | X2—O—CH3 | X3—C(=O)—O—CH3 | X4—C(=O)—NH—(2-CF3-C6H4) | H | 528 |
| 235 | X2—O—CH3 | X3—C(=O)—O—CH3 | X4—C(=O)—NH—(3-CF3-C6H4) | H | 528 |
| 236 | X2—O—CH3 | X3—C(=O)—O—CH3 | X4—C(=O)—NH—(3-acetyl-C6H4) | H | 502 |
| 237 | X2—O—CH3 | X3—C(=O)—O—CH3 | X4—C(=O)—NH—(4-CO2Et-C6H4) | H | 532 |
| 238 | X2—O—CH3 | X3—C(=O)—O—CH3 | X4—C(=O)—NH—(2-CH3-C6H4) | H | 474 |

TABLE 1-continued

| No. | R₂ | R₃ | R₄ | R₅ | MW (M⁺) |
|---|---|---|---|---|---|
| 239 | H₃C-O-X₂ | X₃-C(O)-O-CH₃ | X₄-C(O)-NH-(4-methylphenyl) | H | 474 |
| 240 | H₃C-O-X₂ | X₃-C(O)-O-CH₃ | X₄-C(O)-NH-(3,5-dimethylphenyl) | H | 488 |
| 241 | H₃C-O-X₂ | X₃-C(O)-O-CH₃ | X₄-C(O)-NH-(2-methoxyphenyl) | H | 490 |
| 242 | H₃C-O-X₂ | X₃-C(O)-O-CH₃ | X₄-C(O)-NH-(3,4,5-trimethoxyphenyl) | H | 550 |
| 243 | H₃C-O-X₂ | X₃-C(O)-O-CH₃ | X₄-C(O)-NH-(1-naphthyl) | H | 510 |
| 244 | H₃C-O-X₂ | X₃-C(O)-O-CH₃ | X₄-C(O)-NH-CH₂-(4-methylphenyl) | H | 488 |
| 245 | H₃C-O-X₂ | X₃-C(O)-O-CH₃ | X₄-C(O)-NH-CH₂-(2-chlorophenyl) | H | 508 |

TABLE 1-continued

| No. | R₂ | R₃ | R₄ | R₅ | MW (M⁺) |
|---|---|---|---|---|---|
| 246 | H₃C-O-X₂ | X₃-C(O)-O-CH₃ | X₄-C(O)-N(H)-CH₂-(4-F-C₆H₄) | H | 492 |
| 247 | H₃C-O-X₂ | X₃-C(O)-O-CH₃ | X₄-C(O)-N(H)-CH₂-(3,4-Cl₂-C₆H₃) | H | 542 |
| 248 | H₃C-O-X₂ | X₃-C(O)-O-CH₃ | X₄-C(O)-N(H)-(4-OEt-C₆H₄) | H | 504 |
| 249 | H₃C-O-X₂ | X₃-C(O)-O-CH₃ | X₄-C(O)-N(H)-(3-Cl-C₆H₄) | H | 494 |
| 250 | H₃C-O-X₂ | X₃-C(O)-O-CH₃ | X₄-C(O)-N(H)-(4-CF₃-C₆H₄) | H | 528 |
| 251 | H₃C-O-X₂ | X₃-C(O)-O-CH₃ | X₄-C(O)-O-C(CH₃)₃ | H | 441 |
| 252 | X₂-O-CH₂-CH₃ | H | 2-oxocyclopentyl (X₄) | H | 364 |
| 253 | X₂-O-CH₃ | X₃-C(O)-O-CH₃ | H | H | 340 |
| 254 | X₂-O-CH₃ | X₃-C(O)-OH | X₄-C(O)-CH₃ | H | 368 |

TABLE 1-continued

| No. | R$_2$ | R$_3$ | R$_4$ | R$_5$ | MW (M$^+$) |
|---|---|---|---|---|---|
| 255 | X$_2$-O-CH$_2$CH$_3$ | H | X$_4$-SO$_2$-(4-chlorophenyl) | cyclohexyl-X$_5$ | 553 |
| 256 | X$_2$-O-CH$_2$CH$_3$ | H | X$_4$-SO$_2$-(quinolin-5-yl) | cyclohexyl-X$_5$ | 570 |
| 257 | X$_2$-O-CH$_2$CH$_3$ | H | X$_4$-SO$_2$-(thien-2-yl) | cyclohexyl-X$_5$ | 525 |
| 258 | X$_2$-N(CH$_3$)$_2$ | X$_3$-C(O)N(CH$_3$)$_2$ | X$_4$-C(O)CH$_3$ | H | 409 |
| 259 | X$_2$-pyrrolidin-1-yl | X$_3$-C(O)-pyrrolidin-1-yl | X$_4$-C(O)CH$_3$ | H | 461 |
| 260 | X$_2$-piperidin-1-yl | X$_3$-C(O)-piperidin-1-yl | X$_4$-C(O)CH$_3$ | H | 489 |
| 261 | X$_2$-NH-CH$_2$CH$_2$CH$_2$-phenyl | X$_3$-C(O)NH-CH$_2$CH$_2$CH$_2$-phenyl | X$_4$-C(O)CH$_3$ | H | 589 |

TABLE 1-continued
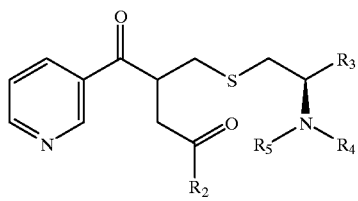
| No. | R2 | R3 | R4 | R5 | MW (M+) |
|---|---|---|---|---|---|
| 262 | X2-N-(CH2)3-imidazole | X3-C(O)-NH-(CH2)3-imidazole | X4-C(O)CH3 | H | 569 |
| 263 | X2-N(CH3)2 | H | X4-C(O)CH3 | cyclohexyl-X5 | 420 |
| 264 | X2-piperidine | H | X4-C(O)CH3 | cyclohexyl-X5 | 460 |
| 265 | X2-NH-(CH2)3-OCH3 | H | X4-C(O)CH3 | H | 381 |
| 266 | X2-NH-(CH2)3-CH3 | H | X4-C(O)CH3 | H | 365 |
| 267 | X2-N-methylpiperazine | H | X4-C(O)CH3 | H | 393 |

TABLE 1-continued

| No. | R₂ | R₃ | R₄ | R₅ | MW (M⁺) |
|-----|----|----|----|----|---------|
| 268 | X₂–O–CH₃ (ethoxy) | H | X₄–C(O)–CH₂CH₃ | cyclohexyl-X₅ | 435 |
| 269 | X₂–O–CH₃ (ethoxy) | H | X₄–C(O)–CH₂–O–CH₃ | cyclohexyl-X₅ | 451 |
| 270 | X₂–O–CH₃ (ethoxy) | H | X₄–C(O)–isoxazol-5-yl | cyclohexyl-X₅ | 474 |
| 271 | X₂–O–CH₃ (ethoxy) | H | X₄–C(O)–O–CH₂CH₃ | cyclohexyl-X₅ | 451 |
| 272 | X₂–O–CH₃ (ethoxy) | H | X₄–C(O)–morpholino | cyclohexyl-X₅ | 492 |
| 273 | X₂–O–CH₂CH₃ | H | X₄–C(O)–N(CH₃)–CH₂CH₃ | cyclohexyl-X₅ | 450 |
| 274 | X₂–N(4-benzylpiperazin-1-yl) | X₃–C(O)–N(4-benzylpiperazin-1-yl) | X₄–C(O)–CH₃ | H | 671 |

TABLE 1-continued

| No. | R$_2$ | R$_3$ | R$_4$ | R$_5$ | MW (M$^+$) |
|---|---|---|---|---|---|
| 275 | X$_2$-O-CH$_2$CH$_3$ | H | X$_4$-C(O)-(3,5-difluorophenyl) | X$_5$-CH$_2$CH$_2$CH$_2$CH$_3$ | 493 |
| 276 | X$_2$-O-CH$_2$CH$_3$ | H | X$_4$-C(O)-CH$_3$ | X$_5$-CH$_2$CH$_2$CH$_2$CH$_3$ | 395 |
| 277 | X$_2$-O-CH$_3$ | X$_3$-C(O)-O-CH$_3$ | X$_4$-C(O)-CF$_3$ | H | 436 |
| 278 | X$_2$-O-CH$_3$ | X$_3$-C(O)-O-CH$_3$ | X$_4$-C(O)-NH-SO$_2$-(2-methylphenyl) | H | 538 |
| 279 | X$_2$-O-CH$_3$ | X$_3$-C(O)-O-CH$_3$ | X$_4$-C(O)-O-(4-fluorophenyl) | H | 478 |
| 280 | X$_2$-O-CH$_3$ | X$_3$-C(O)-O-CH$_3$ | X$_4$-C(O)-O-(4-methylphenyl) | H | 475 |
| 281 | X$_2$-O-CH$_3$ | X$_3$-C(O)-O-CH$_3$ | X$_4$-C(O)-O-phenyl | H | 461 |
| 282 | X$_2$-O-CH$_3$ | X$_3$-C(O)-O-CH$_3$ | X$_4$-C(O)-O-(4-methoxyphenyl) | H | 491 |
| 283 | X$_2$-O-CH$_3$ | X$_3$-C(O)-O-CH$_3$ | X$_4$-C(O)-O-CH$_2$CCl$_3$ | H | 516 |

TABLE 1-continued

| No. | R₂ | R₃ | R₄ | R₅ | MW (M⁺) |
|---|---|---|---|---|---|
| 284 | X₂–O–CH₃ (H₃C–O) | X₃–C(=O)–O–CH₃ | X₄–C(=O)–O–CH₂–C(CH₃)₃ (neopentyl ester) | H | 455 |
| 285 | X₂–O–CH₃ | X₃–C(=O)–O–CH₃ | X₄–C(=O)–N(H)–CH₂–CH=CH₂ | H | 423 |
| 286 | X₂–O–CH₃ | X₃–C(=O)–O–CH₃ | X₄–S(=O)₂–phenyl | H | 481 |
| 287 | X₂–O–CH₃ | X₃–C(=O)–O–CH₃ | X₄–S(=O)₂–(4-methylphenyl) | H | 495 |
| 288 | X₂–O–CH₃ | X₃–C(=O)–O–CH₃ | X₄–S(=O)₂–(4-methoxyphenyl) | H | 511 |
| 289 | X₂–O–CH₃ | X₃–C(=O)–O–CH₃ | X₄–S(=O)₂–(4-tert-butylphenyl) | H | 537 |
| 290 | X₂–O–CH₃ | X₃–C(=O)–O–CH₃ | X₄–S(=O)₂–(2,4,6-trimethylphenyl) | H | 523 |

TABLE 1-continued

| No. | R$_2$ | R$_3$ | R$_4$ | R$_5$ | MW (M$^+$) |
|---|---|---|---|---|---|
| 291 | H$_3$C-O-X$_2$ | X$_3$-C(O)-O-CH$_3$ | X$_4$-SO$_2$-(2,4,6-triisopropylphenyl) | H | 607 |
| 292 | H$_3$C-O-X$_2$ | X$_3$-C(O)-O-CH$_3$ | X$_4$-SO$_2$-(2,5-dimethoxyphenyl) | H | 541 |
| 293 | H$_3$C-O-X$_2$ | X$_3$-C(O)-O-CH$_3$ | X$_4$-SO$_2$-(3,4-dimethoxyphenyl) | H | 541 |
| 294 | H$_3$C-O-X$_2$ | X$_3$-C(O)-O-CH$_3$ | X$_4$-SO$_2$-(4-trifluoromethylphenyl) | H | 549 |
| 295 | H$_3$C-O-X$_2$ | X$_3$-C(O)-O-CH$_3$ | X$_4$-SO$_2$-(3,5-bis(trifluoromethyl)phenyl) | H | 617 |
| 296 | H$_3$C-O-X$_2$ | X$_3$-C(O)-O-CH$_3$ | X$_4$-SO$_2$-(2-chlorophenyl) | H | 515 |

TABLE 1-continued

| No. | R$_2$ | R$_3$ | R$_4$ | R$_5$ | MW (M$^+$) |
|---|---|---|---|---|---|
| 297 | X$_2$—O—CH$_3$ (H$_3$C—O) | X$_3$—C(=O)—O—CH$_3$ | X$_4$—S(=O)$_2$—(3-Cl-phenyl) | H | 515 |
| 298 | X$_2$—O—CH$_3$ | X$_3$—C(=O)—O—CH$_3$ | X$_4$—S(=O)$_2$—(4-Cl-phenyl) | H | 515 |
| 299 | X$_2$—O—CH$_3$ | X$_3$—C(=O)—O—CH$_3$ | X$_4$—S(=O)$_2$—(2,3-diCl-phenyl) | H | 549 |
| 300 | X$_2$—O—CH$_3$ | X$_3$—C(=O)—O—CH$_3$ | X$_4$—S(=O)$_2$—(2,6-diCl-phenyl) | H | 549 |
| 301 | X$_2$—O—CH$_3$ | X$_3$—C(=O)—O—CH$_3$ | X$_4$—S(=O)$_2$—(2,4-diCl-phenyl) | H | 549 |
| 302 | X$_2$—O—CH$_3$ | X$_3$—C(=O)—O—CH$_3$ | X$_4$—S(=O)$_2$—(2,5-diCl-phenyl) | H | 549 |
| 303 | X$_2$—O—CH$_3$ | X$_3$—C(=O)—O—CH$_3$ | X$_4$—S(=O)$_2$—(2,4,5-triCl-phenyl) | H | 584 |

TABLE 1-continued
| No. | R₂ | R₃ | R₄ | R₅ | MW (M⁺) |
|---|---|---|---|---|---|
| 304 | 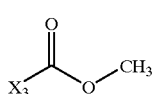 | 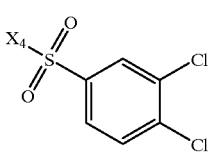 |  | H | 549 |
| 305 | 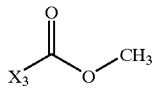 | 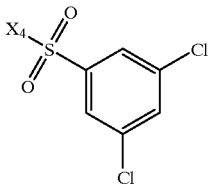 |  | H | 549 |
| 306 | 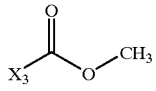 | 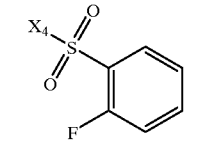 |  | H | 499 |
| 307 | 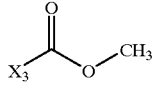 | 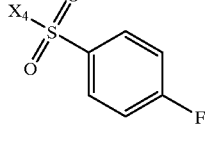 |  | H | 499 |
| 308 | 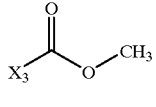 | 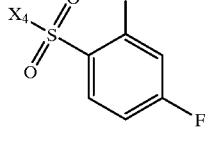 |  | H | 517 |
| 309 | 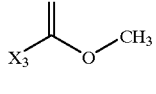 | 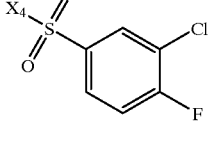 |  | H | 533 |
| 310 | 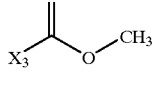 | 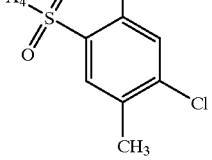 | | H | 543 |

TABLE 1-continued

| No. | R₂ | R₃ | R₄ | R₅ | MW (M⁺) |
|---|---|---|---|---|---|
| 311 | H₃C-O-X₂ | X₃-C(O)-O-CH₃ | X₄-SO₂-(4-acetylphenyl) | H | 523 |
| 312 | H₃C-O-X₂ | X₃-C(O)-O-CH₃ | X₄-SO₂-(1-naphthyl) | H | 531 |
| 313 | H₃C-O-X₂ | X₃-C(O)-O-CH₃ | X₄-SO₂-(5-dimethylamino-1-naphthyl) | H | 574 |
| 314 | H₃C-O-X₂ | X₃-C(O)-O-CH₃ | X₄-SO₂-(2-naphthyl) | H | 531 |
| 315 | H₃C-O-X₂ | X₃-C(O)-O-CH₃ | X₄-SO₂-(5-quinolyl) | H | 532 |
| 316 | H₃C-O-X₂ | X₃-C(O)-O-CH₃ | X₄-SO₂-CH₃ | H | 418 |
| 317 | H₃C-O-X₂ | X₃-C(O)-O-CH₃ | X₄-SO₂-CH₂CH₃ | H | 433 |
| 318 | H₃C-O-X₂ | X₃-C(O)-O-CH₃ | X₄-SO₂-CH₂CH₂CH₃ | H | 447 |

TABLE 1-continued
| No. | R₂ | R₃ | R₄ | R₅ | MW (M⁺) |
|---|---|---|---|---|---|
| 319 | 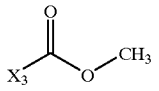 | 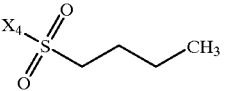 |  | H | 461 |
| 320 | 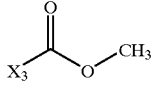 | 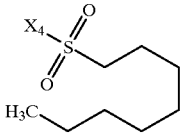 |  | H | 517 |
| 321 | 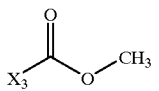 | 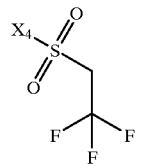 |  | H | 486 |
| 322 | 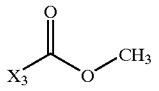 | 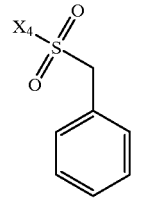 |  | H | 495 |
| 323 | 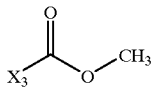 | 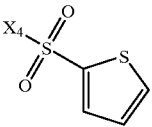 |  | H | 487 |
| 324 | 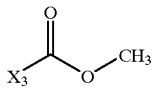 | 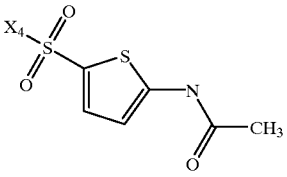 |  | H | 559 |
| 325 | 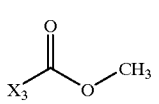 | 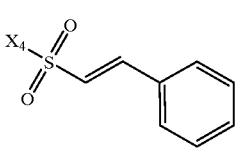 |  | H | 507 |

TABLE 1-continued
| No. | R₂ | R₃ | R₄ | R₅ | MW (M⁺) |
|---|---|---|---|---|---|
| 326 | 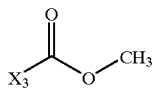 | 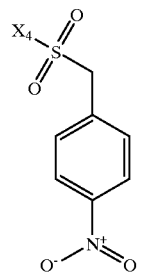 |  | H | 540 |
| 327 | 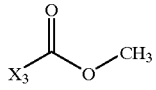 | 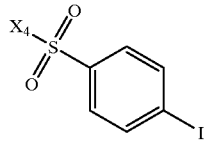 |  | H | 606 |
| 328 | 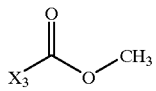 | 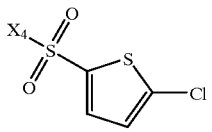 |  | H | 521 |
| 329 | 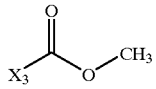 | 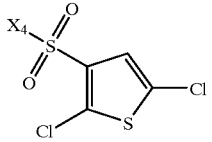 |  | H | 555 |
| 330 | 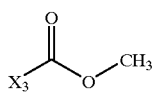 | 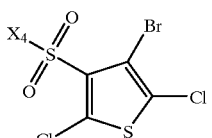 | 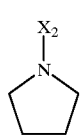 | H | 634 |
| 331 | 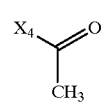 | H | 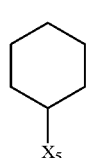 | 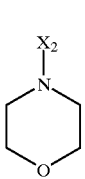 | 446 |
| 332 | 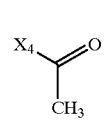 | H | 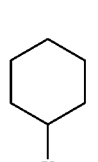 | 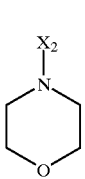 | 462 |

TABLE 1-continued

[Structure: 1-(pyridin-3-yl)-2-[(2-aminoethylthio)methyl]-4-oxo compound with substituents R₂, R₃, R₄, R₅]

| No. | R₂ | R₃ | R₄ | R₅ | MW (M⁺) |
|---|---|---|---|---|---|
| 333 | X₂–N(CH₂CH₃)₂ | H | X₄–C(O)CH₃ | cyclohexyl (X₅) | 448 |
| 334 | X₂–NH–CH₂CH₂–(pyrrolidin-1-yl) | H | X₄–C(O)CH₃ | cyclohexyl (X₅) | 489 |
| 335 | X₂–(4-methylpiperazin-1-yl) | H | X₄–C(O)CH₃ | cyclohexyl (X₅) | 475 |
| 336 | X₂–OH | H | X₄–C(O)CH₃ | cyclohexyl (X₅) | 393 |
| 337 | X₂–O–CH₂CH₃ | H | X₄–C(O)–(4-fluorophenyl) | H | 418 |
| 338 | X₂–O–CH₂CH₃ | H | X₄–C(O)–(3-cyanophenyl) | H | 426 |

TABLE 1-continued

| No. | R₂ | R₃ | R₄ | R₅ | MW (M⁺) |
|---|---|---|---|---|---|
| 339 | X₂–O–CH₂CH₃ | H | X₄–C(O)–(3,5-bis(trifluoromethyl)phenyl) | H | 536 |
| 340 | X₂–O–CH₂CH₃ | H | X₄–C(O)–(4-cyanophenyl) | H | 426 |
| 341 | X₂–O–CH₂CH₃ | H | X₄–C(O)–(3,5-difluorophenyl) | H | 436 |
| 342 | X₂–O–CH₂CH₃ | H | X₄–C(O)–(2-furyl) | H | 390 |
| 343 | X₂–O–CH₂CH₃ | H | X₄–C(O)–(2-furyl) | H | 407 |
| 344 | X₂–O–CH₂CH₃ | H | X₄–C(O)–NH–(4-fluorophenyl) | H | 434 |
| 345 | X₂–O–CH₂CH₃ | H | X₄–C(O)–NH–(4-ethoxyphenyl) | H | 460 |

TABLE 1-continued

| No. | R₂ | R₃ | R₄ | R₅ | MW (M⁺) |
|---|---|---|---|---|---|
| 346 | X₂–O–CH₂CH₃ | H | X₄–C(O)–CH₂–C(O)–O–CH₂CH₃ | X₅–CH₂CH₂CH₂CH₃ | 467 |
| 347 | X₂–O–CH₂CH₃ | H | X₄–C(O)–(4-F-C₆H₄) | X₅–CH₂CH₂CH₂CH₃ | 475 |
| 348 | X₂–O–CH₂CH₃ | H | X₄–C(O)–NH–cyclohexyl | X₅–CH₂CH₂CH₂CH₃ | 478 |
| 349 | X₂–O–CH₂CH₃ | H | X₄–C(O)–NH–(4-CH₃-C₆H₄) | X₅–CH₂CH₂CH₂CH₃ | 486 |
| 350 | X₂–O–CH₂CH₃ | H | X₄–C(O)–NH–CH(CH₃)₂ | X₅–CH₂CH₂CH₂CH₃ | 438 |
| 351 | X₂–O–CH₂CH₃ | H | X₄–C(O)–(2-thienyl) | X₅–CH₂CH₂CH₂CH₃ | 463 |
| 352 | X₂–O–CH₂CH₃ | H | X₄–C(O)–CH₂CH₂–cyclopentyl | X₅–CH₂CH₂CH₂CH₃ | 477 |
| 353 | X₂–O–CH₂CH₃ | H | X₄–C(O)–(4-CN-C₆H₄) | X₅–CH₂CH₂CH₂CH₃ | 482 |

TABLE 1-continued

| No. | R₂ | R₃ | R₄ | R₅ | MW (M⁺) |
|---|---|---|---|---|---|
| 354 | X₂-O-CH₂CH₃ | H | X₄-C(O)-NH-C₆H₄-O-CH₂CH₃ | X₅-CH₂CH₂CH₂CH₃ | 516 |
| 355 | X₂-O-CH₂CH₃ | H | X₄-C(O)-adamantyl | X₅-CH₂CH₂CH₂CH₃ | 515 |
| 356 | X₂-N(CH₃)₂ | X₃-C(O)OH | X₄-C(O)CH₃ | H | 381 |
| 357 | X₂-O-CH₂CH₃ | H | X₄-C(O)-C₆H₄-F | X₅-cyclohexyl | 501 |
| 358 | X₂-O-CH₂CH₃ | H | X₄-C(O)-C₆H₄-CN | X₅-cyclohexyl | 508 |
| 359 | X₂-O-CH₂CH₃ | H | X₄-C(O)-thiophene | X₅-cyclohexyl | 489 |
| 360 | X₂-O-CH₂CH₃ | H | X₄-C(O)-NH-C₆H₄-O-CH₂CH₃ | X₅-cyclohexyl | 542 |

TABLE 1-continued

| No. | R$_2$ | R$_3$ | R$_4$ | R$_5$ | MW (M$^+$) |
|---|---|---|---|---|---|
| 361 | X$_2$-O-CH$_2$CH$_3$ | H | X$_4$-C(O)-N(H)-CH(CH$_3$)$_2$ | cyclohexyl-X$_5$ | 464 |
| 362 | X$_2$-O-CH$_2$CH$_3$ | H | X$_4$-C(O)-N(H)-(4-F-C$_6$H$_4$) | cyclohexyl-X$_5$ | 516 |
| 363 | X$_2$-O-CH$_2$CH$_3$ | H | X$_4$-C(O)-N(H)-C$_6$H$_5$ | H | 416 |
| 364 | X$_2$-O-CH$_2$CH$_3$ | H | X$_4$-C(O)-N(H)-CH(CH$_3$)$_2$ | H | 381 |
| 365 | X$_2$-piperidin-1-yl | H | X$_4$-C(O)-(4-F-C$_6$H$_4$) | H | 458 |
| 366 | X$_2$-O-C(CH$_3$)$_3$ | H | X$_4$-C(O)-CH$_3$ | H | 366 |
| 367 | X$_2$-piperidin-1-yl | H | X$_4$-C(O)-(3-CN-C$_6$H$_4$) | H | 465 |

TABLE 1-continued
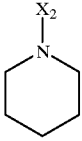
| No. | R₂ | R₃ | R₄ | R₅ | MW (M⁺) |
|---|---|---|---|---|---|
| 368 | 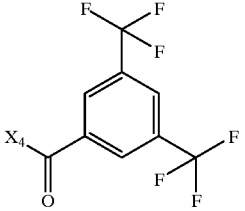 | H | 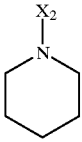 | H | 576 |
| 369 | 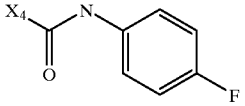 | H | 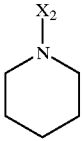 | H | 473 |
| 370 | 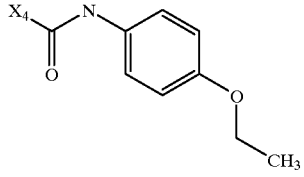 | H | 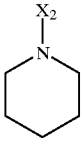 | H | 499 |
| 371 | 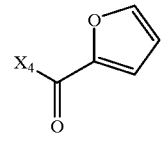 | H | 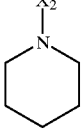 | H | 430 |
| 372 | 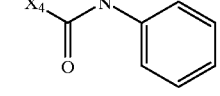 | H | 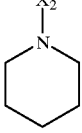 | H | 455 |
| 373 | 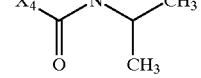 | H | 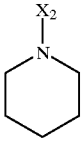 | H | 421 |
| 374 | 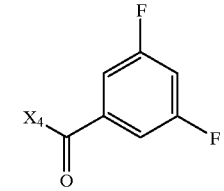 | H |  | H | 476 |

TABLE 1-continued
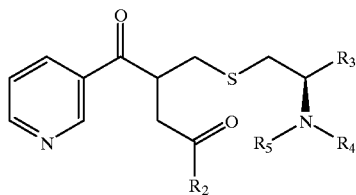
| No. | R₂ | R₃ | R₄ | R₅ | MW (M⁺) |
|---|---|---|---|---|---|
| 375 | piperidine-N-X₂ | H | X₄-C(O)-C₆H₄-CN (para) | H | 465 |
| 376 | X₂-O-C₆H₄-Cl (para) | H | X₄-C(O)-CH₃ | H | 421 |
| 377 | X₂-NH-CH₂CH₂-C₆H₄-SO₂NH₂ (para) | H | X₄-C(O)-CH₃ | H | 493 |
| 378 | X₂-NH-(2-pyrimidinyl) | H | X₄-C(O)-CH₃ | H | 387 |
| 379 | X₂-N(CH₃)₂ | azetidine-N-C(O)-X₃ | X₄-C(O)-CH₃ | H | 421 |
| 380 | X₂-N(CH₃)₂ | pyrrolidine-N-C(O)-X₃ | X₄-C(O)-CH₃ | H | 435 |
| 381 | X₂-N(CH₃)₂ | (S)-proline ethyl ester-N-C(O)-X₃ | X₄-C(O)-CH₃ | H | 507 |

TABLE 1-continued
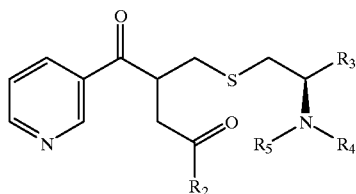
| No. | R₂ | R₃ | R₄ | R₅ | MW (M⁺) |
|---|---|---|---|---|---|
| 382 | X₂–N(CH₃)₂ | tert-butyl L-proline ester, N-acyl (X₃) | X₄–C(O)CH₃ | H | 535 |
| 383 | X₂–N(CH₃)₂ | L-proline (HO₂C–), N-acyl (X₃) | X₄–C(O)CH₃ | H | 479 |
| 384 | X₂–N(CH₃)₂ | piperidine N-acyl (X₃) | X₄–C(O)CH₃ | H | 449 |
| 385 | X₂–N(CH₃)₂ | morpholine N-acyl (X₃) | X₄–C(O)CH₃ | H | 451 |
| 386 | X₂–N(CH₃)₂ | cyclohexyl–NH–C(O)–X₃ | X₄–C(O)CH₃ | H | 463 |
| 387 | X₂–N(CH₃)₂ | Ph(CH₂)₃–NH–C(O)–X₃ | X₄–C(O)CH₃ | H | 499 |

TABLE 1-continued
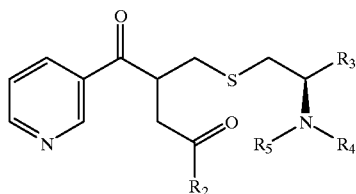
| No. | R2 | R3 | R4 | R5 | MW (M+) |
|---|---|---|---|---|---|
| 388 | X2-N(CH3)2 | 3-pyridyl-CH2CH2-N(X3)C(=O)- | X4-C(=O)CH3 | H | 486 |
| 389 | X2-N-(CH2)4-phenyl | H | X4-C(=O)CH3 | H | 442 |
| 390 | X2-O-C(CH3)3 | X3-O-C(=O)-CH2CH3 | X4-C(=O)CH3 | H | 439 |
| 391 | X2-O-C(CH3)3 | X3-O-C(=O)-CH2CH3 | X4-C(=O)-O-CH2-fluorenyl | H | 619 |
| 392 | X2-O-C(CH3)3 | X3-O-C(=O)-CH2CH3 | H | H | 397 |
| 393 | X2-O-C(CH3)3 | X3-O-C(=O)-CH3 | X4-C(=O)-NH-CH2CH2CH3 | H | 482 |

TABLE 1-continued

| No. | R₂ | R₃ | R₄ | R₅ | MW (M⁺) |
|---|---|---|---|---|---|
| 394 | X₂-O-C(CH₃)₂-CH₃ | X₃-C(O)-O-CH₃ | X₄-C(O)-NH-cyclohexyl | H | 522 |
| 395 | X₂-OH | X₃-C(O)-O-CH₃ | X₄-C(O)-NH-CH₂-CH₂-CH₃ | H | 426 |
| 396 | X₂-OH | X₃-C(O)-O-CH₃ | X₄-C(O)-NH-cyclohexyl | H | 466 |
| 397 | X₂-piperidinyl | H | X₄-C(O)-CH₃ | X₅-CH₂-CH₂-CH₃ | 434 |
| 398 | X₂-piperidinyl | H | X₄-C(O)-(3,5-difluorophenyl) | X₅-CH₂-CH₂-CH₃ | 532 |
| 399 | X₂-piperidinyl | H | X₄-C(O)-(4-fluorophenyl) | X₅-CH₂-CH₂-CH₃ | 514 |
| 400 | X₂-piperidinyl | H | X₄-C(O)-NH-cyclohexyl | X₅-CH₂-CH₂-CH₃ | 517 |

TABLE 1-continued

| No. | R₂ | R₃ | R₄ | R₅ | MW (M⁺) |
|-----|-----|-----|-----|-----|---------|
| 401 | X₂–piperidinyl | H | X₄–C(O)–NH–(4-methylphenyl) | X₅–CH₂CH₂CH₂CH₃ | 525 |
| 402 | X₂–piperidinyl | H | X₄–C(O)–NH–CH(CH₃)₂ | X₅–CH₂CH₂CH₂CH₃ | 477 |
| 403 | X₂–piperidinyl | H | X₄–C(O)–adamantyl | X₅–CH₂CH₂CH₂CH₃ | 554 |
| 404 | X₂–piperidinyl | H | X₄–C(O)–CH₂CH₂–cyclopentyl | X₅–CH₂CH₂CH₂CH₃ | 516 |
| 405 | X₂–piperidinyl | H | X₄–C(O)–(4-cyanophenyl) | X₅–CH₂CH₂CH₂CH₃ | 521 |
| 406 | X₂–piperidinyl | H | X₄–C(O)–NH–(4-ethoxyphenyl) | X₅–CH₂CH₂CH₂CH₃ | 555 |

TABLE 1-continued

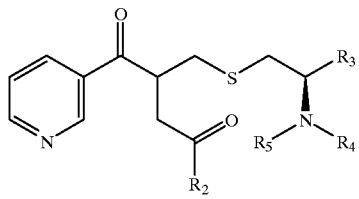

| No. | R₂ | R₃ | R₄ | R₅ | MW (M⁺) |
|---|---|---|---|---|---|
| 407 | $X_2$–CH(CH$_3$)$_2$ | CH(CH$_3$)–O–C(=O)–$X_3$ (ethyl ester) | $X_4$–C(=O)–N(propyl)(CH$_3$) | H | 453 |
| 408 | $X_2$–N(pyrrolidinyl) | CH(CH$_3$)–O–C(=O)–$X_3$ | $X_4$–C(=O)–N(propyl)(CH$_3$) | H | 479 |
| 409 | $X_2$–N(pyrrolidinyl) | CH(CH$_3$)–O–C(=O)–$X_3$ | $X_4$–C(=O)–N(propyl)(CH$_3$) | H | 493 |
| 410 | $X_2$–N(morpholinyl) | CH(CH$_3$)–O–C(=O)–$X_3$ | $X_4$–C(=O)–N(propyl)(CH$_3$) | H | 495 |
| 411 | $X_2$–N(4-methylpiperazinyl) | CH(CH$_3$)–O–C(=O)–$X_3$ | $X_4$–C(=O)–N(propyl)(CH$_3$) | H | 508 |
| 412 | $X_2$–NH–cyclohexyl | CH(CH$_3$)–O–C(=O)–$X_3$ | $X_4$–C(=O)–N(propyl)(CH$_3$) | H | 507 |
| 413 | $X_2$–CH(CH$_3$)$_2$ | CH(CH$_3$)–O–C(=O)–$X_3$ | $X_4$–C(=O)–NH–cyclohexyl | H | 493 |

TABLE 1-continued

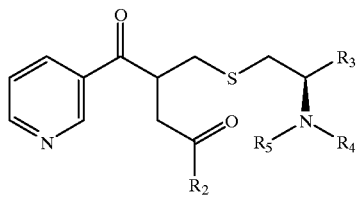

| No. | R₂ | R₃ | R₄ | R₅ | MW (M⁺) |
|---|---|---|---|---|---|
| 414 | pyrrolidinyl-X₂ | X₃-OC(O)-OEt (ethyl carbonate via X₃) — ethyl, X₃-C(O)O- | X₄-C(O)-NH-cyclohexyl | H | 519 |
| 415 | pyrrolidinyl-X₂ | ethyl carbonate via X₃ | X₄-C(O)-NH-cyclohexyl | H | 533 |
| 416 | morpholinyl-X₂ | ethyl carbonate via X₃ | X₄-C(O)-NH-cyclohexyl | H | 535 |
| 417 | 4-methylpiperazinyl-X₂ | ethyl carbonate via X₃ | X₄-C(O)-NH-cyclohexyl | H | 548 |
| 418 | cyclohexyl-NH-X₂ | ethyl carbonate via X₃ | X₄-C(O)-NH-cyclohexyl | H | 547 |
| 419 | X₂-O-CH₂-O-C(O)-C(CH₃)₃ (pivaloyloxymethyl) | H | X₄-C(O)-CH₃ | H | 425 |
| 420 | piperidinyl-X₂ | H | H | H | 336 |

TABLE 1-continued
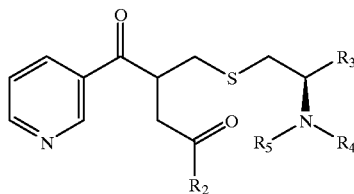
| No. | $R_2$ | $R_3$ | $R_4$ | $R_5$ | MW ($M^+$) |
|---|---|---|---|---|---|
| 421 | X₂–N(piperidine) | H | X₄–C(=O)–CH₂–NH₂ | H | 393 |
| 422 | X₂–OH | X₃–C(=O)–O–CH₂CH₃ | X₄–C(=O)–CH₃ | H | 382 |
| 423 | X₂–N(CH₃)–CH₂CH₂–N(CH₃)₂ | X₃–C(=O)–O–CH₂CH₃ | X₄–C(=O)–CH₃ | H | 467 |
| 424 | X₂–N(CH₃)–CH₂CH₂CH₂–N(CH₃)₂ | X₃–C(=O)–O–CH₂CH₃ | X₄–C(=O)–CH₃ | H | 481 |
| 425 | X₂–NH–CH₂CH₂CH₂–N(morpholine) | X₃–C(=O)–O–CH₂CH₃ | X₄–C(=O)–CH₃ | H | 509 |
| 426 | X₂–N(CH₃)–CH₂CH₂–N(CH₂CH₃)₂ | X₃–C(=O)–O–CH₂CH₃ | X₄–C(=O)–CH₃ | H | 495 |
| 427 | X₂–N(4-methylpiperazine) | X₃–C(=O)–O–CH₂CH₃ | X₄–C(=O)–CH₃ | H | 465 |

TABLE 1-continued

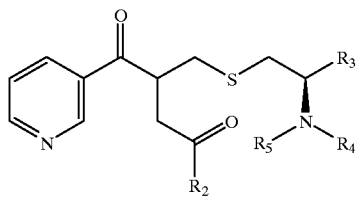

| No. | R₂ | R₃ | R₄ | R₅ | MW (M⁺) |
|---|---|---|---|---|---|
| 428 | X₂-N(piperidine-4-pyrrolidine) | X₃-C(O)O-CH₂CH₃ | X₄-C(O)CH₃ | H | 519 |
| 429 | X₂-N(CH₃)-CH₂CH₂CH₂-N(CH₃)₂ | X₃-C(O)-N(CH₃)-CH₂CH₂CH₂-N(CH₃)₂ | X₄-C(O)CH₃ | H | 551 |
| 430 | X₂-NH-CH₂CH₂CH₂-morpholine | X₃-C(O)-NH-CH₂CH₂CH₂-morpholine | X₄-C(O)CH₃ | H | 607 |
| 431 | X₂-N(CH₃)-CH₂CH₂-N(CH₂CH₃)₂ | X₃-C(O)-N(CH₃)-CH₂CH₂-N(CH₂CH₃)₂ | X₄-C(O)CH₃ | H | 579 |
| 432 | X₂-N(CH₃)-CH₂CH₂-N(CH₃)₂ | X₃-C(O)-N(CH₃)-CH₂CH₂-N(CH₃)₂ | X₄-C(O)CH₃ | H | 523 |
| 433 | X₂-N(4-methylpiperazine) | X₃-C(O)-(4-methylpiperazine) | X₄-C(O)CH₃ | H | 519 |

TABLE 1-continued
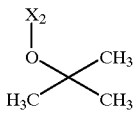
| No. | R2 | R3 | R4 | R5 | MW (M+) |
|-----|----|----|----|----|---------|
| 434 | 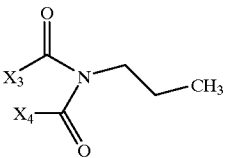 | |  | H | 436 |
| 435 | 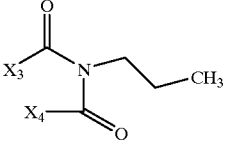 | | 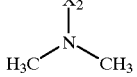 | H | 379 |
| 436 | 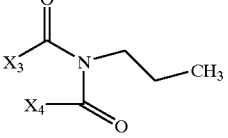 | | 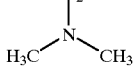 | H | 407 |
| 437 | 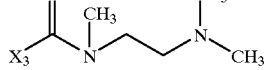 |  | 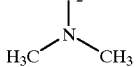 | H | 446 |
| 438 | 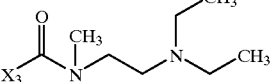 |  | 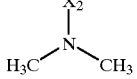 | H | 494 |
| 439 | 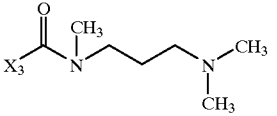 |  | 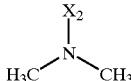 | H | 480 |
| 440 | 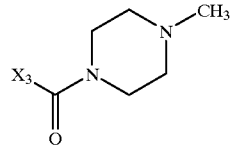 |  | 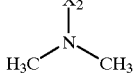 | H | 464 |
| 441 | 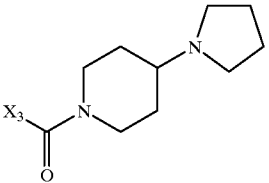 |  | | H | 518 |

TABLE 1-continued
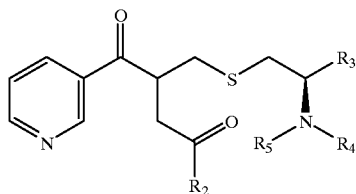
| No. | R₂ | R₃ | R₄ | R₅ | MW (M⁺) |
|---|---|---|---|---|---|
| 442 | X₂–N(CH₃)₂ (H₃C–N–CH₃) | X₃–C(O)–NH–(CH₂)₃–morpholine | X₄–C(O)–CH₃ | H | 508 |
| 443 | X₂–piperidine (N-linked) | H | X₄–C(O)–CH₂–N(CH₃)₂ | H | 421 |
| 444 | X₂–piperidine (N-linked) | H | X₄–C(O)–CH₂–NH–CH₂–C₆H₅ | H | 438 |
| 445 | X₂–NH–CH₂–(2-pyridyl) | X₃–C(O)–O–CH₂CH₃ | X₄–C(O)–CH₃ | H | 473 |
| 446 | X₂–NH–CH₂–(3-pyridyl) | X₃–C(O)–O–CH₂CH₃ | X₄–C(O)–CH₃ | H | 473 |
| 447 | X₂–NH–(3-pyridyl) | X₃–C(O)–O–CH₂CH₃ | X₄–C(O)–CH₃ | H | 459 |
| 448 | X₂–NH–(4-pyridyl) | X₃–C(O)–O–CH₂CH₃ | X₄–C(O)–CH₃ | H | 459 |

TABLE 1-continued
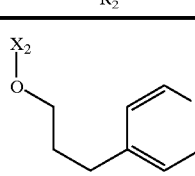
| No. | R$_2$ | R$_3$ | R$_4$ | R$_5$ | MW (M$^+$) |
|---|---|---|---|---|---|
| 449 | 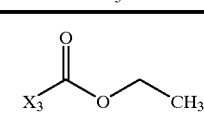 | 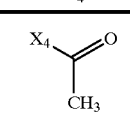 | 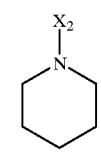 | H | 502 |
| 450 | 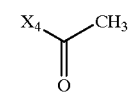 | H | 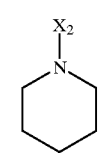 | H | 378 |
| 451 | 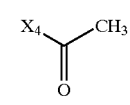 | H | 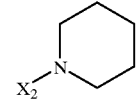 | H | 378 |
| 452 | 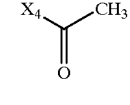 | H | 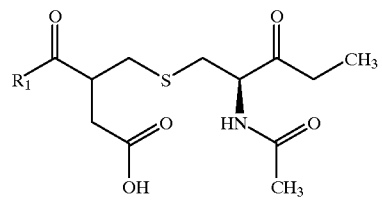 | H | 410 |
TABLE 2
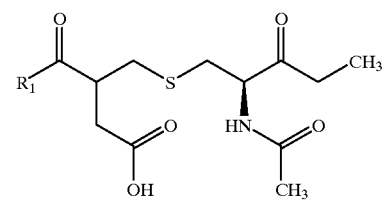
| No. | R$_1$ | MW (M$^+$) |
|---|---|---|
| 462 | 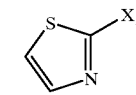 | 374 |
| 463 | 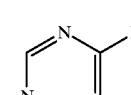 | 424 |
| 464 | 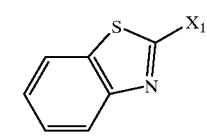 | 369 |
| 465 | 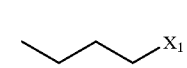 | 347 |

TABLE 2-continued

[structure diagram showing compound with R₁ group, sulfur linker, and acetamide side chain with CH₃, OH, O groups]

| No. | R₁ | MW (M⁺) |
|---|---|---|
| 466 | 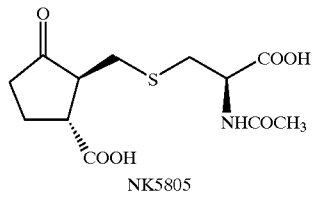 | 416 |

Example 51

PC12 Cell Protection Against Taxol Assay

Differentiated PC12 (rat pheochromocytoma) cells are utilized to model taxol-damaged neurons. Differentiated PC12 have nerve-like morphology which is disrupted by administration of taxol. Quantification of damage to differentiated PC12 cells by taxol is measured by the release of LDH that occurs upon cell necrosis.

Method

PC12 cells are differentiated with NGF (100 mg/ml) for 29 hours. Compounds are added for 19 hours (pre-treatment), then taxol (0.24 mM) is added. 72 hours (3 days) after taxol addition, cell survival is assayed by LDH release. Complete cellular protection (100%) is defined as the protection derived from 30 mM NK5805. NK5805 is a reference compound for neuronal protection. It was originally identified by Nippon Kayaku Co. Ltd. in published PCT WO99/05091 and has the following structure:

[structure of NK5805]

NK5805

LDH values were quantified by calculating the following % survival, relative to 30 mM NK5805, according to Equation (1):

$$\frac{100 \times \{(LDH \text{ for taxol}) - (LDH \text{ for taxol} + \text{test compound})\}}{(LDH \text{ for taxol}) - (LDH \text{ for taxol} + 30 \text{ mM } NK5805)} \quad \text{Eq. (1)}$$

In this example, a 100% protection level is equivalent to the group given no taxol.

Results

Table 2 identifies preferred compounds with significant protection of differentiated PC12 from taxol damage. To this end, preferred compounds (from Table 1 above) having a protection level of at least 50% at 10 µM concentration in this assay are as follows: 5, 8, 24, 32, 58, 60, 61, 74, 81, 90–92, 94, 95, 97–102, 105, 106, 110–113, 115–117, 121–123, 125–129, 132, 136, 140, 164, 169, 170, 174–184, 187–189, 195, 196, 198, 202, 204–208, 214–226, 240, 244, 246, 249, 251–253, 257, 259, 260, 263, 264, 268–273, 275, 277–282, 285, 335, 337–345, 355, 357–375, 378–388, 420–426, 432–435 and 444.

Example 52

Rat Superior Cervical Gangloon Cell Protection Against Taxol Assay

Rat superior cervical ganglion (SCG) neurons have been used extensively to model neuronal systems. This assay utilizes SCG neurons to identify potential protective agents against taxol-induced neuropathy.

Method

Neonatal rat SCG neurons are cultured with 2.5 ng/ml NFG and the test compounds. After 36 hours 1 mM taxol is added. 72 hours (3 days) after taxol addition, cell survival is assayed by LDH release. Complete cellular protection (100%) is defined as the protection derived from 30 mM. LDH values were quantified by calculating the following % survival, relative to 30 mM NK5805 as noted in Equation (1) above.

Results

Table 3 identifies preferred compounds with significant protection of rat SCG from taxol damage. To this end, preferred compounds (from Table 1 above having a protection level of at least 50% at 10 µM concentration in this assay are as follows: 1, 2, 8, 25, 30, 32, 59–61, 74, 77, 120, 129, 130, 132–135, 139, 140, 143–146, 148, 152, 153, 159, 162–164, 168, 169, 175, 187–189, 194, 196, 197, 206, 218, 223, 226, 258, 259, 263, 356, 370, 378–388, 395, 396, 407, 410, 413, 416, 421, 422 and 435–442.

Example 53

Efficacy of Representative Compounds in Rat Taxol Neuropathy Model

In vivo efficacy of representative compounds were tested with rat taxol induced neuropathy model reported by Cliffer et al. (Ann. Neurol 43:46–55, 1998).

Method Sprague-Dawley female rats (215–225g) were used. One week prior to the initiation of dosing with test compounds, base line electrophysiological recording were obtained. Dosing of the test compounds was initiated one day prior to the first injection of taxol (A.G. Scientific). Beginning on Day 2 animals were injected with total of two doses of 15 mg/kg paclitaxel giving 3 days apart, for a cumulative dose of 30 mg/ml.

On Day 1 of the study, all rat were randomized into groups of 10 each and weighed. Dosing with test compounds was initiated on Day 1 and continued for a total of 45 days. Test compounds were administered by intraperitoneal (i.p.) injection or by post orum (p.o.) gavage in conscious once daily. Paclitaxel was administered on Day 2 and 5 by tail vein injection at 6 mg/ml in 50% saline/25%Cremophore/25% ethanol. One group was given the paclitaxel vehicle alone in an equivalent volume. Test compounds were formulated for dosing daily, immediately prior to dosing. The compounds were formulated by adding 15% of the final volume of pure PEG400 to the compounds and mixed on an orbital shaker for 40 minutes. Following dissolution, saline was added and the solution was vortexed. Taxol (A.G. Scientific) is solvated with Cremophore-ethanol vehicle at 12 mg/ml and then diluted 50/50 with saline. The test compounds are solvated with saline at appropriate concentration.

Sensory and motor nerve conduction velocities were evaluated using a method based in the protocol described by De Koning and Gispen (Peptides 8:415–422, 1987). Electrophysiological evaluation was carried out as a double blind study. Animals were anesthetized with isofluorane. In order to maintain body temperature, anesthetized animals were placed on Deltaphase ™ Isothermal Pads and rectal temperatures were monitored. Stimulating needle electrodes were inserted close to the sciatic nerve at the sciatic notch and the tibial nerve near the ankle. Subcutaneous recording electrodes were placed over the distal lumbricales foot muscles. Stimuli were supramaximal square-waves of 0.1 msec duration generated with a Grass S88 Stimulator through a Grass stimulation isolation unit. An ETH-260 Bride/Bio Amplifier (CB Sciences Inc), computer (Macintosh Iici), and data acquisition system (MacLab/200) were used for the recordings. The motor and sensory nerve conduction velocities were calculated by measuring the distance between the sciatic notch and ankle sites, and the latency between the M-wave and the H-reflex. The electrophysiological evaluations were conducted 2 weeks later. Statistical analysis was carried out using unpaired t-tests and repeated measures of analysis of variance (ANOVA) using Statview. In all cases 5% was chosen as the level of statistical significance in two-tailed tests.

Results

Compound No. 60 was active to ameliorate the taxol-induced retardation of sensory nerve conduction velocity by i.p. administration at 10 mg/kg (see FIG. 1, 3). Compound No.188 (40 mg/kg), compound No. 440 and compound No. 438 (20 mg/kg) were active to ameliorate the taxol-induced retardation of sensory nerve conduction velocity by p.o. administration (see FIG. 2,3 ). Compound No. 189 was active to ameliorate the taxol-induced retardation of sensory nerve conduction velocity by i.p. administration at 2.5 mg/kg (see FIG. 2) and p.o. administration at 20 mg/kg (see FIG. 3). Thus, representative compounds of this invention, such as compound No. 60, compound No. 188, compound No. 440, compound No. 438 and compound No. 189, are effective in this in vivo rat neuropathy model.

It will be appreciated that, although specific embodiments of the invention have been described herein for purposes of illustration, various modifications may be made without departing from the spirit and scope of the invention. Accordingly, the invention is not limited except as by the appended claims.

We claim:

1. A compound having the structure:

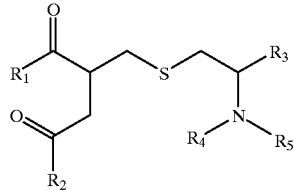

or a stereoisomer or pharmaceutically acceptable salt thereof,
wherein:
$R_1$ is pyridyl;
$R_2$ is —$NR_{2b}R_{2c}$;
$R_3$ is hydrogen, keto, —C(=O)O$R_{3a}$ or —C(=O)$NR_{3b}R_{3c}$;

$R_4$ is hydrogen, alkyl, substituted alkyl, aryl, substituted aryl, —C(=O)$R_{4a}$, —C(=O)O$R_{4b}$, —C(=O)$NR_{4c}R_{4d}$, —OC(=O)$NR_{4c}R_{4d}$ or —SO$_2R_{4e}$,
or wherein $R_3$ and $R_4$ taken together form a heterocyclic ring or substituted heterocyclic ring; and
$R_5$ is hydrogen, alkyl or cycloalkyl;
provided that at least one of $R_3$ and $R_5$ is hydrogen;
and wherein:
$R_{2b}$ and $R_{2c}$ taken together with the nitrogen atom to which they are attached from a heterocyclic ring;
$R_{3a}$, $R_{3b}$ and $R_{3c}$, are the same or different and independently hydrogen, alkyl, substituted alkyl, aryl, substituted aryl, arylalkyl, substitued arylalkyl, heterocycle, substituted heterocyle, heterocyclealkyl, substituted heterocyclealkyl, or a radical of the formula —$Y_3$—$Z_3$—$R_{3d}$, where $Y_3$ is alkanediyl, substitute alkanediyl or a direct bond, $Z_3$ is —O—, —S—, —SO$_2$—, —N($R_{3e}$)—, —C(=O)—, —C(=O)O—, —OC(=O)—, —NHC(=O)—, —C(=O)N($R_{3e}$)— or a direct bond, and $R_{3d}$ and $R_{3e}$ are the same or different and independently hydrogen, amino, alkyl, substituted alkyl, aryl, substituted aryl, arylalkyl, substituted arylalkyl, heterocycle, substituted heterocycle, heterocylealkyl or substituted heterocyclealkyl, or $R_{3d}$ and $R_{3e}$ taken together with the nitrogen atom to which they are attached form a heterocycle or substituted heterocycle; or $R_{3b}$ and $R_{3c}$ taken together with the nitrogen atom to which they are attached from a heterocyclic ring or substituted heterocyclic ring;

$R_{4a}$, $R_{4b}$, $R_{4c}$, $R_{4d}$ and $R_{4e}$ are the same or different and independently hydrogen, alkyl, substituted alkyl, aryl, substituted aryl, arylalkyl, substituted arylalkyl, or a radical of the formula —$Y_4$—$Z_4$—$R_{4f}$, where $Y_4$ is alkanediyl, substituted alkanediyl or a direct bond, $Z_4$ is —O—, —S—, —SO$_2$—, —N($R_{4g}$)—, —C(=O)—, —C(=O)O—, —OC(=O)—, —NHC(=O)—, —C(=O)N($R_{4g}$)— or a direct bond, and $R_{4f}$ and $R_{4g}$ are the same or different and independently hydrogen, amino, alkyl, substituted alkyl, aryl, substituted aryl, arylalkyl, substituted arylalkyl, heterocycle, substituted heterocycle, heterocylealkyl or substituted heterocyclealkyl, or $R_{4f}$ and $R_{4g}$ taken together with the nitrogen atom to which they are attached form a heterocycle or substituted heterocycle; or R and $R_{4d}$ taken together with the nitrogen atom to which they are attached from a heterocyclic ring or substituted heterocyclic ring; and each of said substituted moieties being substituted with at least one alkyl, alkanediyl, aryl, arylalkyl, heteroaryl, heteroarylalkyl, heterocyclic or heterocyclealkyl.

2. The compound of claim 1 wherein $R_1$ is pyrid-3-yl.
3. The compound of claim 1 wherein $R_2$ is piperidin-1-yl.
4. The compound of claim 1 wherein $R_3$ is hydrogen.
5. The compound of claim 1 wherein $R_3$ is —C(=O)$NR_{3b}R_{3c}$.
6. The compound of claim 5 wherein $R_{3b}$ and $R_3$, are the same or different and independently hydrogen, alkyl or substituted alkyl.
7. The compound of claim 5 wherein $R_{3b}$ and $R_{3c}$ taken together with the nitrogen atom to which they are attached form a heterocyclic ring or substituted heterocyclic ring.
8. The compound of claim 1 wherein $R_4$ is alkyl or aryl.
9. The compound of claim 1 wherein $R_4$ is —C(=O)$R_{4a}$ and $R_{4a}$ is aryl or substituted aryl.
10. The compound of claim 1 wherein $R_4$ is —C(=O)O$R_{4b}$.

11. The compound of claim 10 wherein $R_{4b}$ is alkyl or substituted alkyl.

12. The compound of claim 10 wherein $R_{4b}$ is aryl, substituted aryl, arylalkyl or substituted arylalkyl.

13. The compound of claim 1 wherein $R_4$ is —C(=O)NR$_{4c}$R$_{4d}$.

14. The compound of claim 13 wherein $R_{4c}$ is hydrogen.

15. The compound of claim 13 wherein $R_{4d}$ is alkyl.

16. The compound of claim 13 wherein $R_{4d}$ is aryl, substituted aryl, arylalkyl or substitute arylalkyl.

17. The compound of claim 1 wherein $R_4$ is —SO$_2$R$_{4e}$.

18. The compound of claim 17 wherein $R_{4e}$ is aryl or substituted aryl.

19. The compound of claim 1 wherein $R_5$ is methyl, ethyl, n-propyl or n-butyl.

20. The compound of claim 1 wherein $R_5$ is cyclohexyl.

21. The compound of claim 1 having the structure:

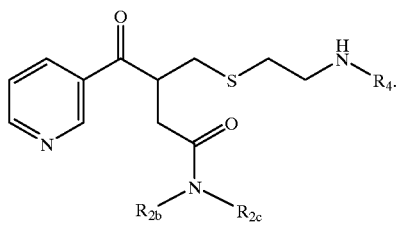

22. The compound of claim 1 having the structure:

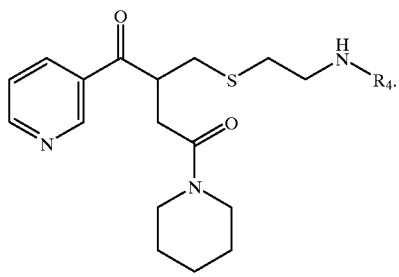

23. The compound of claim 1 having the structure:

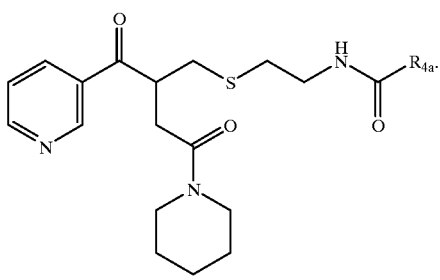

24. The compound of claim 1 having the structure:

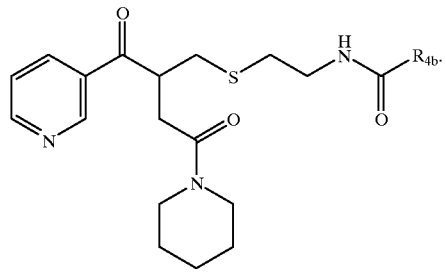

25. The compound of claim 1 having the structure:

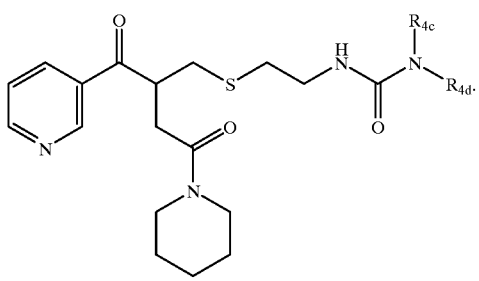

26. The compound of claim 1 having the structure:

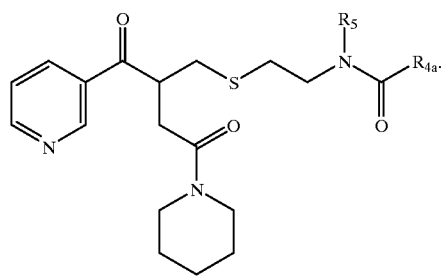

27. A composition comprising the compound of claim 1 and a pharmaceutically acceptable carrier.

28. A method for treating chemotherapy-induced neuropathy in a patient, comprising administering to the patient in need thereof an effective amount of the composition of claim 27.

* * * * *

UNITED STATES PATENT AND TRADEMARK OFFICE
CERTIFICATE OF CORRECTION

PATENT NO.    : 6,399,606 B1
DATED         : June 4, 2002
INVENTOR(S)   : Moorthy S.S. Palanki et al.

It is certified that error appears in the above-identified patent and that said Letters Patent is hereby corrected as shown below:

<u>Column 168,</u>
Line 13, "substituted arylalkyl" should read -- substituted arylalkyl --.
Line 14, "substituted heterocyle" should read -- substituted heterocycle --.
Line 45, "or R and $R_{4d}$" should read -- or $R_{4c}$ and $R_{4d}$ --.
Line 57, "wherein $R_{3b}$ and $R_3$" should read -- wherein $R_{3b}$ and $R_{3c}$ --.

Signed and Sealed this

Thirty-first Day of December, 2002

JAMES E. ROGAN
*Director of the United States Patent and Trademark Office*